US010858448B2

(12) United States Patent
Horowitz

(10) Patent No.: US 10,858,448 B2
(45) Date of Patent: Dec. 8, 2020

(54) ANTI-SURROGATE LIGHT CHAIN ANTIBODIES

(71) Applicant: i2 Pharmaceuticals, Inc., Boulder, CO (US)

(72) Inventor: Lawrence Horowitz, Mountain View, CA (US)

(73) Assignee: I2 PHARMACEUTICALS, INC., Boulder, CO (US)

( * ) Notice: Subject to any disclaimer, the term of this patent is extended or adjusted under 35 U.S.C. 154(b) by 89 days.

(21) Appl. No.: 15/548,274

(22) PCT Filed: Jan. 27, 2016

(86) PCT No.: PCT/US2016/015166
§ 371 (c)(1),
(2) Date: Aug. 2, 2017

(87) PCT Pub. No.: WO2016/126488
PCT Pub. Date: Aug. 11, 2016

(65) Prior Publication Data
US 2018/0265594 A1 Sep. 20, 2018

Related U.S. Application Data

(60) Provisional application No. 62/111,018, filed on Feb. 2, 2015.

(51) Int. Cl.
*C07K 16/42* (2006.01)
*C07K 16/18* (2006.01)
*G01N 33/564* (2006.01)

(52) U.S. Cl.
CPC .............. *C07K 16/42* (2013.01); *C07K 16/18* (2013.01); *G01N 33/564* (2013.01); *C07K 2317/33* (2013.01); *C07K 2317/92* (2013.01); *C07K 2317/94* (2013.01); *G01N 2800/102* (2013.01)

(58) Field of Classification Search
None
See application file for complete search history.

(56) References Cited

U.S. PATENT DOCUMENTS

| 5,182,205 A | 1/1993 | Bauer et al. |
| 6,335,175 B1 | 1/2002 | Tsuganezawa et al. |
| 2003/0215453 A1 | 11/2003 | Dedera et al. |
| 2006/0257397 A1 | 11/2006 | Throsby et al. |
| 2010/0062950 A1 | 3/2010 | Bhatt et al. |
| 2012/0201756 A1 | 8/2012 | Sexton |

FOREIGN PATENT DOCUMENTS

| EP | 0269127 A2 | 6/1988 |
| WO | WO 2008/118970 A2 | 10/2008 |
| WO | WO 2010/006286 A2 | 1/2010 |
| WO | WO 2016/126488 A1 | 8/2016 |

OTHER PUBLICATIONS

Lloyd et al. (Protein Engineering, Design & Selection 2009, 22:159-168).*
Extended European Search Report for Application No. PCT/US2016/015166 dated Oct. 16, 2018, 25 pages.
Hauser et al., "Calmodulin inhibition of E2A stops expression of surrogate light chains of the pre-B-cell receptor and CD19," Molecular Immunology (2010); 47(5): 1031-1038.
Karasuyama et al., "A complex of glycoproteins is associated with V-preB/lambda-5 surrogate light chain on the surface of mu heavy chain-negative early precursor B cell lines," Journal of Experimental Medicine (1993); 178(2): 469-478.
Kiyokawa et al., "Diagnostic importance of CD179a/b as markers of precursor B-cell lymphoblastic lymphoma," Modern Patho. (2004); 17(4): 423-429.
Mundt et al., "Only VpreB1, but not VpreB2, is expressed at levels which allow normal development of B cells," International Immunology (2006): 18 (1): 163-172.
Yim et al., "The potential role of gene copy number variation in susceptibility to rheumatoid arthritis," Molecular Immunology (2010); 48(11): 1338-1343.
Collins, et al., "A genome annotation-driven approach to cloning the human ORFeome." Genome Biol. (2004); 5(10):R84.
Hollis, et al., "Immunoglobulin λ light-chain-related genes 14.1 and 16.1 are expressed in pre-B cells and may encode the human immunoglobulin ω light-chain protein." Proc Natl Acad Sci U S A. (1989); 86(14): 5552-5556.
International Preliminary Report on Patentability for International Application No. PCT/US2016/015166 dated Aug. 8, 2017, 6 pages.
International Search Report and Written Opinion for International Application No. PCT/US2016/015166 dated Jul. 8, 2016, 10 pages.
Karasuyama, et al., "Surrogate light chain in B cell Development." Advances in Immunology, (1996); 63:1-41.
Kitamura, et al., "A critical role of λ 5 protein in B cell development." Cell (1992); 69(5):823-831.
Lemmers, et al., "The Human (ψL+µ-) proB Complex: Cell Surface Expression and Biochemical Structure of a Putative Transducing Receptor." Blood (1999); 93: 4336-4346.
Meffre, et al., "Circulating human B cells that express surrogate light chains and edited receptors." Nature Immunology (2000); 207-213.
Melchers, et al., "Fit for life in the immune system? Surrogate L chain tests H chains that test L chains." Proc Natl Acad Sci U S A. (1999); 96(6): 2571-2573.
Melchers, et al., "The surrogate light chain in B-cell development," Immunology Today (1993);14(2):60-68.
Minegishi, et al., "Mutations in the human λ5/14.1 gene result in B cell deficiency and agammaglobulinemia." J Exp Med. (1998);187(1): 71-77.

(Continued)

*Primary Examiner* — Sharon X Wen
(74) *Attorney, Agent, or Firm* — Cooley LLP

(57) ABSTRACT

The present invention concerns anti-surrogate light chain antibodies and their uses. In particular, the present invention concerns anti-VpreB1 antibodies and their uses.

6 Claims, 40 Drawing Sheets
Specification includes a Sequence Listing.

(56) References Cited

OTHER PUBLICATIONS

UniProt Accession P12018. PREB_HUMAN. (Jan. 7, 2015) [Retrieved from the Internet Apr. 2, 2016: <http://www.uniprot.org/uniprot.org/uniprot/P12018.txt?version=140>]; 5 pages.
UniProt Accession P15814. IGLL1_HUMA (Jan. 7, 2015) [Retrieved from the Internet Apr. 2, 2016: <http://www.uniprot.org/uniprot.org/uniprot/P15814.txt?version=144>]; 5 pages.
Xu, et al., "Combinatorial surrobody libraries." Proc. Natl. Acad Sci. USA (2008);105(31):10756-10761.
Xu, et al., "Surrobodies with Functional Tails." J Mol. Biol. (2010); 397(1): 352-360.

* cited by examiner

FIG. 1

(SEQ ID NO: 1)
MSWAPVLLMLFVYCTGCGPQPVLHQPPAMSSALGTTIRLTCTLRNDHDIGVYSVYWYQQRPGHPPRFLLRYFSQ
SDKSQGPQVPPRFSGSKDVARNRGYLSISELQPEDEAMYYCAMGARSSEKEEREREWEEEMEPTAARTRV (SEQ ID NO: 2)
MAWTSVLLMLLAHLTGCGPQPMVHQPPSASSSLGATIRLSCTLSNDHNIGIYSIYWYQQRPGHPPRFLLRYFSH
SDKHQGPDIPPRFSGSKDTARNLGYLSISELQPEDEAVYYCAVGLRSHEKKRMEREWEGEKSYTDLGS (SEQ ID NO: 3)
MAWTSVLLMLLAHLTGKGTLGVQGFLAPPVALLCPSDGHASIFSGCGPQPMVHQPPSASSSLGATIRLSCTLSN
DHNIGIYSIYWYQQRPGHPPRFLLRYFSHSDKHQGPDIPPRFSGSKDTARNLGYLSISELQPEDEAVYYCAVGL
RSHEKKRMEREWEGEKSYTDLGS (SEQ ID NO: 4)
MACRCLSFLLMGTFLSVSQTVLAQLDALLVFPGQVAQLSCTLSPQHVTIRDYGVSWYQQRAGSAPRYLLYYRSE
EDHHRPADIPDRFSAAKDEAHNACVLTISPVQPEDDADYYCSVGYGFSP (SEQ ID NO: 5)
MSWAPVLLMLFVYCTGCGPQPVLHQPPAMSSALGTTIRLTCTLRNDHDIGVYSVYWYQQRPGHPPRFLLRYFSQ
SDKSQGPQVPPRFSGSKDVARNRGYLSISELQPEDEAMYYCAMGA (SEQ ID NO: 6)
METDTLLLWVLLLWVPGSTGQPVLHQPPAMSSALGTTIRLTCTLRNDHDIGVYSVYWYQQRPGHPPRFLLRYFS
QSDKSQGPQVPPRFSGSKDVARNRGYLSISELQPEDEAMYYCAMGARSSEKEEREREWEEEMEPTAARTRVP

FIG. 2

(SEQ ID NO: 7)
MKLRVGQTLGTIPRQCEVLLLLLLLGLVDGVHHILSPSSAERSRAVGPGASVGSNRPSLWALPGRLLFQIIP
RGAGPRCSPHRLPSKPQFWYVFGGGTQLTILGQPKSDPLVTLFLPSLKNLQPTRPHVVCLVSEFYPGTLVVD
WKVDGVPVTQGVETTQPSKQTNNKYMVSSYLTLISDQWMPHSRYSCRVTHEGNTVEKSVSPAECS (SEQ ID NO: 8)
MRPGTGQGGLEAPGEPGPNLRQRWPLLLLGLAVVTHGLLRPTAASQSRALGPGAPGGSSRSSLRSRWGRFLL
QRGSWTGPRCWPRGFQSKHNSVTHVFGSGTQLTVLSQPKATPSVTLFPPSSEELQANKATLVCLMNDFYPGI
LTVTWKADGTPITQGVEMTTPSKQSNNKYAASSYLSLTPEQWRSRRSYSCQVMHEGSTVEKTVAPAECS (SEQ ID NO: 9)
MRPGTGQGGLEAPGEPGPNLRQRWPLLLLGLAVVTHGSVTHVFGSGTQLTVLSQPKATPSVTLFPPSSEELQ
ANKATLVCLMNDFYPGILTVTWKADGTPITQGVEMTTPSKQSNNKYAASSYLSLTPEQWRSRRSYSCQVMHE
GSTVEKTVAPAECS (SEQ ID NO: 10)
METDTLLLWVLLLWVPGSTGSVTHVFGSGTQLTVLSQPKATPSVTLFPPSSEELQANKATLVCLMNDFYPGI
LTVTWKADGTPITQGVEMTTPSKQSNNKYAASSYLSLTPEQWRSRRSYSCQVMHEGSTVEKTVAPAECS

FIG. 3

SEQ ID NO: 35

METDTLLLWVLLLWVPGSTGQPVLHQPPAMSSALGTTIRLTCTLRNDHDIGVYSVYWYQQRPG
HPPRFLLRYFSQSDKSQGPQVPPRFSGSKDVARNRGYLSISELQPEDEAMYYCAMGARSSVTH
VFGSGTQLTVLSQPKATPSVTLFPPSSEELQANKATLVCLMNDFYPGILTVTWKADGTPITQG
VEMTTPSKQSNNKYAASSYLSLTPEQWRSRRSYSCQVMHEGSTVEKTVAPAECS

FIG. 4A

```
       M   V   L   Q   T   Q   V   F   I   S   L   L   L   W   I   S   G   A   Y   G   D   I   V   .
  1  CAGCAAGATGGTGTT GCAGACCCAGGTCTT CATTTCTCTGTTGCT CTGGATCTCTGGTGC CTACGGGGACATCGT
     GTCGTTCTACCACAA CGTCTGGGTCCAGAA GTAAAGAGACAACGA GACCTAGAGACCACG GATGCCCCTGTAGCA

M   T   Q   S   P   D   S   L   A   V   S   L   G   E   R   A   T   I   N   C   K   S   S   Q   S   .
 76  GATGACCCAGTCTCC AGACTCCCTGGCTGT GTCTCTGGGCGAGAG GGCCACCATCAACTG CAAGTCCAGCCAGAG
     CTACTGGGTCAGAGG TCTGAGGGACCGACA CAGAGACCCGCTCTC CCGGTGGTAGTTGAC GTTCAGGTCGGTCTC

V   L   Y   S   S   N   N   K   N   Y   L   A   W   Y   Q   Q   K   P   G   Q   P   P   K   L   L   .
151  TGTTTTATACAGCTC CAACAATAAGAACTA CTTAGCTTGGTACCA GCAGAAACCAGGACA GCCTCCTAAGCTGCT
     ACAAAATATGTCGAG GTTGTTATTCTTGAT GAATCGAACCATGGT CGTCTTTGGTCCTGT CGGAGGATTCGACGA

I   Y   W   A   S   T   R   E   S   G   V   P   D   R   F   S   G   S   G   S   G   T   D   F   T   .
226  CATTTACTGGGCATC TACCCGGGAATCCGG GGTCCCTGACCGATT CAGTGGCAGCGGGTC TGGGACAGATTTCAC
     GTAAATGACCCGTAG ATGGGCCCTTAGGCC CCAGGACTGGCTAA GTCACCGTCGCCCAG ACCCTGTCTAAAGTG

L   T   I   S   S   L   Q   A   E   D   V   A   V   Y   Y   C   Q   Q   Y   Y   S   T   P   P   T   .
301  TCTCACCATCAGCAG CCTGCAGGCTGAAGA TGTGGCAGTTTATTA CTGTCAGCAATATTA TAGTACTCCTCCCAC
     AGAGTGGTAGTCGTC GGACGTCCGACTTCT ACACCGTCAAATAAT GACAGTCGTTATAAT ATCATGAGGAGGGTG

V   L   Q   P   R   T   Q   T   S   S   P   Y   A   G   P   V   G   L   C   C   S   S   C   F   L   .
376  AGTGCTTCAGCCTCG AACACAAACCTCCTC CCCATACGCTGGGCC AGTAGGTCTTTGCTG CAGCAGCTGCTTCCT
     TCACGAAGTCGGAGC TTGTGTTTGGAGGAG GGGTATGCGACCCGG TCATCCAGAAACGAC GTCGTCGACGAAGGA

C   T   Q   P   P   T   C   M   L   P   L   C   V   G   E   V   T   L   L   I   Y   S   L   E   G   .
451  CTGCACACAGCCCCC AACATGCATGCTTCC TCTGTGTGTTGGGGA GGTCACTCTCTTGAT TTATTCGTTGGAGGG
     GACGTGTGTCGGGGG TTGTACGTACGAAGG AGACACACAACCCCT CCAGTGAGAGAACTA AATAAGCAACCTCCC

L   Q   G   P   G   L   N   *
526  TTTGCAGGGCCCAGG ATTAAATTAAGAGAC TTGACTTTGCTGGA TCTCTTTTTGTAGAA GATTATTAAAGCAAA
     AAACGTCCCGGGTCC TAATTTAATTCTCTG AACTGAAAACGACCT AGAGAAAAACATCTT CTAATAATTTCGTTT

601  ATGTTGTAAAGATCC CTTAGAGACATTGTC AGGAGTTTTTGTGTT ACAGAACCTGCATG TTTCACATGGACACA
     TACAACATTTCTAGG GAATCTCTGTAACAG TCCTCAAAAAACACAA TGTCCTTGGACGTAC AAAGTGTACCTGTGT

676  TCACATGACCGAGCC AAATAGATTTATCTT TACTCT
     AGTGTACTGGCTCGG TTTATCTAAATAGAA ATGAGA
```

(SEQ ID NOS:11-12)

FIG. 4B

```
                                          1                                                        50
SEQ ID NO: 12   AJ004956_Vk_like   DIVMTQSPDS LAVSLGERAT INCKSSQSVL YSSNNKNYLA WYQQKPGQPP
SEQ ID NO: 13       V10577_Vk1-12  DIQMTQSPSS VSASVGDRVT ITCRASQGIS SW......LA WYQQKPGKAP
SEQ ID NO: 14       J00248_Vk1-16  DIQMTQSPSS LSASVGDRVT ITCRASQGIS NY......LA WFQQKPGKAP
SEQ ID NO: 15       X72808_Vk1-17  DIQMTQSPSS LSASVGDRVT ITCRASQGIR ND......LG WYQQKPGKAP
SEQ ID NO: 16       M64856_Vk1-33  DIQMTQSPSS LSASVGDRVT ITCQASQDIS NY......LN WYQQKPGKAP
SEQ ID NO: 17    HSIGKL22_Vk1-42   DIQMIQSPSF LSASVGDRVS IICWASEGIS SN......LA WYLQKPGKSP
SEQ ID NO: 18       X12691_Vk2D-28 DIVMTQSPLS LPVTPGEPAS ISCRSSQSLL HS.NGYNYLD WYLQKPGQSP
SEQ ID NO: 19       X63403_Vk2-30  DVVMTQSPLS LPVTLGQPAS ISCRSSQSLV YS.DGNTYLN WFQQRPGQSF
SEQ ID NO: 20    HSIGKLC1_Vk3-11   EIVLTQSPAT LSLSPGERAT LSCRASQSVS SY......LA WYQQKPGQAP
SEQ ID NO: 21       X17264_Vk3D-11 EIVLTQSPAT LSLSPGERAT LSCRASQGVS SY......LA WYQQKPGQAP
SEQ ID NO: 22       X02485_Vk5-2   ETTLTQSPAF MSATPGDKVN ISCKASQDID DD......MN WYQQKPGEAA
SEQ ID NO: 23       M27751_Vk6D-41 DVVMTQSPAF LSVTPGEKVT ITCQASEGIG NY......LY WYQQKPDQAP
SEQ ID NO: 24       X12682_Vk7-3   DIVLTQSPAS LAVSPGQRAT ITCRASESVS FL..GINLIH WYQQKPGQPP 51                                                       100
SEQ ID NO: 12   AJ004956_Vk_like   KLLIYWASTR ESGVPDRFSG SGSGTDFTLT ISSLQAEDVA VYYCQQYYST
SEQ ID NO: 13       V10577_Vk1-12  KLLIYAASSL QSGVPSRFSG SGSGTDFTLT ISSLQPEDFA TYYCQQANSF
SEQ ID NO: 14       J00248_Vk1-16  KSLIYAASSL QSGVPSRFSG SGSGTDFTLT ISSLQPEDFA TYYCQQYNSY
SEQ ID NO: 15       X72808_Vk1-17  KRLIYAASSL QSGVPSRFSG SGSGTEFTLT ISSLQPEDFA TYYCLQHNSY
SEQ ID NO: 16       M64856_Vk1-33  KLLIYDASNL ETGVPSRFSG SGSGTDFTFT ISSLQPEDIA TYYCQQYDNL
SEQ ID NO: 17    HSIGKL22_Vk1-42   KLFLYDAKDL HPGVSSRFSG RGSGTDFTLT IISLKPEDFA AYYCKQDFSY
SEQ ID NO: 18       X12691_Vk2D-28 QLLIYLGSNR ASGVPDRFSG SGSGTDFTLK ISRVEAEDVG VYYCMQALQT
SEQ ID NO: 19       X63403_Vk2-30  RRLIYKVSNR DSGVPDRFSG SGSGTDFTLK ISRVEAEDVG VYYCMQGTHW
SEQ ID NO: 20    HSIGKLC1_Vk3-11   RLLIYDASNR ATGIPARFSG SGSGTDFTLT ISSEEPEDFA VYYCQQRSNW
SEQ ID NO: 21       X17264_Vk3D-11 RLLIYDASNR ATGIPARFSG SGPGTDFTLT ISSLEPEDFA VYYCQQRSNW
SEQ ID NO: 22       X02485_Vk5-2   IFIIQEATTL VPGIPPRFSG SGYGTDFTLT INNIESEDAA YYFCLQHDNF
SEQ ID NO: 23       M27751_Vk6D-41 KLLIKYASQS ISGVPSRFSG SGSGTDFTFT ISSLEAEDAA TYYCQQGNKH
SEQ ID NO: 24       X12682_Vk7-3   KLLIYQASNK DTGVPARFSG SGSGTDFTLT INPVEANDTA NYYCLQSKNF 101                                                      150
SEQ ID NO: 12   AJ004956_Vk_like   PPTVLQPRTQ TSSPYAGPVG LCCSSCFLCT QPPTCMLPLC VGEVTLLIYS
SEQ ID NO: 13       V10577_Vk1-12  PPTVLPTRT. .......... .......... .......... ..........
SEQ ID NO: 14       J00248_Vk1-16  PPTVLHTQT. .......... .......... .......... ..........
SEQ ID NO: 15       X72808_Vk1-17  PPTVLHTRTT PREADV.... .......... .......... ..........
SEQ ID NO: 16       M64856_Vk1-33  PPTV...... .......... .......... .......... ..........
SEQ ID NO: 17    HSIGKL22_Vk1-42   PPTGLQA... .......... .......... .......... ..........
SEQ ID NO: 18       X12691_Vk2D-28 PPTVVQPLTE TSSWGCPVAH MCCLSGENES RVSESA.... ..........
SEQ ID NO: 19       X63403_Vk2-30  PPTVVQP... .......... .......... .......... ..........
SEQ ID NO: 20    HSIGKLC1_Vk3-11   PPTVIPHETK TPTRPSVFTR LLYQLLPEQT ASGVATQC.. ..........
SEQ ID NO: 21       X17264_Vk3D-11 HPTVIPHETK TPTRPSVFTR LLYQ...... .......... ..........
SEQ ID NO: 22       X02485_Vk5-2   PLTVIHPVQK PPSSLSGIAS A......... .......... ..........
SEQ ID NO: 23       M27751_Vk6D-41 PHTVLQPKTK ISSAWRNRET EQYPVFMILA GAVGEIIYQI PSHMAHSAEL
SEQ ID NO: 24       X12682_Vk7-3   PPTVL..... .......... .......... .......... ..........

151        164
SEQ ID NO: 12   AJ004956_Vk_like   LEGLQGPGLN ....
SEQ ID NO: 13       V10577_Vk1-12  .......... ....
SEQ ID NO: 14       J00248_Vk1-16  .......... ....
SEQ ID NO: 15       X72808_Vk1-17  .......... ....
SEQ ID NO: 16       M64856_Vk1-33  .......... ....
SEQ ID NO: 17    HSIGKL22_Vk1-42   .......... ....
SEQ ID NO: 18       X12691_Vk2D-28 .......... ....
SEQ ID NO: 19       X63403_Vk2-30  .......... ....
SEQ ID NO: 20    HSIGKLC1_Vk3-11   .......... ....
SEQ ID NO: 21       X17264_Vk3D-11 .......... ....
SEQ ID NO: 22       X02485_Vk5-2   .......... ....
SEQ ID NO: 23       M27751_Vk6D-41 TPKSQCLTLS SLPT
SEQ ID NO: 24       X12682_Vk7-3   .......... ....
```

FIG. 5A

```
     V   R   R   V   F   V   Q   Q   D   N   G   E   L   T   L   W   T   F   G
  1  GTGAGAAGGG TTTTGTTCA GCAAGACAAT GGAGAGCTCA CACTGTGGTG GACGTTCGGC
     CACTCTTCCC AAAAACAAGT CGTTCTGTTA CCTCTCGAGT GTGACACCAC CTGCAAGCCG

Q   G   T   K   V   E   I   K   R   T   V   A   A   P   S   V   F   I   F   P
 61  CAAGGGACCA AGTGGAAAT CAAACGAACT GTGGCTGCAC CATCTGTCTT CATCTTCCCG
     GTTCCCTGGT TCCACCTTTA GTTTGCTTGA CACCGACGTG GTAGACAGAA GTAGAAGGGC

P   S   D   E   Q   L   K   S   G   T   A   S   V   V   C   L   L   N   N   F
121  CCATCTGATG AGCAGTTGAA ATCTGGAACT GCCTCTGTTG TGTGCCTGCT GAATAACTTC
     GGTAGACTAC TCGTCAACTT TAGACCTTGA CGGAGACAAC ACACGGACGA CTTATTGAAG

Y   P   R   E   A   K   V   Q   W   K   V   D   N   A   L   Q   S   G   N   S
181  TATCCCAGAG AGGCCAAAGT ACAGTGGAAG GTGGATAACG CCCTCCAATC GGGTAACTCC
     ATAGGGTCTC TCCGGTTTCA TGTCACCTTC CACCTATTGC GGGAGTTAG CCCATTGAGG

Q   E   S   V   T   E   Q   D   S   K   D   S   T   Y   S   L   S   S   T   L
241  CAGGAGAGTG TCACAGAGCA GGACAGCAAG GACAGCACCT ACAGCCTCAG CAGCACCCTG
     GTCCTCTCAC AGTGTCTCGT CCTGTCGTTC CTGTCGTGGA TGTCGGAGTC GTCGTGGGAC

T   L   S   K   A   D   Y   E   K   H   K   L   Y   A   C   E   V   T   H   Q
301  ACGCTGAGCA AAGCAGACTA CGAGAAACAC AAACTCTACG CCTGCGAAGT CACCCATCAG
     TGCGACTCGT TTCGTCTGAT GCTCTTTGTG TTTGAGATGC GGACGCTTCA GTGGGTAGTC

G   L   S   S   P   V   T   K   S   F   N   R   G   E   C   *
361  GGCCTGAGCT CGCCCGTCAC AAAGAGCTTC AACAGGGGAG AGTGTTAG
     CCGGACTCGA GCGGGCAGTG TTTCTCGAAG TTGTCCCCTC TCACAATC
```

(SEQ ID NOS:25-26)

FIG. 5B

```
                              1                                                          50
SEQ ID NO: 27    J-Ck1    WTFGQGTKVE  IKRTVAAPSV  FIFPPSDEQL  KSGTASVVCL  LNNFYPREAK
SEQ ID NO: 28    J-Ck2    YTFGQGTKLE  IKRTVAAPSV  FIFPPSDEQL  KSGTASVVCL  LNNFYPREAK
SEQ ID NO: 29    J-Ck3    FTFGPGTKVD  IKRTVAAPSV  FIFPPSDEQL  KSGTASVVCL  LNNFYPREAK
SEQ ID NO: 30    J-Ck4    LTFGGGTKVE  IKRTVAAPSV  FIFPPSDEQL  KSGTASVVCL  LNNFYPREAK
SEQ ID NO: 31    J-Ck5    ITFGQGTRLE  IKRTVAAPSV  FIFPPSDEQL  KSGTASVVCL  LNNFYPREAK 51                                                         100
SEQ ID NO: 27    J-Ck1    VQWKVDNALQ  SGNSQESVTE  QDSKDSTYSL  SSTLTLSKAD  YEKHKLYACE
SEQ ID NO: 28    J-Ck2    VQWKVDNALQ  SGNSQESVTE  QDSKDSTYSL  SSTLTLSKAD  YEKHKLYACE
SEQ ID NO: 29    J-Ck3    VQWKVDNALQ  SGNSQESVTE  QDSKDSTYSL  SSTLTLSKAD  YEKHKLYACE
SEQ ID NO: 30    J-Ck4    VQWKVDNALQ  SGNSQESVTE  QDSKDSTYSL  SSTLTLSKAD  YEKHKLYACE
SEQ ID NO: 31    J-Ck5    VQWKVDNALQ  SGNSQESVTE  QDSKDSTYSL  SSTLTLSKAD  YEKHKLYACE 101                   119
SEQ ID NO: 27    J-Ck1    VTHQGLSSPV  TKSFNRGEC
SEQ ID NO: 28    J-Ck2    VTHQGLSSPV  TKSFNRGEC
SEQ ID NO: 29    J-Ck3    VTHQGLSSPV  TKSFNRGEC
SEQ ID NO: 30    J-Ck4    VTHQGLSSPV  TKSFNRGEC
SEQ ID NO: 31    J-Ck5    VTHQGLSSPV  TKSFNRGEC
```

FIG. 5C (SEQ ID NO: 32)

METDTLLLWVLLLWVPGSTGVRRVFVQQDNGELTLMWTFGQGTKVEIKRTVAAPSVFIFPPSDEQLK
SGTASVVCLLNNFYPREAKVQWKVDNALQGNSQESVTEQDSKDSTYSLSSTLTLSKADYEKHKLYAC
EVTHQGLSSPVTKSFNRGEC (SEQ ID NO: 33)

METDTLLLWVLLLWVPGSTGWTFGQGTKVEIKRTVAAPSVFIFPPSDEQLKSGTASVVCLLNNFYPR
EAKVQWKVDNALQGNSQESVTEQDSKDSTYSLSSTLTLSKADYEKHKLYACEVTHQGLSSPVTKSFN
RGEC (SEQ ID NO: 34)

METDTLLLWVLLLWVPGSTGTKVEIKRTVAAPSVFIFPPSDEQLKSGTASVVCLLNNFYPREAKVQW
KVDNALQGNSQESVTEQDSKDSTYSLSSTLTLSKADYEKHKLYACEVTHQGLSSPVTKSFNRGEC

FIG. 6A

| | | | 1 | | | 50 |
|---|---|---|---|---|---|---|
| SEQ ID NO: 36 | 2462VpreBlam5E07.fasta.Contig1 | (1) | ALDIQLTQSPSFLSASVGDRVTITCR---ASQGINTWLAWYQQKPGKAPK |
| SEQ ID NO: 37 | 2462VpreBlam5C04.fasta.Contig1 | (1) | ALDIQLTQSPSFLSASVGDRVTITCR---ASQGISTDLAWYQQKPGKAPK |
| SEQ ID NO: 38 | 2462VpreBlam5B09.fasta.Contig1 | (1) | ALEIVLTQSPGTLSLSPGERATLSCR---ASQSVSSSYLAWYQQKPGQAPR |
| SEQ ID NO: 39 | 2463VpreBlam5B05.fasta.Contig1 | (1) | ALDIQMTQSPSSLSASVGDRVTITCR---ASQGISNYLAWFQQKPGKAPK |
| SEQ ID NO: 40 | 2463VpreBlam5D07.fasta.Contig1 | (1) | ALDIQMTQSPSSLSASVGDRVTITCR---ASQGISNYLAWFQQKPGKAPK |
| SEQ ID NO: 41 | 2460VpreBlam5D10.fasta.Contig1 | (1) | ALDIQLTQSPSFLSASVGDRVTITCR---ASQGIGNDLNWYQQKPGKAPK |
| SEQ ID NO: 42 | 2460VpreBlam5B04.fasta.Contig1 | (1) | ALDIQLTQSPSFLSASVGDRVTITCR---ASQGISTDLNWYQQKPGKAPK |
| SEQ ID NO: 43 | 2460VpreBlam5A07.fasta.Contig1 | (1) | ALDIQLTQSPSFLSASVGDRVTITCR---ASQGIGNDLNWYQQKPGKAPK |
| SEQ ID NO: 44 | 2460VpreBlam5E01.fasta.Contig1 | (1) | ALDIQLTQSPSFLSASVGDRVTITCR---ASQGISSYLAWYQQKPGKAPK |
| SEQ ID NO: 45 | 2462VpreBlam5D05.fasta.Contig1 | (1) | ALCSALTQPAS-VSGSPGQSITISCTGTSSDVGGYNVSWYQQHPGKAPK |
| SEQ ID NO: 46 | 2462VpreBlam5A05.fasta.Contig1 | (1) | ALSYELMQPPS-VSVSPGQTARITCS---GDALPKQYAYWYQQKPGQAPV |
| SEQ ID NO: 47 | 2462VpreBlam5C09.fasta.Contig1 | (1) | AIQSALTQPAS-VSGSPGQSITISCTGTSSNVGGYNVSWYQQHPGKAPK |
| SEQ ID NO: 48 | 2460VpreBlam5F05.fasta.Contig1 | (1) | ALQSALTQPAS-VSGSPGQSITISCTGTSSDVGSYNVSWYQQHPGKAPK |
| SEQ ID NO: 49 | 2462VpreBlam5E08.fasta.Contig1 | (1) | ALSSELTQDPA-VSVALGQTVRITCQG---DSLRKKYVWYQQKPGQAPV |
| SEQ ID NO: 50 | 2462VpreBlam5C05.fasta.Contig1 | (1) | ALQSALTQPAS-VSGSPGQSITISCTGTSSDVGGYNVSWYQQHPGKAPK |
| SEQ ID NO: 51 | 2463VpreBlam5C04.fasta.Contig1 | (1) | ALQSALTQPAS-VSGSPGQSITISCTGTSSDVGGYNVSWYQQHPGKAPK |

| | | | 51 | | | 100 |
|---|---|---|---|---|---|---|
| SEQ ID NO: 36 | 2462VpreBlam5E07.fasta.Contig1 | (48) | LLIYAASTLQSGVPSRFSGSGSGTEFTLTISSLQPEDFATYYCQQLNS-- |
| SEQ ID NO: 37 | 2462VpreBlam5C04.fasta.Contig1 | (48) | LLIYDASSLESGVPSRFSGSGSGTEFTLTISSLQPEDFATYYCQQANS-- |
| SEQ ID NO: 38 | 2462VpreBlam5B09.fasta.Contig1 | (49) | LLIYGASSRATGIPDRFSGSGSGTDFTLTISRLEPEDFAVYYCQQYGN-- |
| SEQ ID NO: 39 | 2463VpreBlam5B05.fasta.Contig1 | (48) | SLIYAASLQSGVPSRFSGSGSGTDFTLTISSLQPEDFATYYCQQYNS-- |
| SEQ ID NO: 40 | 2463VpreBlam5D07.fasta.Contig1 | (48) | SLIYAASTLESGVPSRFSGSGSGTDFTLTISSLQPEDFATYYCQQYNS-- |
| SEQ ID NO: 41 | 2460VpreBlam5D10.fasta.Contig1 | (48) | LLIYDASLESGVPSRFSGSGSGTEFTLTISSLQPEDFATYYCQQADS-- |
| SEQ ID NO: 42 | 2460VpreBlam5B04.fasta.Contig1 | (48) | LLIYAAGNLESGVPSRFSGSGGGTEFTLTISSLQPEDFATYYCQQSYN-- |
| SEQ ID NO: 43 | 2460VpreBlam5A07.fasta.Contig1 | (48) | LLIYDASSLESGVPSRFSGSGSGTEFTLTISSLQPEDFATYYCQQADS-- |
| SEQ ID NO: 44 | 2460VpreBlam5E01.fasta.Contig1 | (48) | LLIYAASTLQSGVPSRFSGSGSGTEFTLTISSLQPEDFATYYCQQLNS-- |
| SEQ ID NO: 45 | 2462VpreBlam5D05.fasta.Contig1 | (50) | LIIYDVTKRPSGVSNRFSGSKSGNTASLTISGLQAEDEADYCCSYTG-T |
| SEQ ID NO: 46 | 2462VpreBlam5A05.fasta.Contig1 | (50) | LVIYKDSERPSGIPERFSGSSSGTTVTLTISGVQAEDEADYCQSADSSG |
| SEQ ID NO: 47 | 2462VpreBlam5C09.fasta.Contig1 | (50) | LMIEVSNRPSGVSNRFSGSKSGNTASLTISGLQAEDEADYCCSYTS-T |
| SEQ ID NO: 48 | 2460VpreBlam5F05.fasta.Contig1 | (50) | LIIYEVSKRPSGVSNRFSGSKSGNTASLTISGLQAEDEADYCCSSYAG-T |
| SEQ ID NO: 49 | 2462VpreBlam5E08.fasta.Contig1 | (47) | LVIYKDNNRPSGIPDRFSGSSSGNTASLTTTGAQAEDEADYCNSWDSSS |
| SEQ ID NO: 50 | 2462VpreBlam5C05.fasta.Contig1 | (50) | LMIYEVTNRPSGVSNRFSGSKSGNTASLTISGLQAEDEADYCCSYAGS- |
| SEQ ID NO: 51 | 2463VpreBlam5C04.fasta.Contig1 | (50) | LIIYDVTNRPSGVSNRFSGSKSGNTASLTISGLQAEDEADYCCSSYTG-S |

FIG. 6B

```
                                                    101                                                  150
SEQ ID NO: 36  2462VpreB1am5E07.fasta.Contig1  ( 96) YPLTFGGGTKVEIKR-TVAAPSVFIFPPSDEQLKSGTASVVCLLNNFYPR
SEQ ID NO: 37  2462VpreB1am5C04.fasta.Contig1  ( 96) FPFTFGGGTKVEIKR-TVAAPSVFIFPPSDEQLKSGTASVVCLLNNFYPR
SEQ ID NO: 38  2462VpreB1am5B09.fasta.Contig1  ( 97) SPRTFGGGTKVEIKR-TVAAPSVFIFPPSDEQLKSGTASVVCLLNNFYPR
SEQ ID NO: 39  2463VpreB1am5B05.fasta.Contig1  ( 96) YPLTFGGGTKVEIKR-TVAAPSVFIFPPSDEQLKSGTASVVCLLNNFYPR
SEQ ID NO: 40  2463VpreB1am5D07.fasta.Contig1  ( 96) YPLTFGGGTKVEIKR-TVAAPSVFIFPPSDEQLKSGTASVVCLLNNFYPR
SEQ ID NO: 41  2460VpreB1am5D10.fasta.Contig1  ( 96) WPLTFGGGTKVEIKR-TVAAPSVFIFPPSDEQLKSGTASVVCLLNNFYPR
SEQ ID NO: 42  2460VpreB1am5B04.fasta.Contig1  ( 96) WPYFGGGTKVEIKR-TVAAPSVFIFPPSDEQLKSGTASVVCLLNNFYPR
SEQ ID NO: 43  2462VpreB1am5A07.fasta.Contig1  ( 96) WPLTFGGGTKVEIKR-TVAAPSVFIFPPSDEQLKSGTASVVCLLNNFYPR
SEQ ID NO: 44  2462VpreB1am5E01.fasta.Contig1  ( 96) YPLTFGGGTKVEIKR-TVAAPSVFIFPPSDEQLKSGTASVVCLLNNFYPR
SEQ ID NO: 45  2462VpreB1am5D05.fasta.Contig1  ( 99) SNFVFGGGTKLTVLRQPKAAPSVTLFPPSSEELQANKATLVCLISDFYPG
SEQ ID NO: 46  2462VpreB1am5A05.fasta.Contig1  ( 97) TYVFGGGTKLTVLRQPKAAPSVTLFPPSSEELQANKATLVCLISDFYPG
SEQ ID NO: 47  2462VpreB1am5C09.fasta.Contig1  ( 99) SNVVFGGGTKLTV.RQPKAAPSVTLFPPSSEELQANKATLVCLISDFYPG
SEQ ID NO: 48  2462VpreB1am5F05.fasta.Contig1  ( 99) SNVVFGGGTKLTV.RQPKAAPSVTLFPPSSEELQANKATLVCLISDFYPG
SEQ ID NO: 49  2462VpreB1am5E08.fasta.Contig1  ( 97) AHYVFGGGTKLTV.RQPKAAPSVTLFPPSSEELQANKATLVCLISDFYPG
SEQ ID NO: 50  2462VpreB1am5C05.fasta.Contig1  ( 99) SNLVFGGGTKLTV.RQPKAAPSVTLFPPSSEELQANKATLVCLISDFYPG
SEQ ID NO: 51  2463VpreB1am5C04.fasta.Contig1  ( 99) SSYVFGGGTKLTV.RQPKAAPSVTLFPPSSEELQANKATLVCLISDFYPG 151                                                  200
SEQ ID NO: 36  2462VpreB1am5E07.fasta.Contig1  (145) EAKVQWKVDNALQSGNSQESVTEQDSKDSTYSLSSTLTLSKADYEKHKVY
SEQ ID NO: 37  2462VpreB1am5C04.fasta.Contig1  (145) EAKVQWKVDNALQSGNSQESVTEQDSKDSTYSLSSTLTLSKADYEKHKVY
SEQ ID NO: 38  2462VpreB1am5B09.fasta.Contig1  (146) EAKVQWKVDNALQRGNSQESVTEQDSKDSTYSLSSTLTLSKADYEKHKVY
SEQ ID NO: 39  2463VpreB1am5B05.fasta.Contig1  (145) EAKVQWKVDNALQSGNSQESVTEQDSKDSTYS.SSTLTLSKADYEKHKVY
SEQ ID NO: 40  2463VpreB1am5D07.fasta.Contig1  (145) EAKVQWKVDNALQSGNSQESVTEQDSKDSTYSLSSTLTLSKADYEKHKVY
SEQ ID NO: 41  2460VpreB1am5D10.fasta.Contig1  (145) EAKVQWKVDNALQSGNSQESVTEQDSKDSTYSLSSTLTLSKADYEKHKVY
SEQ ID NO: 42  2460VpreB1am5B04.fasta.Contig1  (145) EAKVQWKVDNALQSGNSQESVTEQDSKDSTYSLSSTLTLSKADYEKHKVY
SEQ ID NO: 43  2462VpreB1am5A07.fasta.Contig1  (145) EAKVQWKVDNALQSGNSQESVTEQDSKDSTYSLSSTLTLSKADYEKHKVY
SEQ ID NO: 44  2462VpreB1am5E01.fasta.Contig1  (145) EAKVQWKVDNALQSGNSQESVTEQDSKDSTYSLSSTLTLSKADYEKHKVY
SEQ ID NO: 45  2462VpreB1am5D05.fasta.Contig1  (149) AVTVAWKADGSPVKAG-VETTTPSKQSNNKYAASSYLSLTPEQWKSHKSY
SEQ ID NO: 46  2462VpreB1am5A05.fasta.Contig1  (147) AVTVAWKADGSPVKAG-VETTTPSKQSNNKYAASSYLSLTPEQWKSHKSY
SEQ ID NO: 47  2462VpreB1am5C09.fasta.Contig1  (149) AVTVAWKADGSPVKAG-VETTTPSKQSNNKYAASSYLSLTPEQWKSHKSY
SEQ ID NO: 48  2462VpreB1am5F05.fasta.Contig1  (149) AVTVAWKADGSPVKAG-VETTTPSKQSNNKYAASSYLSLTPEQWKSEKSY
SEQ ID NO: 49  2462VpreB1am5E08.fasta.Contig1  (147) AVTVAWKADGSPVKAG-VETTTPSKQSNNKYAASSYLSLTPEQWKSHKSY
SEQ ID NO: 50  2462VpreB1am5C05.fasta.Contig1  (149) AVTVAWKADGSPVKAG-VETTTPSKQSNNKYAASSYLSLTPEQWKSHKSY
SEQ ID NO: 51  2463VpreB1am5C04.fasta.Contig1  (149) AVTVAWKADGSPVKAG-VETTTPSKQSNNKYAASSYLSLTPEQWKSHKSY 201                            250
SEQ ID NO: 36  2462VpreB1am5E07.fasta.Contig1  (195) ACEVTHQGLSSPVTKSFNRGEC
SEQ ID NO: 37  2462VpreB1am5C04.fasta.Contig1  (195) ACEVTHQGLSSPVTKSFNRGEC
SEQ ID NO: 38  2462VpreB1am5B09.fasta.Contig1  (196) ACEVTHQGLSSPVTKSFNRGEC
SEQ ID NO: 39  2463VpreB1am5B05.fasta.Contig1  (195) ACFVTHQGLSSPVTKSFNRGFC
SEQ ID NO: 40  2463VpreB1am5D07.fasta.Contig1  (195) ACEVTHQGLSSPVTKSFNRGEC
SEQ ID NO: 41  2460VpreB1am5D10.fasta.Contig1  (195) ACEVTHQGLSSPVTKSFNRGEC
SEQ ID NO: 42  2460VpreB1am5B04.fasta.Contig1  (195) ACEVTHQGLSSPVTKSFNRGEC
SEQ ID NO: 43  2462VpreB1am5A07.fasta.Contig1  (195) ACEVTHQGLSSPVTKSFNRGEC
SEQ ID NO: 44  2462VpreB1am5E01.fasta.Contig1  (195) ACEVTHQGLSSPVTKSFNRGEC
SEQ ID NO: 45  2462VpreB1am5D05.fasta.Contig1  (198) SCQVTHEGSTVEKTVAPTECS
SEQ ID NO: 46  2462VpreB1am5A05.fasta.Contig1  (196) SCQVTHEGSTVEKTVAPTECS
SEQ ID NO: 47  2462VpreB1am5C09.fasta.Contig1  (198) SCQVTHEGSTVEKTVAPTECS
SEQ ID NO: 48  2462VpreB1am5F05.fasta.Contig1  (198) SCQVTHEGSTVEKTVAPTECS
SEQ ID NO: 49  2462VpreB1am5E08.fasta.Contig1  (196) SCQVTHEGSTVEKTVAPTECS
SEQ ID NO: 50  2462VpreB1am5C05.fasta.Contig1  (198) SCQVTHEGSTVEKTVAPTECS
SEQ ID NO: 51  2463VpreB1am5C04.fasta.Contig1  (198) SCQVTHEGSTVEKTVAPTECS
```

FIG. 7

| | | | |
|---|---|---|---|
| SEQ ID NO: 52 | 2462VpreB_am5E07.fasta.Contig1 | (1) | EVQLVESGGGLVKPGGSLRLSCAASGFTFSTYGMSWVRQAPGKGLEWVAY |
| SEQ ID NO: 53 | 2462VpreB_am5C04.fasta.Contig1 | (1) | EVQLLESGGGLVQPGGSLRLSCAASGFTFSSYAMSWVRQAPGKGLEWVSA |
| SEQ ID NO: 54 | 2462VpreB_am5B09.fasta.Contig1 | (1) | QVQLVQSGAEVKKPGASVKVSCKASGYTFTGYYMHWVRQAPGQGLEWMGG |
| SEQ ID NO: 55 | 2463VpreB_am5B05.fasta.Contig1 | (1) | QVQLVQSGAEVKKPGSSVKVSCKASGGTFTAYAINWVRQAPGQGLEWMGG |
| SEQ ID NO: 56 | 2463VpreB_am5D07.fasta.Contig1 | (1) | QVQLVQSGAEVKKPGASVKVSCKASGYTFSGYGMHWVRQAPGQGLEWMGW |
| SEQ ID NO: 57 | 2460VpreB_am5D10.fasta.Contig1 | (1) | EVQLVESGGGLVKPGGSLRLSCAASGFTFRSYEMHWVRQAPGKGLEWVAS |
| SEQ ID NO: 58 | 2460VpreB_am5B04.fasta.Contig1 | (1) | EVQLVESGGGLVKPGGSLRLSCAASGFTFSNFEMNWVRQAPGKGLEWVSG |
| SEQ ID NO: 59 | 2462VpreB_am5A07.fasta.Contig1 | (1) | EVQLVESGGGLVKPGGSLRLSCAASGFTFRSYEMHWVRQAPGKGLEWVAS |
| SEQ ID NO: 60 | 2460VpreB_am5E01.fasta.Contig1 | (1) | QVQLVQSGAEVKKPGASVKVSCKASGYTFSAHGLNWVRQAPGQGLEWMGW |
| SEQ ID NO: 61 | 2462VpreB_am5D05.fasta.Contig1 | (1) | QVQLVQSGAEVKKPGSSVKVSCKASGGTFSNYAISWVRQAPGQGLEWMGW |
| SEQ ID NO: 62 | 2462VpreB_am5A05.fasta.Contig1 | (1) | QVQLVQSGAEVKKPGASVKVSCKASGYTFTGYYMHWVRQAPGQGLEWMGW |
| SEQ ID NO: 63 | 2462VpreB_am5C09.fasta.Contig1 | (1) | EVQLLESGGGLVQPGGSLRLSCAASGFTFSNYGMNWVRQAPGKGLEWVAN |
| SEQ ID NO: 64 | 2460VpreB_am5F05.fasta.Contig1 | (1) | EVQLLESGGGLVQPGGSLRLSCAASGFTFSSYAMNWVRQAPGKGLEWVSV |
| SEQ ID NO: 65 | 2462VpreB_am5E08.fasta.Contig1 | (1) | EVQLLESGGGLVQPGGSLRLSCAASGFTFSSYGMNWVRQAPGKGLEWVAT |
| SEQ ID NO: 66 | 2462VpreB_am5C05.fasta.Contig1 | (1) | EVQLVESGGGLVKPGGSLRLSCAASGFTFSDYGMSWVRQAPGKGLEWVSG |
| SEQ ID NO: 67 | 2463VpreB_am5C04.fasta.Contig1 | (1) | QVQLVQSGAEVKKPGASVKVSCKASGYTFSSYGMSWVRQAPGQGLEWMGW |
| | | | |
| SEQ ID NO: 52 | 2462VpreB_am5E07.fasta.Contig1 | (51) | INNGSGYIYYADSVKGRFTISRDNAKNSLYLQMNSLRAEDTAVYYCARGQ |
| SEQ ID NO: 53 | 2462VpreB_am5C04.fasta.Contig1 | (51) | ISGSGGSTYYADSVKGRFTISRDNSKNTLYIQMNSLRAEDTAVYYCARGY |
| SEQ ID NO: 54 | 2462VpreB_am5B09.fasta.Contig1 | (51) | INFNSGGTNYAQKFQGRVTMTRDTSISTAYMELSRLRSDDTAVYYCARRP |
| SEQ ID NO: 55 | 2463VpreB_am5B05.fasta.Contig1 | (51) | INVGFGGANYAQKFQGRVTITADKSTSTAYMELSSLRSEDTAVYYCARDD |
| SEQ ID NO: 56 | 2463VpreB_am5D07.fasta.Contig1 | (51) | INPISGTATYAQKFQGRVTMTRDTSISTAYMELSRLRSDDTAVYYCAKDL |
| SEQ ID NO: 57 | 2460VpreB_am5D10.fasta.Contig1 | (51) | IKYDGANKNYADSVKGRFTISRDNAKNSLYLQMNSLRAEDTAVYYCARAS |
| SEQ ID NO: 58 | 2460VpreB_am5B04.fasta.Contig1 | (51) | ISSNGRYINYADSVKGRFTISRDNAKNSLYLQMNSLRAEDTAVYYCARVV |
| SEQ ID NO: 59 | 2462VpreB_am5A07.fasta.Contig1 | (51) | IKYDGANKNYADSVKGRFTISRDNAKNSLYLQMNSLRAEDTAVYYCARAS |
| SEQ ID NO: 60 | 2460VpreB_am5E01.fasta.Contig1 | (51) | INFITGTATYAQKFQGRVTMTRDTSISTAYMELSRLRSDDTAVYYCARGG |
| SEQ ID NO: 61 | 2462VpreB_am5D05.fasta.Contig1 | (51) | ISPFSGGTNYAQKFQGRVTITADKSTSTAYMELSSLRSEDTAVYYCARGQ |
| SEQ ID NO: 62 | 2462VpreB_am5A05.fasta.Contig1 | (51) | INFNSGGTNYAQKFQGRVTMTRDTSISTAYMELSRLRSDDTAVYYCARGP |
| SEQ ID NO: 63 | 2462VpreB_am5C09.fasta.Contig1 | (51) | IGYGGTNTYYADSVKGRFTISRDNSKNTLYLQMNSLRAEDTAVYYCAREA |
| SEQ ID NO: 64 | 2460VpreB_am5F05.fasta.Contig1 | (51) | ISGNSADKNYADSVKGRFTISRDNSKNTLYLQMNSLRAEDTAVYYCARGD |
| SEQ ID NO: 65 | 2462VpreB_am5E08.fasta.Contig1 | (51) | INYSGTSKYYADSVKGRFTISRDNSKNTLYLQMNSLRAEDTAVYYCARDR |
| SEQ ID NO: 66 | 2462VpreB_am5C05.fasta.Contig1 | (51) | ISWNGGTTNYADSVKGRFTISRDNAKNSLYLQMNSLRAEDTAVYYCARSG |
| SEQ ID NO: 67 | 2463VpreB_am5C04.fasta.Contig1 | (51) | INANSGGTSYAQKFQGRVTMTRDTSISTAYMELSRLRSDDTAVYYCARDD |
| | | | |
| SEQ ID NO: 52 | 2462VpreB_am5E07.fasta.Contig1 | (101) | WWSG----GDFDYWGQGTLVTVSSASTKGPSVFPLAPSSKSTS......... |
| SEQ ID NO: 53 | 2462VpreB_am5C04.fasta.Contig1 | (101) | RASDSDYYGWMDYWGQGTLVTVSSASTKGPSVFPLAPSSKSTS......... |
| SEQ ID NO: 54 | 2462VpreB_am5B09.fasta.Contig1 | (101) | AG------PWALDYWGQGTLVTVSSASTKGPSVFPLAPSSKSTS......... |
| SEQ ID NO: 55 | 2463VpreB_am5B05.fasta.Contig1 | (101) | Y-------WTSVYWGQGTLVTVSSASTKGPSVFPLAPSSKSTS......... |
| SEQ ID NO: 56 | 2463VpreB_am5D07.fasta.Contig1 | (101) | IGWI-SHSYNGDYWGQGTLVTVSSASTKGPSVFPLAPSSKSTS......... |
| SEQ ID NO: 57 | 2460VpreB_am5D10.fasta.Contig1 | (101) | PYG-----PSFDYWGQGTLVTVSSASTKGPSVFPLAPSSKSTS......... |
| SEQ ID NO: 58 | 2460VpreB_am5B04.fasta.Contig1 | (101) | DFDQDYN--GFDYWGQGTLVTVSSASTKGPSVFPLAPSSKSTS......... |
| SEQ ID NO: 59 | 2462VpreB_am5A07.fasta.Contig1 | (101) | PYGP-----SFDYWGQGTLVTVSSASTKGPSVFPLAPSSKSTS......... |
| SEQ ID NO: 60 | 2460VpreB_am5E01.fasta.Contig1 | (101) | WSN-----WGFDYWGQGTLVTVSSASTKGPSVFPLAPSSKSTS......... |
| SEQ ID NO: 61 | 2462VpreB_am5D05.fasta.Contig1 | (101) | WWYG----DAFDYWGQGTLVTVSSASTKGPSVFPLAPSSKSTS......... |
| SEQ ID NO: 62 | 2462VpreB_am5A05.fasta.Contig1 | (101) | IRSRGGK-YGGDYWGQGTLVTVSSASTKGPSVFPLAPSSKSTS......... |
| SEQ ID NO: 63 | 2462VpreB_am5C09.fasta.Contig1 | (101) | GYDR--YGYGFDYWGQGTLVTVSSASTKGPSVFPLAPSSKSTS......... |
| SEQ ID NO: 64 | 2460VpreB_am5F05.fasta.Contig1 | (101) | GLN------YLDYWGQGTLVTVSSASTKGPSVFPLAPSSKSTS......... |
| SEQ ID NO: 65 | 2462VpreB_am5E08.fasta.Contig1 | (101) | YKS---YTYALDYWGQGTLVTVSSASTKGPSVFPLAPSSKSTS......... |
| SEQ ID NO: 66 | 2462VpreB_am5C05.fasta.Contig1 | (101) | G---AFYLSGLDYWGQGTLVTVSSASTKGPSVFPLAPSSKSTS......... |
| SEQ ID NO: 67 | 2463VpreB_am5C04.fasta.Contig1 | (101) | G-------GAYVYWGQGTLVTVSSASTKGPSVFPLAPSSKSTS......... |

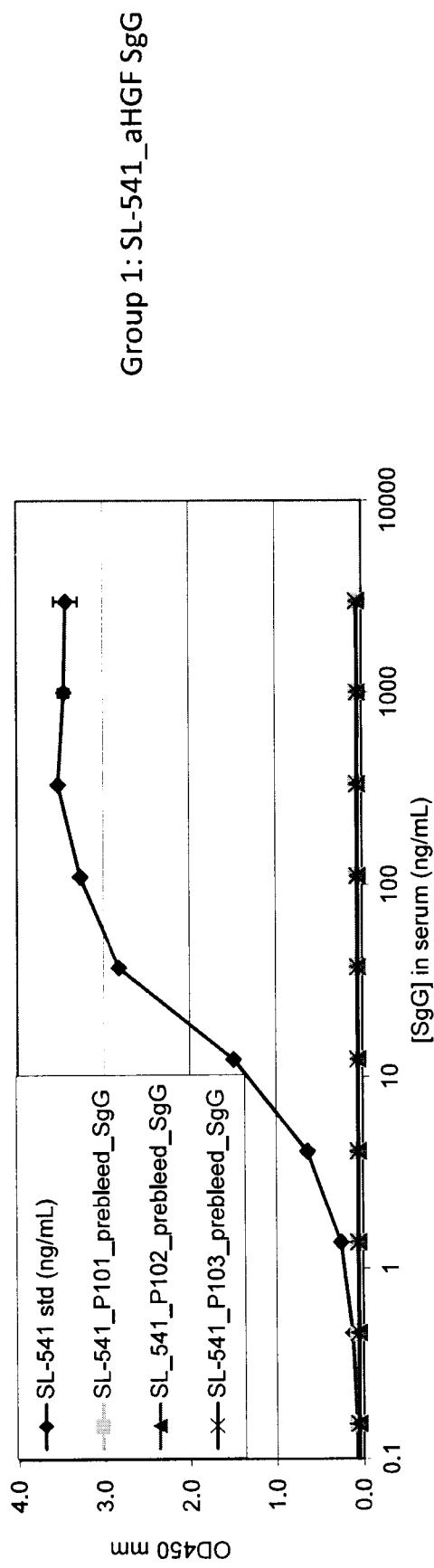
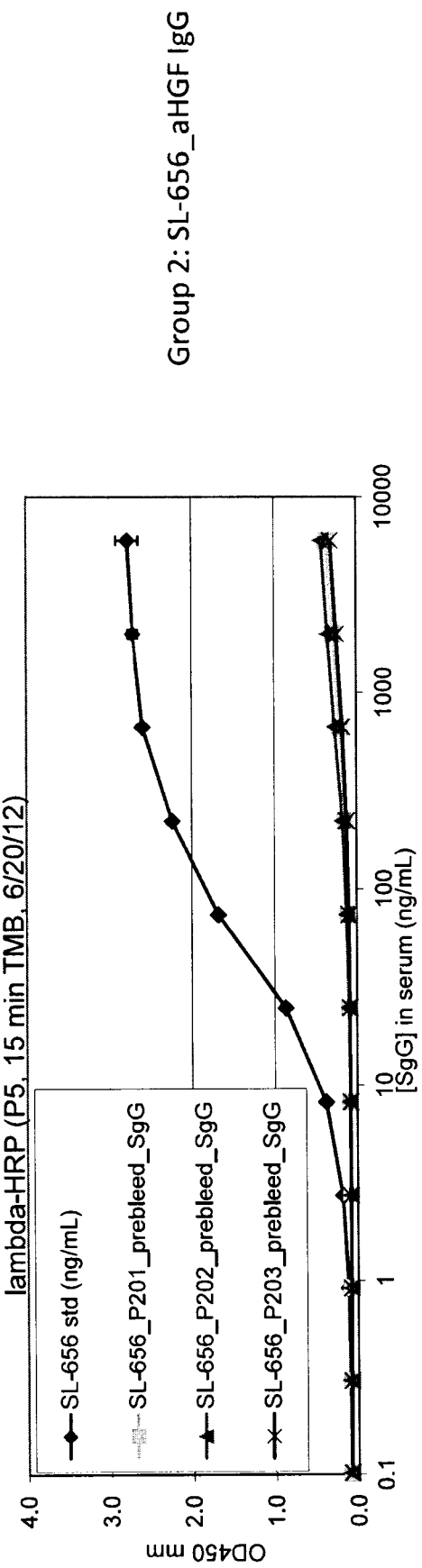
FIG. 17A

FIG. 23

Surrobody™ (e.g., surrogate light chain construct) Test Articles Used in Cynomolgus Monkey PK Study

| SL No. | Target | SgG Format | SgG Structure |
|---|---|---|---|
| SL-349 | HGF/PlGF | SgG1_SVD (Stacked Variable Domain) | |
| SL-521 | HGF/PlGF | SgG1_Ball/Socket | |
| SL-541 | HGF | SgG1 | |
| SL-542 | PlGF | SgG1 | |
| SL-656 | HGF | IgG1 | |

SEQUENCE LISTING

```
<160> NUMBER OF SEQ ID NOS: 67

<210> SEQ ID NO 1
<211> LENGTH: 145
<212> TYPE: PRT
<213> ORGANISM: Homo sapiens

<400> SEQUENCE: 1

Met Ser Trp Ala Pro Val Leu Leu Met Leu Phe Val Tyr Cys Thr Gly
1               5                   10                  15

Cys Gly Pro Gln Pro Val Leu His Gln Pro Pro Ala Met Ser Ser Ala
            20                  25                  30

Leu Gly Thr Thr Ile Arg Leu Thr Cys Thr Leu Arg Asn Asp His Asp
        35                  40                  45

Ile Gly Val Tyr Ser Val Tyr Trp Tyr Gln Gln Arg Pro Gly His Pro
    50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
            100                 105                 110

Tyr Tyr Cys Ala Met Gly Ala Arg Ser Ser Glu Lys Glu Glu Arg Glu
        115                 120                 125

Arg Glu Trp Glu Glu Glu Met Glu Pro Thr Ala Ala Arg Thr Arg Val
    130                 135                 140

Pro
145
```

<210> SEQ ID NO 2
<211> LENGTH: 142
<212> TYPE: PRT
<213> ORGANISM: Mus musculus

<400> SEQUENCE: 2

Met Ala Trp Thr Ser Val Leu Leu Met Leu Leu Ala His Leu Thr Gly
1               5                   10                  15

Cys Gly Pro Gln Pro Met Val His Gln Pro Ser Ala Ser Ser Ser
            20                  25                  30

Leu Gly Ala Thr Ile Arg Leu Ser Cys Thr Leu Ser Asn Asp His Asn
        35                  40                  45

Ile Gly Ile Tyr Ser Ile Tyr Trp Tyr Gln Gln Arg Pro Gly His Pro
    50                  55                  60

Pro Arg Phe Leu Leu Arg Tyr Phe Ser His Ser Asp Lys His Gln Gly
65                  70                  75                  80

Pro Asp Ile Pro Pro Arg Phe Ser Gly Ser Lys Asp Thr Ala Arg Asn
                85                  90                  95

Leu Gly Tyr Leu Ser Ile Ser Glu Leu Gln Pro Glu Asp Glu Ala Val
            100                 105                 110

Tyr Tyr Cys Ala Val Gly Leu Arg Ser His Glu Lys Lys Arg Met Glu
        115                 120                 125

Arg Glu Trp Glu Gly Glu Lys Ser Tyr Thr Asp Leu Gly Ser
    130                 135                 140

<210> SEQ ID NO 3
<211> LENGTH: 171
<212> TYPE: PRT
<213> ORGANISM: Mus musculus

<400> SEQUENCE: 3

Met Ala Trp Thr Ser Val Leu Leu Met Leu Leu Ala His Leu Thr Gly
1               5                   10                  15

Lys Gly Thr Leu Gly Val Gln Gly Phe Leu Ala Pro Pro Val Ala Leu
            20                  25                  30

Leu Cys Pro Ser Asp Gly His Ala Ser Ile Phe Ser Gly Cys Gly Pro
        35                  40                  45

Gln Pro Met Val His Gln Pro Pro Ser Ala Ser Ser Ser Leu Gly Ala
    50                  55                  60

Thr Ile Arg Leu Ser Cys Thr Leu Ser Asn Asp His Asn Ile Gly Ile
65                  70                  75                  80

Tyr Ser Ile Tyr Trp Tyr Gln Gln Arg Pro Gly His Pro Pro Arg Phe
                85                  90                  95

Leu Leu Arg Tyr Phe Ser His Ser Asp Lys His Gln Gly Pro Asp Ile
            100                 105                 110

Pro Pro Arg Phe Ser Gly Ser Lys Asp Thr Ala Arg Asn Leu Gly Tyr
        115                 120                 125

Leu Ser Ile Ser Glu Leu Gln Pro Glu Asp Glu Ala Val Tyr Tyr Cys
    130                 135                 140

Ala Val Gly Leu Arg Ser His Glu Lys Lys Arg Met Glu Arg Glu Trp
145                 150                 155                 160

Glu Gly Glu Lys Ser Tyr Thr Asp Leu Gly Ser
                165                 170

-continued

```
<210> SEQ ID NO 4
<211> LENGTH: 123
<212> TYPE: PRT
<213> ORGANISM: Homo sapiens

<400> SEQUENCE: 4

Met Ala Cys Arg Cys Leu Ser Phe Leu Leu Met Gly Thr Phe Leu Ser
1               5                   10                  15

Val Ser Gln Thr Val Leu Ala Gln Leu Asp Ala Leu Leu Val Phe Pro
            20                  25                  30

Gly Gln Val Ala Gln Leu Ser Cys Thr Leu Ser Pro Gln His Val Thr
        35                  40                  45

Ile Arg Asp Tyr Gly Val Ser Trp Tyr Gln Gln Arg Ala Gly Ser Ala
    50                  55                  60

Pro Arg Tyr Leu Leu Tyr Tyr Arg Ser Glu Glu Asp His His Arg Pro
65                  70                  75                  80

Ala Asp Ile Pro Asp Arg Phe Ser Ala Ala Lys Asp Glu Ala His Asn
                85                  90                  95

Ala Cys Val Leu Thr Ile Ser Pro Val Gln Pro Glu Asp Asp Ala Asp
            100                 105                 110

Tyr Tyr Cys Ser Val Gly Tyr Gly Phe Ser Pro
        115                 120

<210> SEQ ID NO 5
<211> LENGTH: 119
<212> TYPE: PRT
<213> ORGANISM: Homo sapiens

<400> SEQUENCE: 5

Met Ser Trp Ala Pro Val Leu Leu Met Leu Phe Val Tyr Cys Thr Gly
1               5                   10                  15

Cys Gly Pro Gln Pro Val Leu His Gln Pro Pro Ala Met Ser Ser Ala
            20                  25                  30

Leu Gly Thr Thr Ile Arg Leu Thr Cys Thr Leu Arg Asn Asp His Asp
        35                  40                  45

Ile Gly Val Tyr Ser Val Tyr Trp Tyr Gln Gln Arg Pro Gly His Pro
    50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
            100                 105                 110

Tyr Tyr Cys Ala Met Gly Ala
        115

<210> SEQ ID NO 6
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Glu Thr Asp Thr Leu Leu Leu Trp Val Leu Leu Leu Trp Val Pro
1               5                   10                  15

Gly Ser Thr Gly Gln Pro Val Leu His Gln Pro Pro Ala Met Ser Ser
            20                  25                  30
```

```
Ala Leu Gly Thr Thr Ile Arg Leu Thr Cys Thr Leu Arg Asn Asp His
         35                  40                  45

Asp Ile Gly Val Tyr Ser Val Tyr Trp Tyr Gln Gln Arg Pro Gly His
 50                  55                  60

Pro Pro Arg Phe Leu Leu Arg Tyr Phe Ser Gln Ser Asp Lys Ser Gln
 65                  70                  75                  80

Gly Pro Gln Val Pro Pro Arg Phe Ser Gly Ser Lys Asp Val Ala Arg
                 85                  90                  95

Asn Arg Gly Tyr Leu Ser Ile Ser Glu Leu Gln Pro Glu Asp Glu Ala
            100                 105                 110

Met Tyr Tyr Cys Ala Met Gly Ala Arg Ser Ser Glu Lys Glu Glu Arg
            115                 120                 125

Glu Arg Glu Trp Glu Glu Glu Met Glu Pro Thr Ala Ala Arg Thr Arg
130                 135                 140

Val Pro
145

<210> SEQ ID NO 7
<211> LENGTH: 209
<212> TYPE: PRT
<213> ORGANISM: Homo sapiens

<400> SEQUENCE: 7

Met Lys Leu Arg Val Gly Gln Thr Leu Gly Thr Ile Pro Arg Gln Cys
 1               5                  10                  15

Glu Val Leu Leu Leu Leu Leu Leu Gly Leu Val Asp Gly Val His
             20                  25                  30

His Ile Leu Ser Pro Ser Ser Ala Glu Arg Ser Arg Ala Val Gly Pro
         35                  40                  45

Gly Ala Ser Val Gly Ser Asn Arg Pro Ser Leu Trp Ala Leu Pro Gly
 50                  55                  60

Arg Leu Leu Phe Gln Ile Ile Pro Arg Gly Ala Gly Pro Arg Cys Ser
 65                  70                  75                  80

Pro His Arg Leu Pro Ser Lys Pro Gln Phe Trp Tyr Val Phe Gly Gly
                 85                  90                  95

Gly Thr Gln Leu Thr Ile Leu Gly Gln Pro Lys Ser Ala Pro Leu Val
            100                 105                 110

Thr Leu Phe Leu Pro Ser Leu Lys Asn Leu Gln Pro Thr Arg Pro His
            115                 120                 125

Val Val Cys Leu Val Ser Glu Phe Tyr Pro Gly Thr Leu Val Val Asp
130                 135                 140

Trp Lys Val Asp Gly Val Pro Val Thr Gln Gly Val Glu Thr Thr Gln
145                 150                 155                 160

Pro Ser Lys Gln Thr Asn Asn Lys Tyr Met Val Ser Ser Tyr Leu Thr
                165                 170                 175

Leu Ile Ser Asp Gln Trp Met Pro His Ser Arg Tyr Ser Cys Arg Val
            180                 185                 190

Thr His Glu Gly Asn Thr Val Glu Lys Ser Val Ser Pro Ala Glu Cys
            195                 200                 205

Ser

<210> SEQ ID NO 8
<211> LENGTH: 213
<212> TYPE: PRT
<213> ORGANISM: Homo sapiens
```

<400> SEQUENCE: 8

```
Met Arg Pro Gly Thr Gly Gln Gly Gly Leu Glu Ala Pro Gly Glu Pro
1               5                   10                  15

Gly Pro Asn Leu Arg Gln Arg Trp Pro Leu Leu Leu Gly Leu Ala
            20                  25                  30

Val Val Thr His Gly Leu Leu Arg Pro Thr Ala Ala Ser Gln Ser Arg
            35                  40                  45

Ala Leu Gly Pro Gly Ala Pro Gly Gly Ser Ser Arg Ser Ser Leu Arg
        50                  55                  60

Ser Arg Trp Gly Arg Phe Leu Leu Gln Arg Gly Ser Trp Thr Gly Pro
65                  70                  75                  80

Arg Cys Trp Pro Arg Gly Phe Gln Ser Lys His Asn Ser Val Thr His
                85                  90                  95

Val Phe Gly Ser Gly Thr Gln Leu Thr Val Leu Ser Gln Pro Lys Ala
            100                 105                 110

Thr Pro Ser Val Thr Leu Phe Pro Pro Ser Glu Glu Leu Gln Ala
            115                 120                 125

Asn Lys Ala Thr Leu Val Cys Leu Met Asn Asp Phe Tyr Pro Gly Ile
        130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                165                 170                 175

Ser Tyr Leu Ser Leu Thr Pro Glu Gln Trp Arg Ser Arg Arg Ser Tyr
            180                 185                 190

Ser Cys Gln Val Met His Glu Gly Ser Thr Val Glu Lys Thr Val Ala
        195                 200                 205

Pro Ala Glu Cys Ser
        210
```

<210> SEQ ID NO 9
<211> LENGTH: 158
<212> TYPE: PRT
<213> ORGANISM: Homo sapiens

<400> SEQUENCE: 9

```
Met Arg Pro Gly Thr Gly Gln Gly Gly Leu Glu Ala Pro Gly Glu Pro
1               5                   10                  15

Gly Pro Asn Leu Arg Gln Arg Trp Pro Leu Leu Leu Gly Leu Ala
            20                  25                  30

Val Val Thr His Gly Ser Val Thr His Val Phe Gly Ser Gly Thr Gln
            35                  40                  45

Leu Thr Val Leu Ser Gln Pro Lys Ala Thr Pro Ser Val Thr Leu Phe
        50                  55                  60

Pro Pro Ser Ser Glu Glu Leu Gln Ala Asn Lys Ala Thr Leu Val Cys
65                  70                  75                  80

Leu Met Asn Asp Phe Tyr Pro Gly Ile Leu Thr Val Thr Trp Lys Ala
                85                  90                  95

Asp Gly Thr Pro Ile Thr Gln Gly Val Glu Met Thr Thr Pro Ser Lys
            100                 105                 110

Gln Ser Asn Asn Lys Tyr Ala Ala Ser Ser Tyr Leu Ser Leu Thr Pro
        115                 120                 125
```

Glu Gln Trp Arg Ser Arg Arg Ser Tyr Ser Cys Gln Val Met His Glu
            130                 135                 140

Gly Ser Thr Val Glu Lys Thr Val Ala Pro Ala Glu Cys Ser
145                 150                 155

<210> SEQ ID NO 10
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Glu Thr Asp Thr Leu Leu Leu Trp Val Leu Leu Leu Trp Val Pro
1               5                   10                  15

Gly Ser Thr Gly Ser Val Thr His Val Phe Gly Ser Gly Thr Gln Leu
                20                  25                  30

Thr Val Leu Ser Gln Pro Lys Ala Thr Pro Ser Val Thr Leu Phe Pro
            35                  40                  45

Pro Ser Ser Glu Glu Leu Gln Ala Asn Lys Ala Thr Leu Val Cys Leu
50                  55                  60

Met Asn Asp Phe Tyr Pro Gly Ile Leu Thr Val Thr Trp Lys Ala Asp
65                  70                  75                  80

Gly Thr Pro Ile Thr Gln Gly Val Glu Met Thr Thr Pro Ser Lys Gln
                85                  90                  95

Ser Asn Asn Lys Tyr Ala Ala Ser Ser Tyr Leu Ser Leu Thr Pro Glu
            100                 105                 110

Gln Trp Arg Ser Arg Arg Ser Tyr Ser Cys Gln Val Met His Glu Gly
        115                 120                 125

Ser Thr Val Glu Lys Thr Val Ala Pro Ala Glu Cys Ser
    130                 135                 140

<210> SEQ ID NO 11
<211> LENGTH: 711
<212> TYPE: DNA
<213> ORGANISM: Homo sapiens
<220> FEATURE:
<221> NAME/KEY: CDS
<222> LOCATION: (8)..(547)

<400> SEQUENCE: 11 cagcaag atg gtg ttg cag acc cag gtc ttc att tct ctg ttg ctc tgg          49
        Met Val Leu Gln Thr Gln Val Phe Ile Ser Leu Leu Leu Trp
        1               5                   10 atc tct ggt gcc tac ggg gac atc gtg atg acc cag tct cca gac tcc          97
Ile Ser Gly Ala Tyr Gly Asp Ile Val Met Thr Gln Ser Pro Asp Ser
15                  20                  25                  30 ctg gct gtg tct ctg ggc gag agg gcc acc atc aac tgc aag tcc agc         145
Leu Ala Val Ser Leu Gly Glu Arg Ala Thr Ile Asn Cys Lys Ser Ser
                35                  40                  45 cag agt gtt tta tac agc tcc aac aat aag aac tac tta gct tgg tac         193
Gln Ser Val Leu Tyr Ser Ser Asn Asn Lys Asn Tyr Leu Ala Trp Tyr
            50                  55                  60 cag cag aaa cca gga cag cct cct aag ctg ctc att tac tgg gca tct         241
Gln Gln Lys Pro Gly Gln Pro Pro Lys Leu Leu Ile Tyr Trp Ala Ser
        65                  70                  75 acc cgg gaa tcc ggg gtc cct gac cga ttc agt ggc agc ggg tct ggg         289
Thr Arg Glu Ser Gly Val Pro Asp Arg Phe Ser Gly Ser Gly Ser Gly
80                  85                  90

```
aca gat ttc act ctc acc atc agc agc ctg cag gct gaa gat gtg gca      337
Thr Asp Phe Thr Leu Thr Ile Ser Ser Leu Gln Ala Glu Asp Val Ala
 95             100                 105                 110 gtt tat tac tgt cag caa tat tat agt act cct ccc aca gtg ctt cag      385
Val Tyr Tyr Cys Gln Gln Tyr Tyr Ser Thr Pro Pro Thr Val Leu Gln
            115                 120                 125 cct cga aca caa acc tcc tcc cca tac gct ggg cca gta ggt ctt tgc      433
Pro Arg Thr Gln Thr Ser Ser Pro Tyr Ala Gly Pro Val Gly Leu Cys
            130                 135                 140 tgc agc agc tgc ttc ctc tgc aca cag ccc cca aca tgc atg ctt cct      481
Cys Ser Ser Cys Phe Leu Cys Thr Gln Pro Pro Thr Cys Met Leu Pro
            145                 150                 155 ctg tgt gtt ggg gag gtc act ctc ttg att tat tcg ttg gag ggt ttg      529
Leu Cys Val Gly Glu Val Thr Leu Leu Ile Tyr Ser Leu Glu Gly Leu
        160                 165                 170 cag ggc cca gga tta aat taagagactt gacttttgct ggatctcttt             577
Gln Gly Pro Gly Leu Asn
175             180 ttgtagaaga ttattaaagc aaaatgttgt aaagatccct tagagacatt gtcaggagtt    637
tttgtgttac aggaacctgc atgtttcaca tggacacatc acatgaccga gccaaataga    697
tttatcttta ctct                                                      711

<210> SEQ ID NO 12
<211> LENGTH: 180
<212> TYPE: PRT
<213> ORGANISM: Homo sapiens

<400> SEQUENCE: 12

Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
                20                  25                  30

Val Ser Leu Gly Glu Arg Ala Thr Ile Asn Cys Lys Ser Ser Gln Ser
            35                  40                  45

Val Leu Tyr Ser Ser Asn Asn Lys Asn Tyr Leu Ala Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Thr Pro Pro Thr Val Leu Gln Pro Arg
        115                 120                 125

Thr Gln Thr Ser Ser Pro Tyr Ala Gly Pro Val Gly Leu Cys Cys Ser
    130                 135                 140

Ser Cys Phe Leu Cys Thr Gln Pro Pro Thr Cys Met Leu Pro Leu Cys
145                 150                 155                 160

Val Gly Glu Val Thr Leu Leu Ile Tyr Ser Leu Glu Gly Leu Gln Gly
                165                 170                 175

Pro Gly Leu Asn
            180

<210> SEQ ID NO 13
<211> LENGTH: 103
<212> TYPE: PRT
<213> ORGANISM: Homo sapiens
```

<400> SEQUENCE: 13

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Val Leu Pro Thr Arg Thr
            100

<210> SEQ ID NO 14
<211> LENGTH: 103
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Val Leu His Thr Gln Thr
            100

<210> SEQ ID NO 15
<211> LENGTH: 110
<212> TYPE: PRT
<213> ORGANISM: Homo sapiens

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

-continued

Glu Asp Phe Ala Thr Tyr Tyr Cys Leu Gln His Asn Ser Tyr Pro Pro
                 85                  90                  95

Thr Val Leu His Thr Arg Thr Pro Arg Glu Ala Asp Val
            100                 105                 110

<210> SEQ ID NO 16
<211> LENGTH: 98
<212> TYPE: PRT
<213> ORGANISM: Homo sapiens

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Pro
                85                  90                  95

Thr Val

<210> SEQ ID NO 17
<211> LENGTH: 101
<212> TYPE: PRT
<213> ORGANISM: Homo sapiens

<400> SEQUENCE: 17

Asp Ile Gln Met Ile Gln Ser Pro Ser Phe Leu Ser Ala Ser Val Gly
1               5                   10                  15

Asp Arg Val Ser Ile Ile Cys Trp Ala Ser Glu Gly Ile Ser Ser Asn
            20                  25                  30

Leu Ala Trp Tyr Leu Gln Lys Pro Gly Lys Ser Pro Lys Leu Phe Leu
        35                  40                  45

Tyr Asp Ala Lys Asp Leu His Pro Gly Val Ser Ser Arg Phe Ser Gly
    50                  55                  60

Arg Gly Ser Gly Thr Asp Phe Thr Leu Thr Ile Ser Leu Lys Pro
65                  70                  75                  80

Glu Asp Phe Ala Ala Tyr Tyr Cys Lys Gln Asp Phe Ser Tyr Pro Pro
                85                  90                  95

Thr Gly Leu Gln Ala
            100

<210> SEQ ID NO 18
<211> LENGTH: 136
<212> TYPE: PRT
<213> ORGANISM: Homo sapiens

<400> SEQUENCE: 18

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Gly
            20                  25                  30

Ser Asn Gly Tyr Asn Tyr Leu Asp Trp Tyr Leu Gln Lys Pro Gly Gln
        35                  40                  45

```
Ser Pro Gln Leu Leu Ile Tyr Leu Gly Ser Asn Arg Ala Ser Gly Val
     50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Ala Leu Gln Thr Pro Pro Thr Val Val Gln Pro Leu Thr Glu Thr Ser
            100                 105                 110

Ser Trp Gly Cys Pro Val Ala His Met Cys Cys Leu Ser Gly Glu Gln
        115                 120                 125

Leu Ser Arg Val Ser Glu Ser Ala
        130                 135

<210> SEQ ID NO 19
<211> LENGTH: 106
<212> TYPE: PRT
<213> ORGANISM: Homo sapiens

<400> SEQUENCE: 19

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
         35                  40                  45

Phe Arg Arg Leu Ile Tyr Lys Val Ser Asn Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Pro Thr Val Val Gln Pro
            100                 105

<210> SEQ ID NO 20
<211> LENGTH: 132
<212> TYPE: PRT
<213> ORGANISM: Homo sapiens

<400> SEQUENCE: 20

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Val Ile Pro His Glu Thr Lys Thr Pro Thr Arg Pro Ser Val Phe
            100                 105                 110
```

```
Thr Arg Leu Leu Tyr Gln Leu Leu Pro Leu Gln Thr Ala Ser Gly Val
        115                 120                 125

Ala Thr Gln Cys
    130

<210> SEQ ID NO 21
<211> LENGTH: 118
<212> TYPE: PRT
<213> ORGANISM: Homo sapiens

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His Pro
                85                  90                  95

Thr Val Ile Pro His Glu Thr Lys Thr Pro Thr Arg Pro Ser Val Phe
            100                 105                 110

Thr Arg Leu Leu Tyr Gln
        115

<210> SEQ ID NO 22
<211> LENGTH: 115
<212> TYPE: PRT
<213> ORGANISM: Homo sapiens

<400> SEQUENCE: 22

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Leu
                85                  90                  95

Thr Val Ile His Pro Val Gln Lys Pro Pro Ser Ser Leu Ser Gly Ile
            100                 105                 110

Ala Ser Ala
    115

<210> SEQ ID NO 23
<211> LENGTH: 158
<212> TYPE: PRT
<213> ORGANISM: Homo sapiens
```

<400> SEQUENCE: 23

Asp Val Val Met Thr Gln Ser Pro Ala Phe Leu Ser Val Thr Pro Gly
1               5                   10                  15

Glu Lys Val Thr Ile Thr Cys Gln Ala Ser Glu Gly Ile Gly Asn Tyr
            20                  25                  30

Leu Tyr Trp Tyr Gln Gln Lys Pro Asp Gln Ala Pro Lys Leu Leu Ile
        35                  40                  45

Lys Tyr Ala Ser Gln Ser Ile Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Lys His Pro His
                85                  90                  95

Thr Val Leu Gln Pro Lys Thr Lys Ile Ser Ser Ala Trp Arg Asn Arg
            100                 105                 110

Glu Thr Glu Gln Tyr Pro Val Phe Met Ile Leu Ala Gly Ala Val Gly
        115                 120                 125

Glu Ile Ile Tyr Gln Ile Pro Ser His Met Ala His Ser Ala Glu Leu
130                 135                 140

Thr Pro Lys Ser Gln Cys Leu Thr Leu Ser Ser Leu Pro Thr
145                 150                 155

<210> SEQ ID NO 24
<211> LENGTH: 103
<212> TYPE: PRT
<213> ORGANISM: Homo sapiens

<400> SEQUENCE: 24

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Phe Leu
            20                  25                  30

Gly Ile Asn Leu Ile His Trp Tyr Gln Gln Lys Pro Gly Gln Pro Pro
        35                  40                  45

Lys Leu Leu Ile Tyr Gln Ala Ser Asn Lys Asp Thr Gly Val Pro Ala
50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Leu Gln Ser Lys
                85                  90                  95

Asn Phe Pro Pro Thr Val Leu
            100

<210> SEQ ID NO 25
<211> LENGTH: 408
<212> TYPE: DNA
<213> ORGANISM: Homo sapiens
<220> FEATURE:
<221> NAME/KEY: CDS
<222> LOCATION: (1)..(405)

<400> SEQUENCE: 25 gtg aga agg gtt ttt gtt cag caa gac aat gga gag ctc aca ctg tgg    48
Val Arg Arg Val Phe Val Gln Gln Asp Asn Gly Glu Leu Thr Leu Trp
1               5                   10                  15 tgg acg ttc ggc caa ggg acc aag gtg gaa atc aaa cga act gtg gct    96
Trp Thr Phe Gly Gln Gly Thr Lys Val Glu Ile Lys Arg Thr Val Ala
            20                  25                  30

```
gca cca tct gtc ttc atc ttc ccg cca tct gat gag cag ttg aaa tct      144
Ala Pro Ser Val Phe Ile Phe Pro Pro Ser Asp Glu Gln Leu Lys Ser
        35                  40                  45 gga act gcc tct gtt gtg tgc ctg ctg aat aac ttc tat ccc aga gag      192
Gly Thr Ala Ser Val Val Cys Leu Leu Asn Asn Phe Tyr Pro Arg Glu
 50                  55                  60 gcc aaa gta cag tgg aag gtg gat aac gcc ctc caa tcg ggt aac tcc      240
Ala Lys Val Gln Trp Lys Val Asp Asn Ala Leu Gln Ser Gly Asn Ser
 65                  70                  75                  80 cag gag agt gtc aca gag cag gac agc aag gac agc acc tac agc ctc      288
Gln Glu Ser Val Thr Glu Gln Asp Ser Lys Asp Ser Thr Tyr Ser Leu
                 85                  90                  95 agc agc acc ctg acg ctg agc aaa gca gac tac gag aaa cac aaa ctc      336
Ser Ser Thr Leu Thr Leu Ser Lys Ala Asp Tyr Glu Lys His Lys Leu
            100                 105                 110 tac gcc tgc gaa gtc acc cat cag ggc ctg agc tcg ccc gtc aca aag      384
Tyr Ala Cys Glu Val Thr His Gln Gly Leu Ser Ser Pro Val Thr Lys
        115                 120                 125 agc ttc aac agg gga gag tgt tag                                      408
Ser Phe Asn Arg Gly Glu Cys
    130                 135

<210> SEQ ID NO 26
<211> LENGTH: 135
<212> TYPE: PRT
<213> ORGANISM: Homo sapiens

<400> SEQUENCE: 26

Val Arg Arg Val Phe Val Gln Gln Asp Asn Gly Glu Leu Thr Leu Trp
 1               5                  10                  15

Trp Thr Phe Gly Gln Gly Thr Lys Val Glu Ile Lys Arg Thr Val Ala
                20                  25                  30

Ala Pro Ser Val Phe Ile Phe Pro Pro Ser Asp Glu Gln Leu Lys Ser
        35                  40                  45

Gly Thr Ala Ser Val Val Cys Leu Leu Asn Asn Phe Tyr Pro Arg Glu
 50                  55                  60

Ala Lys Val Gln Trp Lys Val Asp Asn Ala Leu Gln Ser Gly Asn Ser
 65                  70                  75                  80

Gln Glu Ser Val Thr Glu Gln Asp Ser Lys Asp Ser Thr Tyr Ser Leu
                 85                  90                  95

Ser Ser Thr Leu Thr Leu Ser Lys Ala Asp Tyr Glu Lys His Lys Leu
            100                 105                 110

Tyr Ala Cys Glu Val Thr His Gln Gly Leu Ser Ser Pro Val Thr Lys
        115                 120                 125

Ser Phe Asn Arg Gly Glu Cys
    130                 135

<210> SEQ ID NO 27
<211> LENGTH: 119
<212> TYPE: PRT
<213> ORGANISM: Homo sapiens

<400> SEQUENCE: 27

Trp Thr Phe Gly Gln Gly Thr Lys Val Glu Ile Lys Arg Thr Val Ala
 1               5                  10                  15

Ala Pro Ser Val Phe Ile Phe Pro Pro Ser Asp Glu Gln Leu Lys Ser
                20                  25                  30

Gly Thr Ala Ser Val Val Cys Leu Leu Asn Asn Phe Tyr Pro Arg Glu
        35                  40                  45
```

```
Ala Lys Val Gln Trp Lys Val Asp Asn Ala Leu Gln Ser Gly Asn Ser
    50                  55                  60

Gln Glu Ser Val Thr Glu Gln Asp Ser Lys Asp Ser Thr Tyr Ser Leu
65                  70                  75                  80

Ser Ser Thr Leu Thr Leu Ser Lys Ala Asp Tyr Glu Lys His Lys Leu
                85                  90                  95

Tyr Ala Cys Glu Val Thr His Gln Gly Leu Ser Ser Pro Val Thr Lys
            100                 105                 110

Ser Phe Asn Arg Gly Glu Cys
            115

<210> SEQ ID NO 28
<211> LENGTH: 119
<212> TYPE: PRT
<213> ORGANISM: Homo sapiens

<400> SEQUENCE: 28

Tyr Thr Phe Gly Gln Gly Thr Lys Leu Glu Ile Lys Arg Thr Val Ala
1               5                   10                  15

Ala Pro Ser Val Phe Ile Phe Pro Pro Ser Asp Glu Gln Leu Lys Ser
                20                  25                  30

Gly Thr Ala Ser Val Val Cys Leu Leu Asn Asn Phe Tyr Pro Arg Glu
            35                  40                  45

Ala Lys Val Gln Trp Lys Val Asp Asn Ala Leu Gln Ser Gly Asn Ser
    50                  55                  60

Gln Glu Ser Val Thr Glu Gln Asp Ser Lys Asp Ser Thr Tyr Ser Leu
65                  70                  75                  80

Ser Ser Thr Leu Thr Leu Ser Lys Ala Asp Tyr Glu Lys His Lys Leu
                85                  90                  95

Tyr Ala Cys Glu Val Thr His Gln Gly Leu Ser Ser Pro Val Thr Lys
            100                 105                 110

Ser Phe Asn Arg Gly Glu Cys
            115

<210> SEQ ID NO 29
<211> LENGTH: 119
<212> TYPE: PRT
<213> ORGANISM: Homo sapiens

<400> SEQUENCE: 29

Phe Thr Phe Gly Pro Gly Thr Lys Val Asp Ile Lys Arg Thr Val Ala
1               5                   10                  15

Ala Pro Ser Val Phe Ile Phe Pro Pro Ser Asp Glu Gln Leu Lys Ser
                20                  25                  30

Gly Thr Ala Ser Val Val Cys Leu Leu Asn Asn Phe Tyr Pro Arg Glu
            35                  40                  45

Ala Lys Val Gln Trp Lys Val Asp Asn Ala Leu Gln Ser Gly Asn Ser
    50                  55                  60

Gln Glu Ser Val Thr Glu Gln Asp Ser Lys Asp Ser Thr Tyr Ser Leu
65                  70                  75                  80

Ser Ser Thr Leu Thr Leu Ser Lys Ala Asp Tyr Glu Lys His Lys Leu
                85                  90                  95

Tyr Ala Cys Glu Val Thr His Gln Gly Leu Ser Ser Pro Val Thr Lys
            100                 105                 110

Ser Phe Asn Arg Gly Glu Cys
            115
```

```
<210> SEQ ID NO 30
<211> LENGTH: 119
<212> TYPE: PRT
<213> ORGANISM: Homo sapiens

<400> SEQUENCE: 30

Leu Thr Phe Gly Gly Gly Thr Lys Val Glu Ile Lys Arg Thr Val Ala
1               5                   10                  15

Ala Pro Ser Val Phe Ile Phe Pro Pro Ser Asp Glu Gln Leu Lys Ser
            20                  25                  30

Gly Thr Ala Ser Val Val Cys Leu Leu Asn Asn Phe Tyr Pro Arg Glu
        35                  40                  45

Ala Lys Val Gln Trp Lys Val Asp Asn Ala Leu Gln Ser Gly Asn Ser
    50                  55                  60

Gln Glu Ser Val Thr Glu Gln Asp Ser Lys Asp Ser Thr Tyr Ser Leu
65                  70                  75                  80

Ser Ser Thr Leu Thr Leu Ser Lys Ala Asp Tyr Glu Lys His Lys Leu
                85                  90                  95

Tyr Ala Cys Glu Val Thr His Gln Gly Leu Ser Ser Pro Val Thr Lys
            100                 105                 110

Ser Phe Asn Arg Gly Glu Cys
        115

<210> SEQ ID NO 31
<211> LENGTH: 119
<212> TYPE: PRT
<213> ORGANISM: Homo sapiens

<400> SEQUENCE: 31

Ile Thr Phe Gly Gln Gly Thr Arg Leu Glu Ile Lys Arg Thr Val Ala
1               5                   10                  15

Ala Pro Ser Val Phe Ile Phe Pro Pro Ser Asp Glu Gln Leu Lys Ser
            20                  25                  30

Gly Thr Ala Ser Val Val Cys Leu Leu Asn Asn Phe Tyr Pro Arg Glu
        35                  40                  45

Ala Lys Val Gln Trp Lys Val Asp Asn Ala Leu Gln Ser Gly Asn Ser
    50                  55                  60

Gln Glu Ser Val Thr Glu Gln Asp Ser Lys Asp Ser Thr Tyr Ser Leu
65                  70                  75                  80

Ser Ser Thr Leu Thr Leu Ser Lys Ala Asp Tyr Glu Lys His Lys Leu
                85                  90                  95

Tyr Ala Cys Glu Val Thr His Gln Gly Leu Ser Ser Pro Val Thr Lys
            100                 105                 110

Ser Phe Asn Arg Gly Glu Cys
        115

<210> SEQ ID NO 32
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Glu Thr Asp Thr Leu Leu Leu Trp Val Leu Leu Leu Trp Val Pro
1               5                   10                  15

Gly Ser Thr Gly Val Arg Arg Val Phe Val Gln Gln Asp Asn Gly Glu
            20                  25                  30
```

```
Leu Thr Leu Trp Trp Thr Phe Gly Gln Gly Thr Lys Val Glu Ile Lys
         35                  40                  45

Arg Thr Val Ala Ala Pro Ser Val Phe Ile Phe Pro Pro Ser Asp Glu
 50                  55                  60

Gln Leu Lys Ser Gly Thr Ala Ser Val Val Cys Leu Leu Asn Asn Phe
 65                  70                  75                  80

Tyr Pro Arg Glu Ala Lys Val Gln Trp Lys Val Asp Asn Ala Leu Gln
                 85                  90                  95

Gly Asn Ser Gln Glu Ser Val Thr Glu Gln Asp Ser Lys Asp Ser Thr
            100                 105                 110

Tyr Ser Leu Ser Ser Thr Leu Thr Leu Ser Lys Ala Asp Tyr Glu Lys
        115                 120                 125

His Lys Leu Tyr Ala Cys Glu Val Thr His Gln Gly Leu Ser Ser Pro
    130                 135                 140

Val Thr Lys Ser Phe Asn Arg Gly Glu Cys
145                 150
```

<210> SEQ ID NO 33
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 33

```
Met Glu Thr Asp Thr Leu Leu Leu Trp Val Leu Leu Leu Trp Val Pro
 1               5                  10                  15

Gly Ser Thr Gly Trp Thr Phe Gly Gln Gly Thr Lys Val Glu Ile Lys
                 20                  25                  30

Arg Thr Val Ala Ala Pro Ser Val Phe Ile Phe Pro Pro Ser Asp Glu
             35                  40                  45

Gln Leu Lys Ser Gly Thr Ala Ser Val Val Cys Leu Leu Asn Asn Phe
 50                  55                  60

Tyr Pro Arg Glu Ala Lys Val Gln Trp Lys Val Asp Asn Ala Leu Gln
 65                  70                  75                  80

Gly Asn Ser Gln Glu Ser Val Thr Glu Gln Asp Ser Lys Asp Ser Thr
                 85                  90                  95

Tyr Ser Leu Ser Ser Thr Leu Thr Leu Ser Lys Ala Asp Tyr Glu Lys
            100                 105                 110

His Lys Leu Tyr Ala Cys Glu Val Thr His Gln Gly Leu Ser Ser Pro
        115                 120                 125

Val Thr Lys Ser Phe Asn Arg Gly Glu Cys
    130                 135
```

<210> SEQ ID NO 34
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 34

```
Met Glu Thr Asp Thr Leu Leu Leu Trp Val Leu Leu Leu Trp Val Pro
 1               5                  10                  15

Gly Ser Thr Gly Thr Lys Val Glu Ile Lys Arg Thr Val Ala Ala Pro
                 20                  25                  30
```

```
Ser Val Phe Ile Phe Pro Pro Ser Asp Glu Gln Leu Lys Ser Gly Thr
            35                  40                  45

Ala Ser Val Val Cys Leu Leu Asn Asn Phe Tyr Pro Arg Glu Ala Lys
 50                  55                  60

Val Gln Trp Lys Val Asp Asn Ala Leu Gln Gly Asn Ser Gln Glu Ser
 65                  70                  75                  80

Val Thr Glu Gln Asp Ser Lys Asp Ser Thr Tyr Ser Leu Ser Ser Thr
            85                  90                  95

Leu Thr Leu Ser Lys Ala Asp Tyr Glu Lys His Lys Leu Tyr Ala Cys
            100                 105                 110

Glu Val Thr His Gln Gly Leu Ser Ser Pro Val Thr Lys Ser Phe Asn
            115                 120                 125

Arg Gly Glu Cys
        130

<210> SEQ ID NO 35
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Glu Thr Asp Thr Leu Leu Leu Trp Val Leu Leu Leu Trp Val Pro
 1               5                  10                  15

Gly Ser Thr Gly Gln Pro Val Leu His Gln Pro Pro Ala Met Ser Ser
            20                  25                  30

Ala Leu Gly Thr Thr Ile Arg Leu Thr Cys Thr Leu Arg Asn Asp His
            35                  40                  45

Asp Ile Gly Val Tyr Ser Val Tyr Trp Tyr Gln Gln Arg Pro Gly His
 50                  55                  60

Pro Pro Arg Phe Leu Leu Arg Tyr Phe Ser Gln Ser Asp Lys Ser Gln
 65                  70                  75                  80

Gly Pro Gln Val Pro Pro Arg Phe Ser Gly Ser Lys Asp Val Ala Arg
            85                  90                  95

Asn Arg Gly Tyr Leu Ser Ile Ser Glu Leu Gln Pro Glu Asp Glu Ala
            100                 105                 110

Met Tyr Tyr Cys Ala Met Gly Ala Arg Ser Ser Val Thr His Val Phe
            115                 120                 125

Gly Ser Gly Thr Gln Leu Thr Val Leu Ser Gln Pro Lys Ala Thr Pro
            130                 135                 140

Ser Val Thr Leu Phe Pro Pro Ser Ser Glu Glu Leu Gln Ala Asn Lys
145                 150                 155                 160

Ala Thr Leu Val Cys Leu Met Asn Asp Phe Tyr Pro Gly Ile Leu Thr
                165                 170                 175

Val Thr Trp Lys Ala Asp Gly Thr Pro Ile Thr Gln Gly Val Glu Met
            180                 185                 190

Thr Thr Pro Ser Lys Gln Ser Asn Asn Lys Tyr Ala Ala Ser Ser Tyr
            195                 200                 205

Leu Ser Leu Thr Pro Glu Gln Trp Arg Ser Arg Ser Tyr Ser Cys
            210                 215                 220

Gln Val Met His Glu Gly Ser Thr Val Glu Lys Thr Val Ala Pro Ala
225                 230                 235                 240

Glu Cys Ser
```

```
<210> SEQ ID NO 36
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36
```

Ala Leu Asp Ile Gln Leu Thr Gln Ser Pro Ser Phe Leu Ser Ala Ser
1               5                   10                  15

Val Gly Asp Arg Val Thr Ile Thr Cys Arg Ala Ser Gln Gly Ile Asn
            20                  25                  30

Thr Trp Leu Ala Trp Tyr Gln Gln Lys Pro Gly Lys Ala Pro Lys Leu
        35                  40                  45

Leu Ile Tyr Ala Ala Ser Thr Leu Gln Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Gln Gln Leu Asn Ser Tyr
                85                  90                  95

Pro Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

```
<210> SEQ ID NO 37
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37
```

Ala Leu Asp Ile Gln Leu Thr Gln Ser Pro Ser Phe Leu Ser Ala Ser
1               5                   10                  15

Val Gly Asp Arg Val Thr Ile Thr Cys Arg Ala Ser Gln Gly Ile Ser
            20                  25                  30

Thr Asp Leu Ala Trp Tyr Gln Gln Lys Pro Gly Lys Ala Pro Lys Leu
        35                  40                  45

Leu Ile Tyr Asp Ala Ser Ser Leu Glu Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

```
Gln Pro Glu Asp Phe Ala Thr Tyr Tyr Cys Gln Gln Ala Asn Ser Phe
                85                  90                  95

Pro Phe Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 38
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Leu Glu Ile Val Leu Thr Gln Ser Pro Gly Thr Leu Ser Leu Ser
1               5                   10                  15

Pro Gly Glu Arg Ala Thr Leu Ser Cys Arg Ala Ser Gln Ser Val Ser
            20                  25                  30

Ser Ser Tyr Leu Ala Trp Tyr Gln Gln Lys Pro Gly Gln Ala Pro Arg
        35                  40                  45

Leu Leu Ile Tyr Gly Ala Ser Ser Arg Ala Thr Gly Ile Pro Asp Arg
    50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Val Tyr Tyr Cys Gln Gln Tyr Gly Asn
                85                  90                  95

Ser Pro Arg Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Arg Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

```
<210> SEQ ID NO 39
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ala Leu Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Gly Ile Ser
            20                  25                  30

Asn Tyr Leu Ala Trp Phe Gln Gln Lys Pro Gly Lys Ala Pro Lys Ser
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Asn Ser Tyr
                85                  90                  95

Pro Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 40
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ala Leu Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Gly Ile Ser
            20                  25                  30

Asn Tyr Leu Ala Trp Phe Gln Gln Lys Pro Gly Lys Ala Pro Lys Ser
        35                  40                  45

Leu Ile Tyr Ala Ala Ser Thr Leu Glu Ser Gly Val Pro Ser Arg Phe
    50                  55                  60
```

Ser Gly Ser Gly Ser Gly Thr Asp Phe Thr Leu Thr Ile Ser Ser Leu
 65                  70                  75                  80

Gln Pro Glu Asp Phe Ala Thr Tyr Tyr Cys Gln Gln Tyr Asn Ser Tyr
             85                  90                  95

Pro Leu Thr Phe Gly Gly Gly Thr Lys Val Glu Ile Lys Arg Thr Val
        100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
        210                 215

<210> SEQ ID NO 41
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ala Leu Asp Ile Gln Leu Thr Gln Ser Pro Ser Phe Leu Ser Ala Ser
 1               5                  10                  15

Val Gly Asp Arg Val Thr Ile Thr Cys Arg Ala Ser Gln Gly Ile Gly
            20                  25                  30

Asn Asp Leu Asn Trp Tyr Gln Gln Lys Pro Gly Lys Ala Pro Lys Leu
        35                  40                  45

Leu Ile Tyr Asp Ala Ser Ser Leu Glu Ser Gly Val Pro Ser Arg Phe
    50                  55                  60

Ser Gly Ser Gly Ser Gly Thr Glu Phe Thr Leu Thr Ile Ser Ser Leu
 65                  70                  75                  80

Gln Pro Glu Asp Phe Ala Thr Tyr Tyr Cys Gln Gln Ala Asp Ser Trp
             85                  90                  95

Pro Leu Thr Phe Gly Gly Gly Thr Lys Val Glu Ile Lys Arg Thr Val
        100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Ile His Gln Gly Leu Ser Ser Pro Val Thr
            195                 200                 205

Lys Ser Phe Asn Arg Gly Glu Cys
    210                 215

<210> SEQ ID NO 42
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ala Leu Asp Ile Gln Leu Thr Gln Ser Pro Ser Phe Leu Ser Ala Ser
1               5                   10                  15

Val Gly Asp Arg Val Thr Ile Thr Cys Arg Ala Ser Gln Gly Ile Ser
            20                  25                  30

Thr Asp Leu Asn Trp Tyr Gln Gln Lys Pro Gly Lys Ala Pro Lys Leu
        35                  40                  45

Leu Ile Tyr Ala Ala Ser Asn Leu Glu Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Gln Gln Ser Tyr Asn Trp
                85                  90                  95

Pro Tyr Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 43
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ala Leu Asp Ile Gln Leu Thr Gln Ser Pro Ser Phe Leu Ser Ala Ser
1               5                   10                  15

Val Gly Asp Arg Val Thr Ile Thr Cys Arg Ala Ser Gln Gly Ile Gly
            20                  25                  30

Asn Asp Leu Asn Trp Tyr Gln Gln Lys Pro Gly Lys Ala Pro Lys Leu
        35                  40                  45

Leu Ile Tyr Asp Ala Ser Ser Leu Glu Ser Gly Val Pro Ser Arg Phe
 50                  55                  60

Ser Gly Ser Gly Ser Gly Thr Glu Phe Thr Leu Thr Ile Ser Ser Leu
 65                  70                  75                  80

Gln Pro Glu Asp Phe Ala Thr Tyr Tyr Cys Gln Gln Ala Asp Ser Trp
                 85                  90                  95

Pro Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
210                 215

<210> SEQ ID NO 44
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ala Leu Asp Ile Gln Leu Thr Gln Ser Pro Ser Phe Leu Ser Ala Ser
1               5                   10                  15

Val Gly Asp Arg Val Thr Ile Thr Cys Arg Ala Ser Gln Gly Ile Ser
            20                  25                  30

Ser Tyr Leu Ala Trp Tyr Gln Gln Lys Pro Gly Lys Ala Pro Lys Leu
        35                  40                  45

Leu Ile Tyr Ala Ala Ser Thr Leu Gln Ser Gly Val Pro Ser Arg Phe
 50                  55                  60

Ser Gly Ser Gly Ser Gly Thr Glu Phe Thr Leu Thr Ile Ser Ser Leu
 65                  70                  75                  80

Gln Pro Glu Asp Phe Ala Thr Tyr Tyr Cys Gln Gln Leu Asn Ser Tyr
                 85                  90                  95

Pro Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

```
Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 45
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Ala Leu Gln Ser Ala Leu Thr Gln Pro Ala Ser Val Ser Gly Ser Pro
1               5                   10                  15

Gly Gln Ser Ile Thr Ile Ser Cys Thr Gly Thr Ser Ser Asp Val Gly
            20                  25                  30

Gly Tyr Asn Tyr Val Ser Trp Tyr Gln Gln His Pro Gly Lys Ala Pro
        35                  40                  45

Lys Leu Ile Ile Tyr Asp Val Thr Lys Arg Pro Ser Gly Val Ser Asn
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Cys Ser Tyr Thr
                85                  90                  95

Gly Thr Ser Asn Phe Val Phe Gly Gly Gly Thr Lys Leu Thr Val Leu
            100                 105                 110

Arg Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Gly Ser Pro
145                 150                 155                 160

Val Lys Ala Gly Val Glu Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Lys Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 46
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Ala Leu Ser Tyr Glu Leu Met Gln Pro Pro Ser Val Ser Val Ser Pro
1               5                   10                  15

Gly Gln Thr Ala Arg Ile Thr Cys Ser Gly Asp Ala Leu Pro Lys Gln
            20                  25                  30

Tyr Ala Tyr Trp Tyr Gln Gln Lys Pro Gly Gln Ala Pro Val Leu Val
        35                  40                  45
```

```
Ile Tyr Lys Asp Ser Glu Arg Pro Ser Gly Ile Pro Glu Arg Phe Ser
    50                  55                  60

Gly Ser Ser Ser Gly Thr Thr Val Thr Leu Thr Ile Ser Gly Val Gln
65                  70                  75                  80

Ala Glu Asp Glu Ala Asp Tyr Tyr Cys Gln Ser Ala Asp Ser Ser Gly
                85                  90                  95

Thr Tyr Val Val Phe Gly Gly Gly Thr Lys Leu Thr Val Leu Arg Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 47
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ala Leu Gln Ser Ala Leu Thr Gln Pro Ala Ser Val Ser Gly Ser Pro
1               5                   10                  15

Gly Gln Ser Ile Thr Ile Ser Cys Thr Gly Thr Ser Ser Asp Val Gly
            20                  25                  30

Gly Tyr Asn Tyr Val Ser Trp Tyr Gln Gln His Pro Gly Lys Ala Pro
        35                  40                  45

Lys Leu Met Ile Tyr Glu Val Ser Asn Arg Pro Ser Gly Val Ser Asn
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Cys Ser Tyr Thr
                85                  90                  95

Ser Thr Ser Asn Val Val Phe Gly Gly Gly Thr Lys Leu Thr Val Leu
            100                 105                 110

Arg Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Gly Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190
```

Ser His Lys Ser Tyr Ser Cys Gln Val Thr His Glu Gly Ser Thr Val
            195                 200                 205

Glu Lys Thr Val Ala Pro Thr Glu Cys Ser
        210                 215

<210> SEQ ID NO 48
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ala Leu Gln Ser Ala Leu Thr Gln Pro Ala Ser Val Ser Gly Ser Pro
1               5                   10                  15

Gly Gln Ser Ile Thr Ile Ser Cys Thr Gly Thr Ser Ser Asp Val Gly
            20                  25                  30

Ser Tyr Asn Tyr Val Ser Trp Tyr Gln Gln His Pro Gly Lys Ala Pro
        35                  40                  45

Lys Leu Ile Ile Tyr Glu Val Ser Lys Arg Pro Ser Gly Val Ser Asn
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser Tyr Ala
                85                  90                  95

Gly Thr Ser Asn Val Val Phe Gly Gly Gly Thr Lys Leu Thr Val Leu
            100                 105                 110

Arg Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Gly Ser Pro
145                 150                 155                 160

Val Lys Ala Gly Val Glu Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Lys Ser Tyr Ser Cys Gln Val Thr His Glu Gly Ser Thr Val
        195                 200                 205

Glu Lys Thr Val Ala Pro Thr Glu Cys Ser
    210                 215

<210> SEQ ID NO 49
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ala Leu Ser Ser Glu Leu Thr Gln Asp Pro Ala Val Ser Val Ala Leu
1               5                   10                  15

Gly Gln Thr Val Arg Ile Thr Cys Gln Gly Asp Ser Leu Arg Lys Lys
            20                  25                  30

Tyr Val Tyr Trp Tyr Gln Gln Lys Pro Gly Gln Ala Pro Val Leu Val
        35                  40                  45

-continued

```
Ile Tyr Lys Asp Asn Asn Arg Pro Ser Gly Ile Pro Asp Arg Phe Ser
 50                  55                  60
Gly Ser Ser Ser Gly Asn Thr Ala Ser Leu Thr Ile Thr Gly Ala Gln
 65                  70                  75                  80
Ala Glu Asp Glu Ala Asp Tyr Tyr Cys Asn Ser Trp Asp Ser Ser Ser
                 85                  90                  95
Ala His Tyr Val Phe Gly Gly Thr Lys Leu Thr Val Leu Arg Gln
            100                 105                 110
Pro Lys Ala Ala Pro Ser Val Thr Leu Phe Pro Ser Ser Glu Glu
        115                 120                 125
Leu Gln Ala Asn Lys Ala Thr Leu Val Cys Leu Ile Ser Asp Phe Tyr
130                 135                 140
Pro Gly Ala Val Thr Val Ala Trp Lys Ala Asp Gly Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Lys Ser Tyr Ser Cys Gln Val Thr His Glu Gly Ser Thr Val Glu Lys
        195                 200                 205
Thr Val Ala Pro Thr Glu Cys Ser
    210                 215

<210> SEQ ID NO 50
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ala Leu Gln Ser Ala Leu Thr Gln Pro Ala Ser Val Ser Gly Ser Pro
 1               5                  10                  15
Gly Gln Ser Ile Thr Ile Ser Cys Thr Gly Thr Ser Ser Asp Val Gly
                 20                  25                  30
Ser Tyr Asn Tyr Val Ser Trp Tyr Gln Gln His Pro Gly Lys Ala Pro
             35                  40                  45
Lys Leu Met Ile Tyr Glu Val Thr Asn Arg Pro Ser Gly Val Ser Asn
 50                  55                  60
Arg Phe Ser Gly Ser Lys Ser Gly Asn Thr Ala Ser Leu Thr Ile Ser
 65                  70                  75                  80
Gly Leu Gln Ala Glu Asp Glu Ala Asp Tyr Tyr Cys Ser Ser Tyr Ala
                 85                  90                  95
Ser Ser Ser Asn Leu Val Phe Gly Gly Thr Lys Leu Thr Val Leu
            100                 105                 110
Arg Gln Pro Lys Ala Ala Pro Ser Val Thr Leu Phe Pro Pro Ser Ser
        115                 120                 125
Glu Glu Leu Gln Ala Asn Lys Ala Thr Leu Val Cys Leu Ile Ser Asp
130                 135                 140
Phe Tyr Pro Gly Ala Val Thr Val Ala Trp Lys Ala Asp Gly Ser Pro
145                 150                 155                 160
Val Lys Ala Gly Val Glu Thr Thr Thr Pro Ser Lys Gln Ser Asn Asn
                165                 170                 175
Lys Tyr Ala Ala Ser Ser Tyr Leu Ser Leu Thr Pro Glu Gln Trp Lys
            180                 185                 190
```

Ser His Lys Ser Tyr Ser Cys Gln Val Thr His Glu Gly Ser Thr Val
        195                 200                 205

Glu Lys Thr Val Ala Pro Thr Glu Cys Ser
        210                 215

<210> SEQ ID NO 51
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ala Leu Gln Ser Ala Leu Thr Gln Pro Ala Ser Val Ser Gly Ser Pro
1               5                   10                  15

Gly Gln Ser Ile Thr Ile Ser Cys Thr Gly Thr Ser Ser Asp Val Gly
            20                  25                  30

Gly Tyr Asn Tyr Val Ser Trp Tyr Gln Gln His Pro Gly Lys Ala Pro
        35                  40                  45

Lys Leu Ile Ile Tyr Asp Val Thr Asn Arg Pro Ser Gly Val Ser Asn
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser Tyr Thr
                85                  90                  95

Gly Ser Ser Ser Tyr Val Phe Gly Gly Gly Thr Lys Leu Thr Val Leu
            100                 105                 110

Arg Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Gly Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Lys Ser Tyr Ser Cys Gln Val Thr His Glu Gly Ser Thr Val
        195                 200                 205

Glu Lys Thr Val Ala Pro Thr Glu Cys Ser
        210                 215

<210> SEQ ID NO 52
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
        35                  40                  45

-continued

Ala Tyr Ile Asn Asn Gly Ser Gly Tyr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gln Trp Trp Ser Gly Gly Asp Phe Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser
    130                 135

<210> SEQ ID NO 53
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Arg Ala Ser Asp Ser Asp Tyr Tyr Gly Trp Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser
    130                 135                 140

<210> SEQ ID NO 54
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Gly Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Arg Pro Ala Gly Pro Trp Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser
        130                 135

<210> SEQ ID NO 55
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Ala Tyr
            20                  25                  30

Ala Ile Asn Trp Val Arg Gln Ala Pro Gly Gln Gly Leu Glu Trp Met
        35                  40                  45

Gly Gly Ile Asn Val Gly Phe Gly Gly Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Trp Thr Ser Val Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser
        130                 135

<210> SEQ ID NO 56
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gly Tyr
            20                  25                  30

Gly Met His Trp Val Arg Gln Ala Pro Gly Gln Gly Leu Glu Trp Met
        35                  40                  45

Gly Trp Ile Asn Pro Ile Ser Gly Thr Ala Tyr Ala Gln Lys Phe
    50                  55                  60

Gln Gly Arg Val Thr Met Thr Arg Asp Thr Ser Ile Ser Thr Ala Tyr
65                  70                  75                  80

```
Met Glu Leu Ser Arg Leu Arg Ser Asp Asp Thr Ala Val Tyr Tyr Cys
                85                  90                  95

Ala Lys Asp Leu Ile Gly Trp Ile Ser His Ser Tyr Asn Gly Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser
    130                 135                 140

<210> SEQ ID NO 57
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Glu Met His Trp Val Arg Gln Ala Pro Gly Lys Gly Leu Glu Trp Val
        35                  40                  45

Ala Ser Ile Lys Tyr Asp Gly Ala Asn Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Ser Pro Tyr Gly Pro Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser
    130                 135

<210> SEQ ID NO 58
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Phe
            20                  25                  30

Glu Met Asn Trp Val Arg Gln Ala Pro Gly Lys Gly Leu Glu Trp Val
        35                  40                  45

Ser Gly Ile Ser Ser Asn Gly Arg Tyr Ile Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg Val Val Asp Phe Asp Gln Asp Tyr Asn Gly Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser
    130                 135                 140

<210> SEQ ID NO 59
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Glu Met His Trp Val Arg Gln Ala Pro Gly Lys Gly Leu Glu Trp Val
        35                  40                  45

Ala Ser Ile Lys Tyr Asp Gly Ala Asn Lys Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Ser Pro Tyr Gly Pro Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser
    130                 135

<210> SEQ ID NO 60
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala His
            20                  25                  30

Gly Leu Asn Trp Val Arg Gln Ala Pro Gly Gln Gly Leu Glu Trp Met
        35                  40                  45

Gly Trp Ile Asn Pro Ile Thr Gly Thr Ala Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Ser Asn Trp Gly Phe Asp Tyr Trp Gly Gln Gly
            100                 105                 110
```

```
Thr Leu Val Thr Val Ser Ser Ala Ser Thr Lys Gly Pro Ser Val Phe
        115                 120                 125

Pro Leu Ala Pro Ser Ser Lys Ser Thr Ser
    130                 135

<210> SEQ ID NO 61
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Trp Ile Ser Pro Phe Ser Gly Gly Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Trp Trp Tyr Gly Asp Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser
    130                 135

<210> SEQ ID NO 62
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Pro Ile Arg Ser Arg Gly Gly Lys Tyr Gly Gly Asp Tyr
            100                 105                 110
```

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser
    130                 135                 140

<210> SEQ ID NO 63
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Val
        35                  40                  45

Ala Asn Ile Gly Tyr Gly Gly Thr Asn Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Gly Tyr Asp Arg Tyr Gly Tyr Gly Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser
    130                 135                 140

<210> SEQ ID NO 64
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Val Ile Ser Gly Asn Ser Ala Asp Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Gly Leu Asn Tyr Leu Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser
    130                 135

<210> SEQ ID NO 65
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Asn Trp Val Arg Gln Ala Pro Gly Lys Gly Leu Glu Trp Val
        35                  40                  45

Ala Thr Ile Asn Tyr Ser Gly Thr Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Lys Ser Tyr Thr Tyr Ala Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser
    130                 135                 140

<210> SEQ ID NO 66
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Ser Trp Val Arg Gln Ala Pro Gly Lys Gly Leu Glu Trp Val
        35                  40                  45

Ser Gly Ile Ser Trp Asn Gly Gly Thr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Gly Ala Phe Tyr Leu Ser Gly Leu Asp Tyr Trp Gly
            100                 105                 110

```
Gln Gly Thr Leu Val Thr Val Ser Ser Ala Ser Thr Lys Gly Pro Ser
            115                 120                 125
Val Phe Pro Leu Ala Pro Ser Ser Lys Ser Thr Ser
        130                 135                 140

<210> SEQ ID NO 67
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Gly Met Ser Trp Val Arg Gln Ala Pro Gly Gln Gly Leu Glu Trp Met
        35                  40                  45

Gly Trp Ile Asn Ala Asn Ser Gly Gly Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Asp Gly Gly Ala Tyr Val Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser
    130                 135
```

ANTI-SURROGATE LIGHT CHAIN ANTIBODIES

REFERENCE TO RELATED APPLICATIONS

This application is a National Stage filing of PCT/US2016/015166, filed Jan. 27, 2016, under 35 U.S.C. § 371 which claims priority to U.S. Provisional Application No. 62/111,018, filed Feb. 2, 2015, each of which are incorporated by reference herein in their entireties.

REFERENCE TO THE TEXT FILE SUBMITTED ELECTRONICALLY

The contents of the text file submitted electronically herewith are incorporated herein by reference in their entirety. A computer readable format copy of the Sequence Listing (filename: i2PH_017_01US_SeqList_ST25.txt, date recorded: Oct. 30, 2017, file size: 312 kilobytes).

BACKGROUND OF THE INVENTION

Antibody (Ig) molecules produced by B-lymphocytes are built of heavy (H) and light (L) chains. The amino acid sequences of the amino terminal domains of the H and L chains are variable ($V_H$ and $V_L$), especially at the three hypervariable regions (CDR1, CDR2, CDR3) that form the antigen combining site. The assembly of the H and L chains is stabilized by a disulfide bond between the constant region of the L chain ($C_L$) and the first constant region of the heavy chain ($C_{H1}$) and by non-covalent interactions between the $V_H$ and $V_L$ domains.

In humans and many animals, such as mice, the genes encoding the antibody H and L chains are assembled by stepwise somatic rearrangements of gene fragments encoding parts of the V regions. Various stages of B lymphocyte development are characterized by the rearrangement status of the Ig gene loci (see, e.g. Melchers, F. & Rolink, A., *B-Lymphocyte Development and Biology*, Paul, W. E., ed., 1999, Lippincott, Philadelphia).

Precursors of B cells (pre-B cells) have been identified in the bone marrow by their production of a set of genes called VpreB(1-3) and λ5, instead of the fully developed light chains, and coexpression of u heavy chains.

The main isoform of human VpreB1 (CAG30495) is a 145 aa-long polypeptide (SEQ ID NO: 1). It has an Ig V domain-like structure, but lacks the last β-strand (β7) of a typical V domain, and has a carboxyl terminal end that shows no sequence homologies to any other proteins. VpreB2 has several isoforms, including a 142-amino acid mouse VpreB2 polypeptide (P13373; SEQ ID NO: 2), and a 171 amino acids long splice variant of the mouse VpreB2 sequence (CAA019641 SEQ ID NO: 3). VpreB1 and VpreB2 sequences have been disclosed in EP 0 269 127 and U.S. Pat. No. 5,182,205; Collins et al., Genome Biol. 5(10):R84 (2004); and Hollins et al., Proc. Nat. Acad Sci. USA 86(14):5552-5556 (1989). The main isoform of human VpreB3 (SEQ ID NO: 4) is a 123 aa-long protein (CAG30496), disclosed in Collins et al., Genome Biol. 5(10):R84 (2004).

VpreB(1-3) are non-covalently associated with another protein, λ5. The human λ5 is a 209-amino acid polypeptide (CAA01962; SEQ ID NO: 7), that carries an Ig C domain-like structure with strong homologies to antibody light chains and, towards its amino terminal end, two functionally distinct regions, one of which shows strong homology to the β7 strand of the Vλ domains. A human λ5-like protein has 213 amino acids (NP_064455; SEQ ID NO: 8) and shows about 84% sequence identity to the antibody A light chain constant region.

For further details, see the following review papers: Karasuyama et al., *Adv. Immunol.* 63:1-41 (1996); Melchers et al., *Immunology Today* 14:60-68 (1993); and Melchers, *Proc. Natl. Acad Sci. USA* 96:2571-2573 (1999).

The VpreB and λ5 polypeptides together form a non-covalently associated, Ig light chain-like structure, which is called the surrogate light chain or pseudo light chain. On the surface of early preB cells, the surrogate light chain is disulfide-linked to membrane-bound Ig μ heavy chain in association with a signal transducer CD79a/CD79b heterodimer to form a B cell receptor-like structure, the so-called preB cell receptor (pre-BCR).

Surrobodies™ (e.g., surrogate light chain constructs) are based on the pre-B cell receptor (pre-BCR), which is produced during normal development of antibody repertoire. Unlike antibodies, pre-BCR is a trimer, composed of an antibody heavy chain paired with two surrogate light chain components, VpreB and λ5. Both V preB and 5 are encoded by genes that do not undergo gene rearrangement and are expressed in early pre-B cells before V(D)J recombination begins. The pre-BCR is structurally different from a mature immunoglobulin in that it is composed of a heavy chain and two non-covalently associated proteins: VpreB and λ5, i.e., they have three components as opposed to two in antibodies. Furthermore, although VpreB is homologous to the Vλ Ig domain, and λ5 is homologous to the CA domain of antibodies, each has noncanonical peptide extensions: VpreB1 has additional 21 residues on its C terminus; λ5 has a 50 amino acid extension at its N terminus.

A κ-like B cell receptor (κ-like BCR) has been identified, utilizing a κ-like surrogate light chain (κ-like SLC) (Frances et al., *EMBO J*, 13:5937-43 (1994); Thompson et al., *Immunogenetics* 48:305-11 (1998); Rangel et al., *J Biol Chem* 280: 17807-14 (2005)).

Rangel et al., *J Biol Chem*, 280(18): 17807-17814 (2005) report the identification and molecular characterization of a Vκ-like protein that is the product of an unrearranged Vκ gene, which turned out to the be identical to the cDNA sequence previously reported by Thompson et al., *Immunogenetics*, 48:305-311 (1998). Whereas, Frances et al., *EMBO J*, 13:5937-43 (1994) reported the identification and characterization of a rearranged germline JCκ that has the capacity to associate with μ heavy chains at the surface of B cell precursors, thereby providing an alternative to the λ5 pathway for B cell development.

It has been proposed that κ-like and λ-like pre-BCRs work in concert to promote light chain rearrangement and ensure the maturation of B cell progenitors. For a review, see McKeller and Martinez-Valdez, *Seminars in Immunology*, 18:4043 (2006).

Further details of the design and production of Surrobodies™ (eg, surrogate light chain constructs) are provided in Xu et al., *Proc. Natl. Acad Sci., USA* 2008, 105(31):10756-61, in PCT Publication WO 2008/118970, published on Oct. 2, 2008, in U.S. Provisional Application No. 61/134,929, filed Jul. 11, 2008, and in Xu et al., *J. Mol. Biol.*, 2010, 397, 352-360, the entire disclosures of which are expressly incorporated by reference herein.

It has been described that the diversity of a filamentous phage-based combinatorial antibody library can be increased by shuffling of the heavy and light chain genes (Kang et al., *Proc. Natl. Acad Sci., USA*, 88:11120-11123, (1991)) or by introducing random mutations into the library by error-prone polymerase chain reactions (PCR) (Gram et al., *Proc. Natl. Acad Sci. USA,* 89:3576-3580, (1992)). The use of defined frameworks as the basis for generating antibody libraries has been described by Barbas et al., *Proc. Nat. Acad Sci.* USA, 89:4457-4461 (1992) (randomizing CD3-H3); Barbas et al., *Gene,* 137:57-62 (2003) (extending randomization to $V_\kappa$ CDR3); and Hayanashi et al., *Biotechniques,* 17:310 (1994) (simultaneous mutagenesis of antibody CDR regions by overlap extension and PCR). Others report combination of CDR-H3 libraries with a single $V_L$ (Nissim et al., *EMBO J.* 13:692-698 (1994)), a limited set of $V_L$ genes (De Kruif et al., *J Mol. Biol.,* 248:97-105 (1995)); or a randomized repertoire of $V_L$ genes (Griffiths et al., *EMBO J,* 13:3245-3260 (1994)).

See also U.S. Pat. Nos. 5,667,988; 6,096,551; 7,067,284 describing methods for producing antibody libraries using universal or randomized immunoglobulin light chains.

Knappik et al., *J Mol. Biol.,* 296:57-86 (2000) describe a different concept for designing and constructing human antibody libraries, designated HuCAL (Human Combinatorial Antibody Libraries). This approach is based on the finding that each of the human $V_H$ and $V_L$ subfamilies that is frequently used during an immune response is represented by one consensus framework, resulting in seven HuCAL consensus genes for heavy chains and seven HuCAL consensus genes for light chains, which yield 49 possible combinations. All genes are made by total synthesis, taking into consideration codon usage, unfavorable residues that promote protein aggregation, and unique and general restriction sites flanking all CDRs. The approach leads to the generation of modular antibody genes containing CDRs that can be converted into different antibody formats, as needed. The design and synthesis of Hu CAL antibody libraries is described in U.S. Pat. Nos. 6,300,064; 6,696,248; 6,706,484; and 6,828,422.

The construction of diverse synthetics antibody libraries is described in U.S. Pat. No. 8,131,480.

SUMMARY OF THE INVENTION

The present invention concerns anti-Surrogate Light Chain (SLC) antibodies and their uses.

In one aspect, the present invention provides isolated antibodies capable of specifically binding to a surrogate light chain (SLC), or an antigen-binding fragment thereof. In one embodiment, the antibody, or antigen-binding fragment, specifically binds to the VpreB subunit of the SLC. In another embodiment, the VpreB subunit is human VpreB1 of SEQ ID NO: 1. In one other embodiment, the VpreB subunit is mouse VpreB2 of SEQ ID NO: 2 or SEQ ID NO:3. In yet another embodiment, the VpreB subunit is human VpreB3 of SEQ ID NO: 4. In another embodiment, the antibody, or antigen-binding fragment, specifically binds to the λ5 subunit of the SLC. In one other embodiment, the λ5 subunit is human λ5 of SEQ ID NO: 7. In yet another embodiment, the λ5 subunit is human λ5 dTail of SEQ ID NO: 9.

In one embodiment, the present invention provides an antibody, or antigen-binding fragment, comprising a light chain variable region sequence selected from the group consisting of SEQ ID NOs: 36 to 51. In another embodiment, the antibody or antigen-binding fragment comprises a heavy chain variable region sequence selected from the group consisting of SEQ ID NOs: 52 to 67. In yet another embodiment, the antibody, or antigen-binding fragment, comprising a light chain variable region sequence selected from the group consisting of SEQ ID NOs: 36 to 51 further comprises a heavy chain variable region sequence selected from the group consisting of SEQ ID NOs: 52 to 67. In one other embodiment, the antigen-binding fragment is selected from the group consisting of Fab, Fab', F(ab')$_2$, scFv, and (scFv)$_2$ fragments.

In another aspect, the present invention provides compositions that contain an antibody, or antigen-binding fragment, described herein. In some embodiments, the composition is a diagnostic composition.

In one other aspect, the present invention provides methods for the diagnosis of autoimmune disease. In one embodiment, the method is used for the diagnosis of rheumatoid arthritis in a subject. In one other embodiment, the subject is a human patient. In another embodiment, the method comprises contacting a biological sample from the subject with an antibody specifically binding to human surrogate light chain (SLC) and determining the expression level of SLC.

In yet another aspect, the present invention provide methods for the diagnosis of a leukemia. In one embodiment, the leukemia is associated with aberrant SLC expression. In another embodiment, the method comprises contacting a biological sample from said subject with an antibody specifically binding to human surrogate light chain (SLC) and determining the expression level of SLC.

BRIEF DESCRIPTION OF THE DRAWINGS

FIG. 1 shows the human VpreB1 amino acid sequence of SEQ ID NO: 1 (nativeleader sequence underlined); the mouse VpreB2 sequences of SEQ ID NOs: 2 and 3; the human V preB3-like sequence of SEQ ID NO: 4, and the sequence of the truncated VpreB1 sequence in the "trimer" is shown as SEQ ID NO: 5; and the human VpreB amino acid sequence of SEQ ID NO: 6 (murine Ig kappa leader underlined). Underlining indicates the leader sequences within the VpreB amino acid sequences.

FIG. 2 shows the human λ5 sequence of SEQ ID NO: 7; the human λ5-like sequence of SEQ ID NO: 8; the sequence of the truncated λ5 sequence in the "trimer" designated as "λ5 dTail" (SEQ ID NO: 9); and the human λ5 dTail sequence of SEQ ID NO: 10 with a murine Ig κ leader sequence. Underlining indicates the leader sequences within the λ5 amino acid sequences.

FIG. 3 shows the human VpreB1-λ5 chimeric amino acid sequence as SEQ ID NO: 35 (murine Ig κ leader sequence underlined).

FIG. 4A and FIG. 4B show the human Vκ-like nucleotide sequence of SEQ ID NO: 11 and the amino acid sequence of the encoded protein (AJ004956; SEQ ID NO: 12) (native leader sequence underlined) (FIG. 4A), and the predicted mature amino acid sequences of Vκ-like proteins possible from all Vκ families (FIG. 4B), each bearing different lengths of extensions (SEQ ID NOs: 13-24) aligned with AJ004956 Vκ-like prototype sequence (SEQ ID NO: 12).

FIG. 5A-FIG. 5C shows the human JCκ nucleotide sequence of SEQ ID NO: 25 and the amino acid sequence of the encoded protein (SEQ ID NO: 26) (unique sequence compared to predicted mature JCκ proteins is doubly underlined and potential leader cleavage sequence singly underlined) (FIG. 5A), and the predicted JCκ-like amino acid sequences from the remaining kappa J-constant region rearrangements (J1-J5Cκ) (SEQ ID NOs: 27-31) (FIG. 5B), and the JCκ engineered secretion optimized variants, including JCκ with an appended murine Ig κ leader sequence underlined (SEQ ID NO: 32), a recombined JCκ only with an appended murine Ig κ leader sequence underlined (SEQ ID NO: 33), and a predicted processed JCκ with an appended murine Ig κ leader sequence underlined (SEQ ID NO: 34) (FIG. 5C).

FIG. 6A-FIG. 6B show the light chain sequences of anti-human VpreB1 Fab proteins (SEQ ID NOs: 36-51).

FIG. 7 shows the heavy chain sequences (VH) of anti-human VpreB1 Fab proteins (SEQ ID NOs: 52-67).

FIG. 17A-FIG. 17C show the PK serum ELISA results of the pre-immune serum samples.

FIG. 23 shows test articles used in the *Cynomolgus* monkey PK study.

DETAILED DESCRIPTION OF THE INVENTION

A. Definitions

Figure 8:
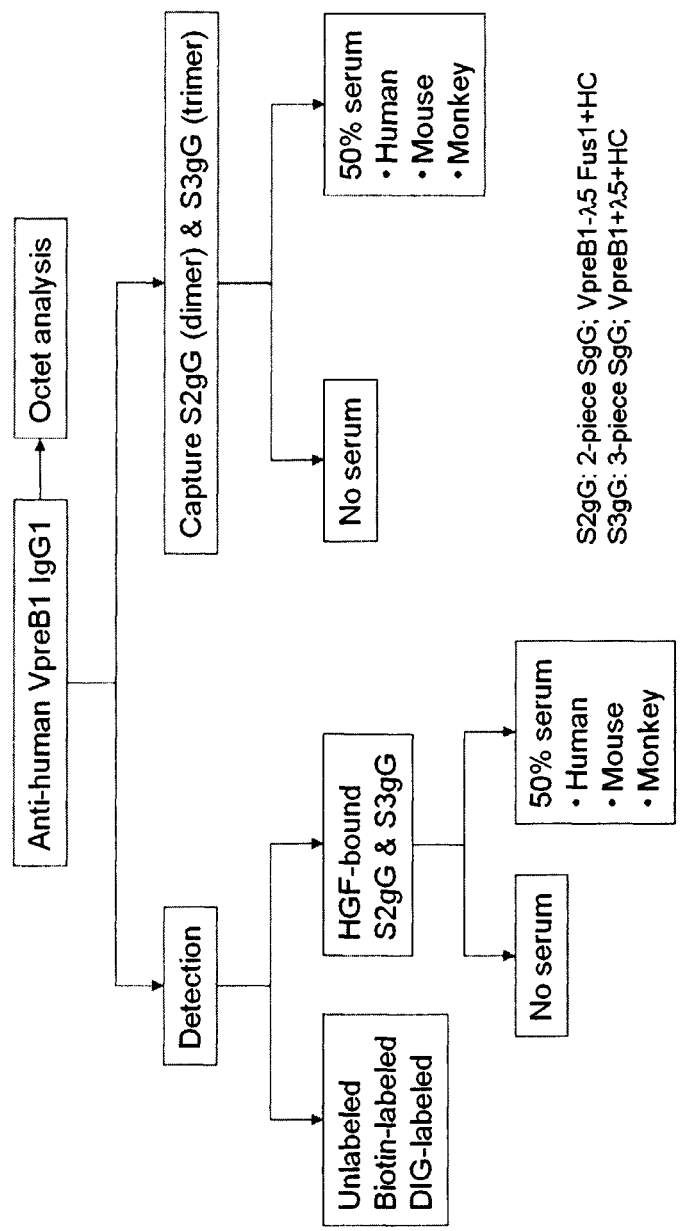
FIG. 8 illustrates an overview of the characterization methods used for anti-human VpreB1 IgG1 (2460B04 IgG1).

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

Throughout this application, the use of singular includes the plural unless expressly stated otherwise.

In this application, the use of "or" includes "and/or", unless expressly stated otherwise.

Furthermore, the terms, "include," "including," and "included," are not limiting.

In the context of the present invention, the term "antibody" (Ab) is used to refer to a native antibody from a classically recombed heavy chain derived from V(D)J gene recombination and a classically recombed light chain also derived from VJ gene recombination, or a fragment thereof.

A "native antibody" is heterotetrameric glycoprotein of about 150,000 daltons, composed of two identical light (L) chains and two identical heavy (H) chains. Each light chain is linked to a heavy chain by covalent disulfide bond(s), while the number of disulfide linkages varies between the heavy chains of different immunoglobulin isotypes. Each heavy and light chain also has regularly spaced intrachain disulfide bridges. Each heavy chain has, at one end, a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains, Chothia et al., *J. Mol. Biol.* 186:651 (1985); Novotny and Haber, *Proc. Natl. Acad Sci. U.S.A.* 82:4592 (1985).

The term "variable" with reference to antibody chains is used to refer to portions of the antibody chains which differ extensively in sequence among antibodies and participate in the binding and specificity of each particular antibody for its particular antigen. Such variability is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3, and FR4, respectively), largely adopting a 3-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR" (i.e., residues 30-36 (L1), 46-55 (L2) and 86-96 (L3) in the light chain variable domain and 30-35 (H1), 47-58 (H2) and 93-101 (H3) in the heavy chain variable domain; MacCallum et al., *J Mol Biol.* 262(5):732-45 (1996).

The term "framework region" refers to the art recognized portions of an antibody variable region that exist between the more divergent CDR regions. Such framework regions are typically referred to as frameworks 1 through 4 (FR1, FR2, FR3, and FR4) and provide a scaffold for holding, in three-dimensional space, the three CDRs found in a heavy or light chain antibody variable region, such that the CDRs can form an antigen-binding surface.

Depending on the amino acid sequence of the constant domain of their heavy chains, antibodies can be assigned to different classes. There are five major classes of antibodies IgA, IgD, IgE, IgG, and IgM, and several of these may be further divided into subclasses (isotypes), e.g., IgG1, IgG2, IgG3, IgG4, IgA, and IgA2. In a preferred embodiment, the immunoglobulin sequences used in the construction of the immunoadhesins of the present invention are from an IgG immunoglobulin heavy chain domain. For human immunoadhesins, the use of human IgG1 and IgG3 immunoglobulin sequences is preferred. A major advantage of using the IgG1 is that IgG immunoadhesins can be purified efficiently on immobilized protein A. However, other structural and functional properties should be taken into account when choosing the Ig fusion partner for a particular immunoadhesin construction. For example, the IgG3 hinge is longer and more flexible, so that it can accommodate larger "adhesin" domains that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit. For VEGF receptor Ig-like domain/immunoglobulin chimeras designed for in vivo applications, the pharmacokinetic properties and the effector functions specified by the Fc region are important as well. Although IgG1, IgG2 and IgG4 all have in vivo half-lives of 21 days, their relative potencies at activating the complement system are different. Moreover, various immunoglobulins possess varying numbers of allotypic isotypes.

The heavy-chain constant domains that correspond to the different classes of immunoglobulins are called α, δ, ε, γ, and μ, respectively.

The "light chains" of antibodies from any vertebrate species can be assigned to one of two clearly distinct types, called kappa (κ) and lambda (λ), based on the amino acid sequences of their constant domains. Any reference to an antibody light chain herein includes both κ and λ light chains.

"Antibody fragments" comprise a portion of a full length antibody, generally the antigen binding or a variable domain thereof. Examples of antibody fragments include, but are not limited to, Fab, Fab', F(ab')$_2$, scFv, and (scFv)$_2$ fragments.

As used herein the term "antibody binding region" refers to one or more portions of an immunoglobulin or antibody variable region capable of binding an antigen(s). Typically, the antibody binding region is, for example, an antibody light chain (or variable region thereof, ($V_L$)), an antibody heavy chain (or variable region thereof, ($V_H$)), a heavy chain Fd region, a combined antibody light and heavy chain (or variable region thereof) such as a Fab, F(ab')$_2$, single domain, or single chain antibody (scFv), or a full length antibody, for example, an IgG (e.g., an IgG1, IgG2, IgG3, or IgG4 subtype), IgA1, IgA2, IgD, IgE, or IgM antibody.

The term "epitope" as used herein, refers to a sequence of at least about 3 to 5, preferably at least about 5 to 10, or at least about 5 to 15 amino acids, and typically not more than about 500, or about 1,000 amino acids, which define a sequence that by itself, or as part of a larger sequence, binds to an antibody generated in response to such sequence. An epitope is not limited to a polypeptide having a sequence identical to the portion of the parent protein from which it is derived. Indeed, viral genomes are in a state of constant change and exhibit relatively high degrees of variability between isolates. Thus the term "epitope" encompasses sequences identical to the native sequence, as well as modifications, such as deletions, substitutions and/or insertions to the native sequence. Generally, such modifications are conservative in nature but non-conservative modifications are also contemplated. The term specifically includes "mimotopes," i.e. sequences that do not identify a continuous linear native sequence or do not necessarily occur in a native protein, but functionally mimic an epitope on a native protein. The term "epitope" specifically includes linear and conformational epitopes.

The term "surrogate light chain polypeptide" or "SLC polypeptide" is used herein to refer to a VpreB polypeptide, a λ5 polypeptide, a Vκ-like polypeptide, a Jκ polypeptide, or variants thereof.

The term "non-surrogate light chain molecule" or "non-SLC molecule" is used herein to refer to a molecule that is not an SLC polypeptide. The non-SLC molecule may be a polypeptide, such as a cytokine or antibody fragment.

The term "VpreB" is used herein in the broadest sense and refers to any native sequence or variant VpreB polypeptide, specifically including, without limitation, human VpreB1 of SEQ ID NO: 1, mouse VpreB2 of SEQ ID NOS: 2 and 3, human VpreB3-like sequence of SEQ ID NO: 4, human VpreB dT of SEQ ID NO:5, human VpreB1 amino acid sequence of SEQ ID NO:6 and isoforms, including splice variants and variants formed by posttranslational modifications, other mammalian homologues thereof, as well as variants of such native sequence polypeptides. (See FIG. 1)

The term "λ5" is used herein in the broadest sense and refers to any native sequence or variant λ5 polypeptide, specifically including, without limitation, human λ5 of SEQ ID NO: 7, human λ5-like protein of SEQ ID NO: 8, the human λ5 dT shown as SEQ ID NOs: 9 and 10, and their isoforms, including splice variants and variants formed by posttranslational modifications, other mammalian homologous thereof, as well a variants of such native sequence polypeptides. (See FIG. 2)

Specific examples of λ-like Surrobody™ (e.g., surrogate light chain constructs) include polypeptides in which a VpreB sequence, such as a VpreB1, VpreB2, or VpreB3 sequence, including fragments and variants of the native sequences, is conjugated to a λ5 sequence, including fragments and variants of the native sequence. Representative fusions of this type are provided in PCT Publication WO 2008/118970, published on Oct. 2, 2008, the entire disclosures of which are expressly incorporated by reference herein. An example of a fusion with a heterogeneous leader sequence is illustrated in FIG. 3 (SEQ ID NO: 35).

The terms "variant VpreB polypeptide" and "a variant of a VpreB polypeptide" are used interchangeably, and are defined herein as a polypeptide differing from a native sequence VpreB polypeptide at one or more amino acid positions as a result of an amino acid modification. The "variant VpreB polypeptide," as defined herein, will be different from a native antibody λ or κ light chain sequence, or a fragment thereof. The "variant VpreB polypeptide" will preferably retain at least about 65%, or at least about 70%, or at least about 75%, or at least about 80%, or at least about 85%, or at least about 90%, or at least about 95%, or at least about 98% sequence identity with a native sequence VpreB polypeptide. In another preferred embodiment, the "variant VpreB polypeptide" will be less than 95%, or less than 90%, or less than 85%, or less than 80%, or less than 75%, or less than 70%, or less than 65%, or less than 60% identical in its amino acid sequence to a native antibody λ or κ light chain sequence. Variant VpreB polypeptides specifically include, without limitation, VpreB polypeptides in which the non-Ig-like unique tail at the C-terminus of the VpreB sequence is partially or completely removed.

The terms "variant λ5 polypeptide" and "a variant of a λ5 polypeptide" are used interchangeably, nd are defined herein as a polypeptide differing from a native sequence λ5 polypeptide at one or more amino acid positions as a result of an amino acid modification. The "variant λ5 polypeptide," as defined herein, will be different from a native antibody λ or κ light chain sequence, or a fragment thereof. The "variant λ5 polypeptide" will preferably retain at least about 65%, or at least about 70%, or at least about 75%, or at least about 80%, or at least about 85%, or at least about 90%, or at least about 95%, or at least about 98% sequence identity with a native sequence λ5 polypeptide. In another preferred embodiment, the "variant λ5 polypeptide" will be less than 95%, or less than 90%, or less than 85%, or less than 80%, or less than 75%, or less than 70%, or less than 65%, or less than 60% identical in its amino acid sequence to a native antibody λ or κ light chain sequence. Variant λ5 polypeptides specifically include, without limitation, λ5 polypeptides in which the unique tail at the N-terminus of the λ5 sequence is partially or completely removed.

The terms "variant Vκ-like polypeptide" and "a variant of a Vκ-like polypeptide" are used interchangeably, and are defined herein as a polypeptide differing from a native sequence Vκ-like polypeptide at one or more amino acid positions as a result of an amino acid modification. The "variant Vκ-like polypeptide," as defined herein, will be different from a native antibody λ or κ light chain sequence, or a fragment thereof. (See FIG. 4) The "variant Vκ-like polypeptide" will preferably retain at least about 65%, or at least about 70%, or at least about 75%, or at least about 80%, or at least about 85%, or at least about 90%, or at least about 95%, or at least about 98% sequence identity with a native sequence Vκ-like polypeptide. In another preferred embodiment, the "variant Vκ-like polypeptide" will be less than 95%, or less than 90%, or less than 85%, or less than 80%, or less than 75%, or less than 70%, or less than 65%, or less than 60% identical in its amino acid sequence to a native antibody λ or κ light chain sequence. Variant Vκ-like polypeptides specifically include, without limitation, Vκ-like polypeptides in which the non-Ig-like unique tail at the C-terminus of the Vκ-like sequence is partially or completely removed.

The terms "variant JCκ polypeptide" and "a variant of a JCκ polypeptide" are used interchangeably, and are defined herein as a polypeptide differing from a native sequence JCκ polypeptide at one or more amino acid positions as a result of an amino acid modification. (See FIG. 5) The "variant JCκ polypeptide," as defined herein, will be different from a native antibody λ or κ light chain sequence, or a fragment thereof. The "variant JCκ polypeptide" will preferably retain at least about 65%, or at least about 70%, or at least about 75%, or at least about 80%, or at least about 85%, or at least about 90%, or at least about 95%, or at least about 98% sequence identity with a native sequence JCκ polypeptide. In another preferred embodiment, the "variant JCκ polypeptide" will be less than 95%, or less than 90%, or less than 85%, or less than 80%, or less than 75%, or less than 70%, or less than 65%, or less than 60% identical in its amino acid sequence to a native antibody λ or κ light chain sequence. Variant JCκ polypeptides specifically include, without limitation, JCκ polypeptides in which the unique tail at the N-terminus of the JCκ sequence is partially or completely removed.

Percent amino acid sequence identity may be determined using the sequence comparison program NCBI-BLAST2 (Altschul et al., *Nucleic Acids Res.* 25:3389-3402 (1997)). The NCBI-BLAST2 sequence comparison program may be downloaded from National Center for Biotechnology Information website, or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

The term "VpreB sequence" is used herein to refer to the sequence of "VpreB," as hereinabove defined, or a fragment thereof.

The term "λ5 sequence" is used herein to refer to the sequence of "λ5," as hereinabove defined, or a fragment thereof.

The term "Vκ-like sequence" is used herein to refer to the sequence of "Vκ-like," as hereinabove defined, or a fragment thereof.

The term "JCκ sequence" is used herein to refer to the sequence of "JCκ," as hereinabove defined, or a fragment thereof.

The term "λ-like surrogate light chain," as used herein, refers to a dimer formed by the non-covalent association of a VpreB and a λ5 protein.

The term "κ-like surrogate light chain," as used herein, refers to a dimer formed by the non-covalent association of a Vκ-like and a JCκ protein.

The term "λ-like surrogate light chain sequence," as defined herein, means any polypeptide sequence that comprises a "VpreB sequence" and/or a "λ5 sequence," as hereinabove defined. The "λ-like surrogate light chain sequence," as defined herein, specifically includes, without limitation, the human VpreB1 sequence of SEQ ID NO: 1, the mouse VpreB2 sequences of SEQ ID NOs: 2 and 3, and the human VpreB3 sequence of SEQ ID NO: 4, the human VpreB dT shown as SEQ ID NO: 5; and the human VpreB1 amino acid sequence of SEQ ID NO: 6 and their various isoforms, including splice variants and variants formed by posttranslational modifications, homologues thereof in other mammalian species, as well as fragments and variants thereof. The term "λ-like surrogate light chain sequence" additionally includes, without limitation, the human λ5 sequence of SEQ ID NO: 7, the human λ5-like sequence of SEQ ID NO: 8, the human λ5 dTail shown as SEQ ID NO: 9, the human λ5 dTail sequence of SEQ ID NO: 10 and their isoforms, including splice variants and variants formed by posttranslational modifications, homologues thereof in other mammalian species, as well as fragments and variants thereof. The term "λ-like surrogate light chain sequence" additionally includes a sequence comprising both VpreB and λ5 sequences as hereinabove defined.

The term "κ-like surrogate light chain sequence," as defined herein, means any polypeptide sequence that comprises a "Vκ-like sequence" and/or a "JCκ," as hereinabove defined. The "κ-like surrogate light chain sequence," as defined herein, specifically includes, without limitation, the human Vκ-like sequence of any of SEQ ID NOs: 12-24, and their various isoforms, including splice variants and variants formed by posttranslational modifications, homologues thereof in other mammalian species, as well as fragments and variants thereof. The term "κ-like surrogate light chain sequence" additionally includes, without limitation, the human Vκ-like sequence of any of SEQ ID NOs: 12-24, the human JCκ sequence of any of SEQ ID NOs: 25-35, and their isoforms, including splice variants and variants formed by posttranslational modifications, homologues thereof in other mammalian species, as well as fragments and variants thereof. The term "κ-like surrogate light chain sequence" additionally includes a sequence comprising both Vκ-like and JCκ sequences as hereinabove defined.

The term, "surrogate light chain construct" is used in the broadest sense and includes any and all additional heterogeneous components, including a heterogeneous amino acid sequence, nucleic acid, and other molecules conjugated to a surrogate light chain sequence, wherein "conjugation" is defined below.

A "surrogate light chain construct" is also referred herein as a "Surrobody™," and the two terms are used interchangeably. Certain λ-like surrogate light chain constructs are disclosed in Xu et al., *Proc. Natl. Acad Sci. USA* 2008, 105(31):10756-61 and in PCT Publication WO 2008/118970, published on Oct. 2, 2008. Also contemplated are κ-like surrogate light chain constructs as described in U.S. Patent Publication No. 2010-0062950, and Xu et al., *J. Mol. Biol.* 2010, 397, 352-360, the entire disclosures of which are expressly incorporated by reference herein.

In the context of the polypeptides of the present invention, the term "heterogeneous amino acid sequence," relative to a first amino acid sequence, is used to refer to an amino acid sequence not naturally associated with the first amino acid sequence, at least not in the form it is present in the surrogate light chain constructs herein. Thus, a "heterogeneous amino acid sequence" relative to a VpreB, λ5, Vκ-like, or JCκ is any amino acid sequence not associated with native VpreB, λ5, Vκ-like, or JCκ in its native environment. These include, without limitation, i) λ5 sequences that are different from those λ5 sequences that, together with VpreB, form the surrogate light chain on developing B cells, such as amino acid sequence variants, e.g. truncated and/or derivatized λ5 sequences; ii) VpreB sequences that are different from those VpreB sequences that, together with λ5, form the surrogate light chain on developing B cells, such as amino acid sequence variants, e.g. truncated and/or derivatized VpreB sequences; iii) Vκ-like sequences that are different from those Vκ-like sequences that, together with JCκ, form the κ-like surrogate light chain on developing B cells, such as amino acid sequence variants, e.g. truncated and/or derivatized Vκ-like sequences; and iv) JCκ sequences that are different from those JCκ sequences that, together with Vκ-like, form the κ-like surrogate light chain on developing B cells, such as amino acid sequence variants, e.g. truncated and/or derivatized JCκ sequences.

A "heterogeneous amino acid sequence" relative to a VpreB or 5 also includes VpreB or λ5 sequences covalently associated with, e.g. fused to, a corresponding VpreB or λ5, including native sequence VpreB or λ5, since in their native environment, the VpreB and λ5 sequences are not covalently associated, e.g. fused, to each other. Similarly, a "heterogeneous amino acid sequence" relative to a Vκ-like or JCκ also includes Vκ-like or JCκ sequences covalently associated with, e.g. fused to, a corresponding Vκ-like or JCκ, including native sequence Vκ-like or JCκ, since in their native environment, the Vκ-like or JCκ sequences are not covalently associated, e.g. fused, to each other. Heterogeneous amino acid sequences also include, without limitation, antibody sequences, including antibody and heavy chain sequences and fragments thereof, such as, for example, antibody light and heavy chain variable region sequences, and antibody light and heavy chain constant region sequences.

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association, for example through Van der Waals forces, or by using a leucine zipper.

The term "flexible linker" is used herein to refer to any linker that is not predicted, based on its chemical structure, to be fixed in three-dimensional space in its intended context and environment.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

As used herein, the terms "peptide," "polypeptide" and "protein" all refer to a primary sequence of amino acids that are joined by covalent "peptide linkages." In general, a peptide consists of a few amino acids, typically from about 2 to about 50 amino acids, and is shorter than a protein. The term "polypeptide," as defined herein, encompasses peptides and proteins.

The term "amino acid" or "amino acid residue" typically refers to an amino acid having its art recognized definition such as an amino acid selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); praline (Pro); serine (Ser); threonine (Thr); tryptophan (Trp); tyrosine (Tyr); and valine (Val) although modified, synthetic, or rare amino acids may be used as desired. Thus, modified and unusual amino acids listed in 37 CFR 1.822 (b)(4) are specifically included within this definition and expressly incorporated herein by reference. Amino acids can be subdivided into various sub-groups. Thus, amino acids can be grouped as having a nonpolar side chain (e.g., Ala, Cys, Ile, Leu, Met, Phe, Pro, Val); a negatively charged side chain (e.g., Asp, Glu); a positively charged side chain (e.g., Arg, His, Lys); or an uncharged polar side chain (e.g., Asn, Cys, Gln, Gly, His, Met, Phe, Ser, Thr, Trp, and Tyr). Amino acids can also be grouped as small amino acids (Gly, Ala), nucleophilic amino acids (Ser, His, Thr, Cys), hydrophobic amino acids (Val, Leu, Iie, Met, Pro), aromatic amino acids (Phe, Tyr, Trp, Asp, Glu), amides (Asp, Glu), and basic amino acids (Lys, Arg).

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety.

The term "variant" with respect to a reference polypeptide refers to a polypeptide that possesses at least one amino acid mutation or modification (i.e., alteration) as compared to a native polypeptide. Variants generated by "amino acid modifications" can be produced, for example, by substituting, deleting, inserting and/or chemically modifying at least one amino acid in the native amino acid sequence.

An "amino acid modification" refers to a change in the amino acid sequence of a predetermined amino acid sequence. Exemplary modifications include an amino acid substitution, insertion and/or deletion.

An "amino acid modification at" a specified position, refers to the substitution or deletion of the specified residue, or the insertion of at least one amino acid residue adjacent the specified residue. By insertion "adjacent" a specified residue is meant insertion within one to two residues thereof. The insertion may be N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); praline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein.

A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, omithine, norvaline, homoserine and other amino acid residue analogues such as those described in Ellman et al., *Meth. Enzym.*, 202:301336 (1991). To generate such non-naturally occurring amino acid residues, the procedures of Noren et al., *Science*, 244: 182 (1989) and Ellman et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

The term "mutagenesis" refers to, unless otherwise specified, any art recognized technique for altering a polynucleotide or polypeptide sequence. Preferred types of mutagenesis include error prone PCR mutagenesis, saturation mutagenesis, or other site directed mutagenesis.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the single-stranded phage DNA, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. Plaques of interest are selected by hybridizing with kinased synthetic primer at a temperature that permits hybridization of an exact match, but at which the mismatches with the original strand are sufficient to prevent hybridization. Plaques that hybridize with the probe are then selected, sequenced and cultured, and the DNA is recovered.

The term "vector" is used to refer to a recombinant DNA molecule (rDNA) capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors. "The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. A vector may be a "plasmid" referring to a circular double-stranded DNA loop into which additional DNA segments may be ligated. A vector may be a phage vector or a viral vector, in which additional DNA segments may be ligated into the viral genome. Suitable vectors are capable of autonomous replication in a host cell into which they are introduced, e.g., bacterial vector with a bacterial origin or replication and episomal mammalian vectors. A vector may be integrated into the host cell genome, e.g., a non-episomal mammalian vector, upon introduction into the host cell, and replicated along with the host genome.

Nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

A "phage display library" is a protein expression library that expresses a collection of cloned protein sequences as fusions with a phage coat protein. Thus, the phrase "phage display library" refers herein to a collection of phage (e.g., filamentous phage) wherein the phage express an external (typically heterologous) protein. The external protein is free to interact with (bind to) other moieties with which the phage are contacted. Each phage displaying an external protein is a "member" of the phage display library.

The term "filamentous phage" refers to a viral particle capable of displaying a heterogeneous polypeptide on its surface, and includes, without limitation, fl, fd, Pfl, and M13. The filamentous phage may contain a selectable marker such as tetracycline (e.g., "fd-tet"). Various filamentous phage display systems are well known to those of skill in the art (see, e.g., Zacher et al., *Gene,* 9: 127-140 (1980), Smith et al., *Science,* 228: 1315-1317 (1985); and Parmley and Smith, *Gene,* 73: 305-318 (1988)).

The term "panning" is used to refer to the multiple rounds of screening process in identification and isolation of phages carrying compounds, such as antibodies, with high affinity and specificity to a target.

A "host cell" includes an individual cell or cell culture which can be or has been a recipient for transformation of nucleic acid(s) and/or vector(s) containing nucleic acids encoding the molecules described herein. In methods of the present invention, a host cell can be a eukaryotic cell, such as a Chinese Hamster Ovary (CHO) cell, or a human embryonic kidney (HEK) 293 cell. Other suitable host cells are known to those skilled in the art.

B. Detailed Description

Techniques for performing the methods of the present invention are well known in the art and described in standard laboratory textbooks, including, for example, Ausubel et al., *Current Protocols of Molecular Biology,* John Wiley and Sons (1997); *Molecular Cloning: A Laboratory Manual,* Third Edition, J. Sambrook and D. W. Russell, eds., Cold Spring Harbor, N.Y., USA, Cold Spring Harbor Laboratory Press, 2001; O'Brian et al., *Analytical Chemistry of Bacillus Thuringiensis,* Hickle and Fitch, eds., Am. Chem. Soc., 1990; *Bacillus thuringiensis: biology, ecology and safety,* T. R. Glare and M. O'Callaghan, eds., John Wiley, 2000; *Antibody Phage Display, Methods and Protocols,* Humana Press, 2001; and Antibodies, G. Subramanian, ed., Kluwer Academic, 2004. Mutagenesis can, for example, be performed using site-directed mutagenesis (Kunkel et al., Proc. Natl. Acad Sci USA 82:488-492 (1985)). PCR amplification methods are described in U.S. Pat. Nos. 4,683,192, 4,683, 202, 4,800,159, and 4,965,188, and in several textbooks including *PCR Technology: Principles and Applications for DNA Amplification,* H. Erlich, ed., Stockton Press, New York (1989); and *PCR Protocols: A Guide to Methods and Applications,* Innis et al., eds., Academic Press, San Diego, Calif. (1990).

The present invention concerns antibodies against the surrogate light chain (SLC). The antibodies can be directed against the VpreB subunit, the λ5 subunit, or the fusion junction as each of these antibodies will specifically bind the surrogate light chain.

Anti-SLC antibodies may be used for a variety of applications. One application is detection of SLC-containing proteins in complex biological fluids in pharmacokinetic/pharmacodynamic studies, immunohistochemistry studies or for in vitro diagnostic uses.

Another application for anti-SLC antibodies is for diagnostic purposes. There are a number of conditions known in the art associated with the absence or deficiency of SLC. For example, λ5-deficient mice show a dramatic decrease in B-cell development, (Kitamura D et al., *Cell.* 1992; 69(5): 823-831) whereas mutations in the human λ5 gene result in agammaglobulinemia, (Minegishi Y et al., *J Exp Med.,* 1998; 187(1):71-77.) In humans, self-reactive B cells have been identified which express SLC and these cells have been shown to accumulate in the joints of patients with RA (Meffre et al., (2000) *Nature Immunology* 1, 207-213). Thus, SLC could be a marker for poly-reactive cells and aberrant pre-BCR function. Accordingly, anti-SLC antibodies may be a useful reagent for diagnosing certain leukemias and autoimmune diseases that are associated with aberrant SLC expression and B cell function.

In addition, purification of SLC complexes as fusion proteins, non-covalent heteromers, or as cell populations can also be considered for the use of anti-SLC antibodies. As a research reagent, anti-SLC antibodies can be used to assess the biophysical and functional characteristics of SLC-containing complexes in vitro. Quantification, affinity determination, effective or inhibitory concentration, immunoprecipitation, and immunosorbent applications for SLC-complexes are examples of important uses for the anti-SLC antibodies.

The antibodies of the present invention can, for example, be obtained by screening antibody libraries, such as diverse antibody libraries described in U.S. Pat. No. 8,131,480, which, in a preferred embodiment, use of phage vectors to express the diverse antibody libraries. The method generally involves the use of a filamentous phage (phagemid) surface expression vector system for cloning and expression. See, e.g., Kang et al., *Proc. Natl. Acad Sci., USA,* 88:4363-4366 (1991); Barbas et al., *Proc. Natl. Acad Sci., USA,* 88:7978-7982 (1991); Zebedee et al., *Proc. Natl. Acad Sci., USA,* 89:3175-3179 (1992); Kang et al., *Proc. Natl. Acad Sci., USA,* 88: 11120-11123 (1991); Barbas et al., *Proc. Natl. Acad Sci., USA,* 89:4457-4461 (1992); Gram et al., Proc. Natl. Acad Sci., USA, 89:3576-3580 (1992); Brinkman et al., *J Immunol. Methods* 182:41-50 (1995); Ames et al., *J Immunol. Methods* 184:177-186 (1995); Kettleborough et al., *Eur. J Immunol.* 24:952-958 (1994); Persic et al., *Gene* 187 9-18 (1997); Burton et al., *Advances in Immunology* 57: 191-280 (1994); and U.S. Pat. Nos. 5,698,426; 5,233,409; 5,580,717; 5,427,908; 5,750,753; 5,821,047; 5,403,484; 5,571,698; 5,516,637; 5,780,225; 5,658,727; 5,733,743; 5,837,500; 5,969,108; 6,326,155; 5,885,793; 6,521,404; 6,492,160, 6,492,123; 6,489,123; 6,342,588; 6,291,650; 6,225,447; 6,180,336; 6,172,197; 6,140,471; 5,994,519; 6,969,108; 5,871,907; and 5,858,657.

The vector is used to transform a recombinant host cell, which is cultured to allow the introduced phage genes and display protein genes to be expressed, and for phage particles to be assembled and shed from the host cell. The shed phage particles are then harvested (collected) from the host cell culture media and screened for desirable antibody binding properties. Typically, the harvested particles are "panned" for binding with a preselected antigen. The strongly binding particles are collected, and individual species of particles are clonally isolated and further screened for binding to the antigen. Phages which produce a binding site of desired antigen binding specificity are selected.

The invention is further described in the following non-limiting Examples.

Examples

Example 1—Identification of Anti-VpreB1 Fabs

Sea Lane's proprietary Fab fragment libraries were panned against human VpreB-1 for 4 rounds. Typically, after three to four rounds of panning, individual clones from enriched phage pools were analyzed by ELISA against human VpreB1, and the positive clones were sequenced to determine their heavy and light chain sequences. From these studies, Fab clonal analyses identified 16 unique human VpreB1 binders (Table 1). As further characterized in Table 2, both kappa and lambda light chains were identified with 4 different heavy chain frameworks.

TABLE 1

Unique Positive Clones for Anti-human VpreB1

| Unique Sequence | $V_L$ | $V_H$ |
|---|---|---|
| 2462VpreBlam5E07 | VK1_L8 | VH3-321 |
| 2462VpreBlam5C04 | VK1_L8 | VH3-323 |
| 2462VpreBlam5B09 | VK3_A27 | VH1-102 |
| 2463VpreBlam5B05 | VK1_L1 | VH1-1e |
| 2463VpreBlam5D07 | VK1_L1 | VH1-102 |
| 2460-VpreBlam5D10 | VK1_L8 | VH3-321 |
| 2460VpreBlam5B04 | VK1_L8 | VH3-321 |
| 2462VpreBlam5A07 | VK1_L8 | VH3-321 |
| 2460VpreBlam5E01 | VK1_L8 | VH1-102 |
| 2462VpreBlam5D05 | VL2_2a2 | VH1-1e |
| 2462VpreBlam5A05 | VL3_8m | VH1-102 |
| 2462VpreBlam5C09 | VL2_2a2 | VH3-323 |
| 2460-VpreBlam5F05 | VL2_2a2 | VH3-323 |
| 2462VpreBlam5E08 | VL3_3L | VH3-323 |
| 2462VpreBlam5C05 | VL2_2a2 | VH3-321 |
| 2463VpreBlam5C04 | VL2_2a2 | VH1-102 |

TABLE 2

Overview of light and heavy chain sequences among the anti-human VpreB1 Fab hits

|  | Lambda | Kappa |
|---|---|---|
| VH1_02 | 2 | 3 |
| VH1-e | 1 | 1 |
| VH3_21 | 1 | 4 |
| VH3_23 | 3 | 1 |

The amino acid sequence of the specific anti-human VpreB1 Fab clones was determined and the variable region sequences were identified and analyzed using the FASTA program. The light chain sequences (VL) of the anti-human VpreB1 Fab clones were aligned as depicted in FIG. 6A-FIG. 6B. Within this alignment, the variable light chain starts at residue number 3 and the point at which the variable light chain sequence transitions to the constant light chain (Cκ or Cλ) is demarcated with arrows. The heavy chain sequences ($V_H$) of anti-human VpreB1 Fab clones were aligned as depicted in FIG. 7. Within this alignment, the variable heavy chain starts at residue number 1 and the point at which the variable heavy chain and J-chain sequence transitions to the constant heavy chain is demarcated with arrows.

Example 2—Characterization of Selected Anti-VpreB1 IgG mAbs

ELISA assays were performed to characterize the SgG-binding affinity, sensitivity and serum background of individual panned phage Fab antibodies having affinity for human VpreB1. FIG. 8 provides an overview of the characterization of anti-human VpreB1 IgG1 (2460804 IgG1). SgG proteins refer to surrogate light chain (SLC) constructs, also referred herein as a "Surrobody™," and the two terms are used interchangeably. In general, the 2-piece format includes an SLC fusion and an antibody heavy chain, while the 3-piece format includes two SLC polypeptides and an antibody heavy chain.

Detection

Figure 9:
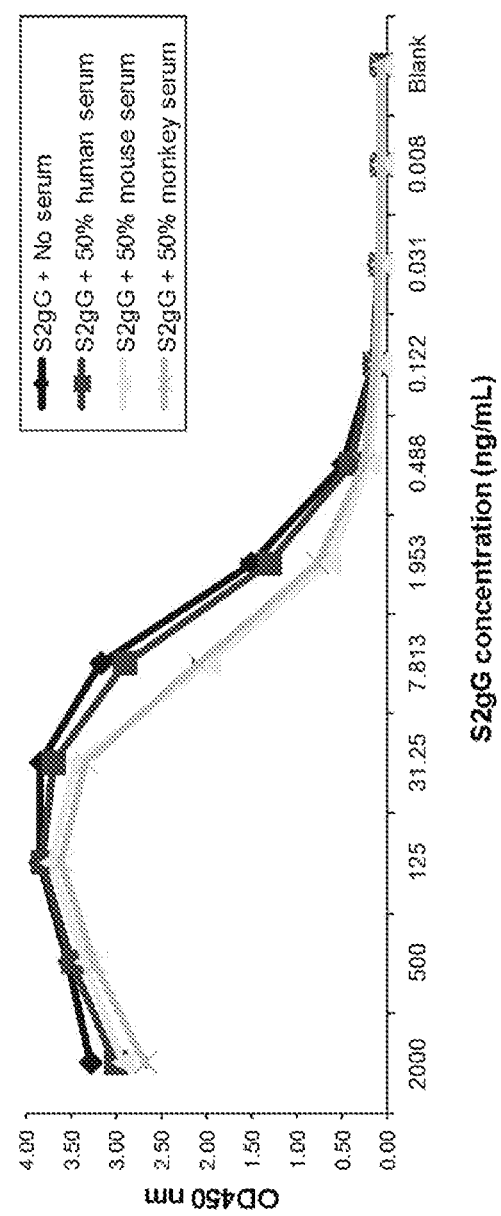
FIG. 9 demonstrates that anti-VpreB1 antibody (2460B04 IgG1) detects HGF-bound 2-piece Surrobody™ (e.g., 2-piece surrogate light chain construct) in 50% serum.
Figure 10:
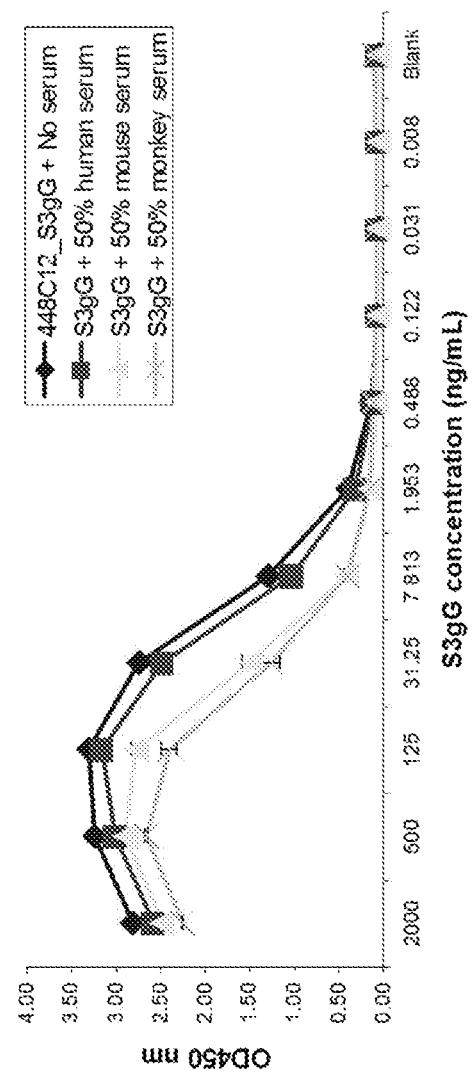
FIG. 10 demonstrates that anti-VpreB1 antibody (2460B04 IgG1) detects HGF-bound 3-piece Surrobody™ (e.g., 3-piece surrogate light chain construct) in 50% serum.

To assess the anti-human VpreB1 IgG1 (2460B04 IgG1) as a detection antibody, HGF-specific S2gG & S3gG were detected by unlabeled, biotin-labeled, & DIG-labeled anti-VpreB1 antibodies by ELISA. In the assays to detect either the 2-piece or 3-piece Surrobody™ (e.g., 2-piece or 3-piece surrogate light chain constructs), wells were coated with HGF (0.1 mL of 0.001 mg/mL), 1% BSA-PBST was used as a blocking and diluent buffer, and S2gG or S3gG were serial diluted in 50% serum. HGF-bound S2gG or S3gG was detected by biotinylated anti-VpreB1 IgG & HRP-conjugated streptavidin. As demonstrated in FIG. 9, the anti-VpreB1 antibody detects the HGF-bound 2-Piece Surrobody™ (e.g., 2-piece surrogate light chain constructs) in 50% serum. Similarly, the anti-VpreB1 antibody also detects HGF-bound 3-Piece Surrobody™ (e.g., 3-piece surrogate light chain constructs) in 50% serum (FIG. 10). The $EC_{50}$ values for the different SLC constructs used in the detection assays are provided in Table 3 below.

TABLE 3

Unlabeled vs. Labeled Anti-Human VpreB1 IgG Antibody

| | $EC_{50}$ (nM) (ELISA) | | |
|---|---|---|---|
| SgG | Unlabeled | Biotin-labeled | DIG-labeled |
| S2gG | 0.605 | 0.549 | 0.535 |
| S3gG | 0.482 | 0.48 | 0.432 |

Capture

Figure 11:
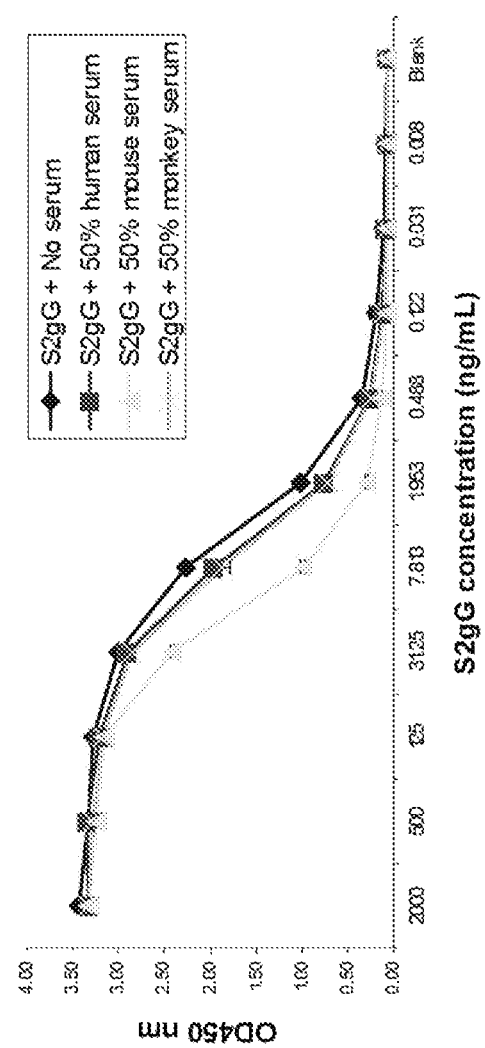
FIG. 11 demonstrates that anti-VpreB1 antibody (2460B04 IgG1) captures 2-piece Surrobody™ (e.g., 2-piece surrogate light chain construct) in 50% serum.
Figure 12:
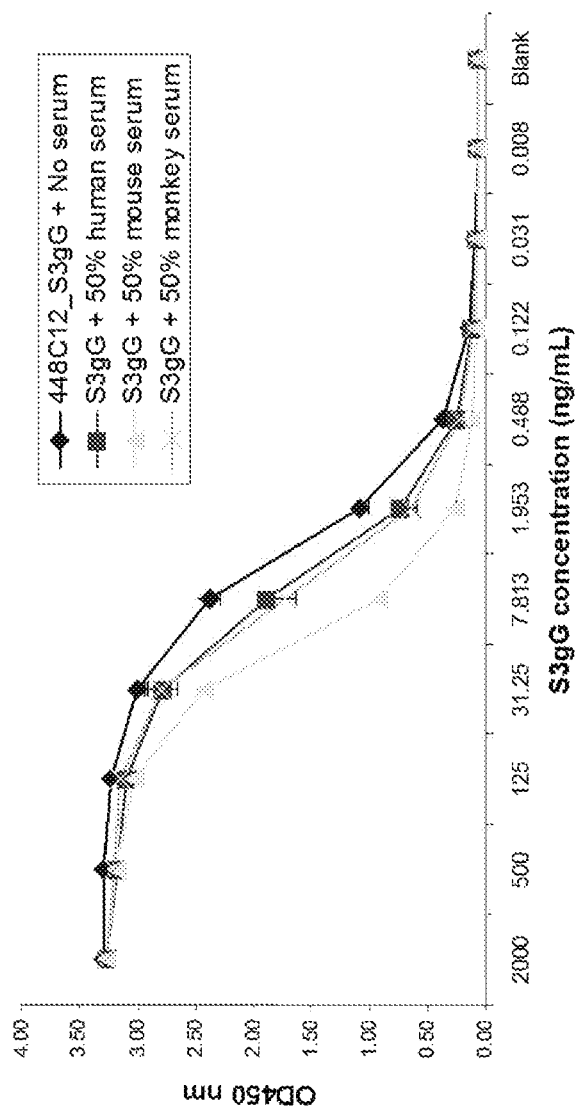
FIG. 12 demonstrates that anti-VpreB1 antibody (2460B04 IgG1) captures 3-piece Surrobody™ (e.g., 3-piece surrogate light chain construct) in 50% serum.
Figure 13A:
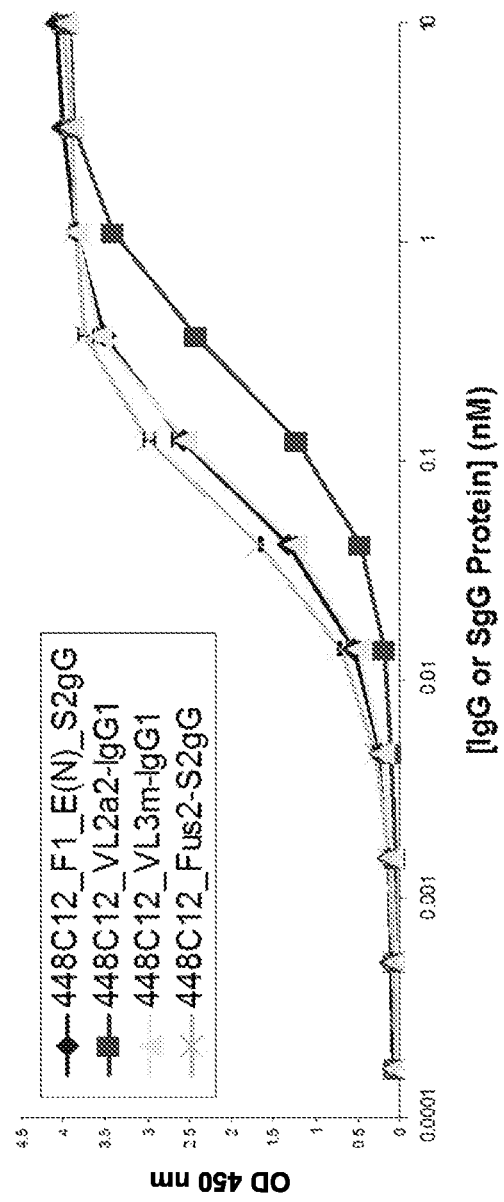
FIG. 13A-FIG. 13D demonstrates that anti-VpreB1 mAb (2460B04 IgG1) used as a detection reagent does not bind to IgG containing human VL ORF.
Figure 13B:
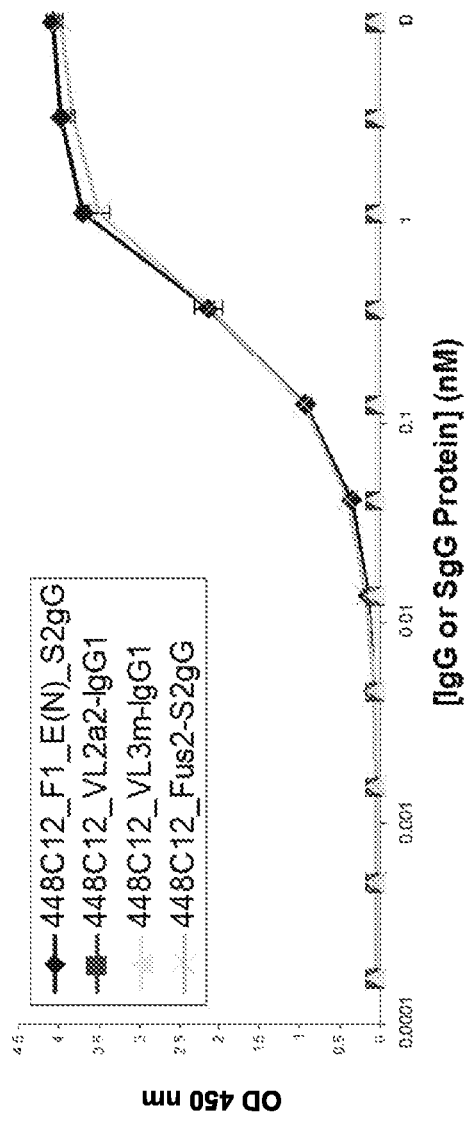
Figure 13C:
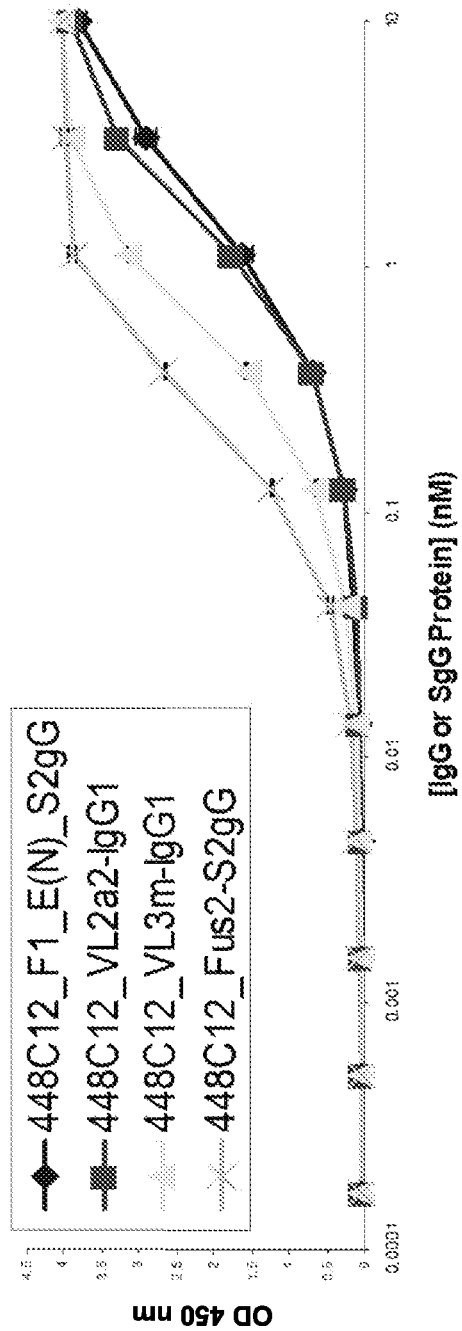
Figure 13D:
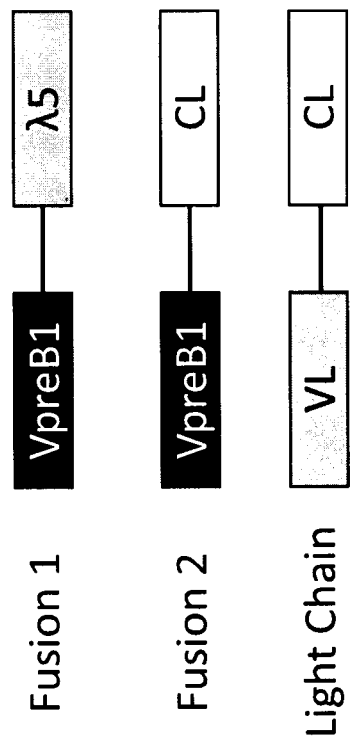

In the assays to assess 2-piece or 3-piece Surrobody™ (e.g., 2-piece or 3-piece surrogate light chain construct) capture by anti-VpreB1 IgG (2460B04 IgG1), wells were coated with anti-VpreB1 IgG (0.1 mL of 0.001 mg/mL), 1% BSA-PBST was used as a blocking and diluent buffer, and S2gG or S3gG were serial diluted in 50% serum. HGF-bound S2gG was detected by HRP-conjugated goat anti-E tag Ab. As demonstrated in FIG. 11, the anti-VpreB1 antibody captures 2-Piece Surrobody™ (e.g., 2-piece surrogate light chain construct) in 50% serum. The anti-VpreB1 antibody also captures the 3-Piece Surrobody™ (e.g., 3-piece surrogate light chain construct) in 50% serum (FIG. 12).

Affinity

The binding affinity of anti-human VpreB1 IgG mAb (2460B04 IgG1) to SgG was tested by Biolayer Interferometry on a ForteBio Octet ("octet analysis"). Kinetic binding analysis was performed and the apparent affinities are reported in Table 4. The results indicate a sub-nanomolar affinity to bind to 2-piece or 3-piece SLC constructs.

TABLE 4

Binding Affinity of Anti-Human VpreB1 IgG mAb to SgG Measured by Octet

| Run | SA Biosensor Immobilization | Binding Titration Format | $K_D$ [nM] | kobsRsq |
|---|---|---|---|---|
| 1 | 0.75 µg/mL αHGF S2gG-biotin | 100 µg/mL αVpreB_IgG | 0.280-0.100 | 0.979-0.998 |
| 2 | 0.75 µg/mL αHGF S2gG-biotin | 50 µg/mL αVpreB_IgG | 0.120-0.066 | 0.981-0.998 |

TABLE 4-continued

Binding Affinity of Anti-Human VpreB1 IgG mAb to SgG Measured by Octet

| Run | SA Biosensor Immobilization | Binding Titration Format | $K_D$ [nM] | kobsRsq |
|---|---|---|---|---|
| 3 | 0.75 µg/mL αVpreB_IgG_biotin | 50 µg/mL αHGF S2gG | 0.048-0.016 | 0.967-0.988 |
| 4 | 0.75 µg/mL αVpreB_IgG_biotin | 50 µg/mL αHGF S3gG | 0.058-0.032 | 0.983-0.993 |

The anti-human VpreB1 IgG mAb (2460B04 IgG1) demonstrated a clean background in the presence of human, mouse, or *Cynomolgus* monkey serum. This suggests that the 2460B04 IgG1 antibody would be useful in pharmacokinetic (PK) studies. Further applications suggested by these results are as a detection reagent with minimal cross reactivity in human, mouse and monkey serum (15 ng/mL), as a capture reagent with minimal cross reactivity in human, mouse and monkey serum, and as an affinity antibody to enrich libraries in VpreB1-contained library construction.

Cross Reactivity

Cross reactivity of the anti-VpreB1 mAb (2460B04 IgG1) to human $V_L$ were examined by ELISA. Table 5 provides an overview of the methods used to examine the cross reactivity of the anti-VpreB1 mAb. Table 6 identifies the protein sequence similarity of IgG containing human $V_L$ ORFs.

TABLE 5

Characterization of Cross-Reactivity of the Anti-VpreB1 mAb

| Capture Reagent | Detection Reagent | Goal |
|---|---|---|
| Target (hHGF) | Donkey anti-human IgG Fcγ-HRP (Jackson 709-035-098) Goat anti-human λ-HRP (Southern) Anti-VpreB1 hIgG1-HRP | Target binding |
| anti-VpreB1 mIgG2a | Mouse αhuman λ mAb-HRP (Clone JDC-10, Southern) Goat anti-human λ-HRP (Southern) | Complex formation VpreB1-captured CL |
| Donkey anti-human IgG Fcγ (Jackson 709-005-098) | Goat anti-human λ-HRP (Southern) | Complex formation |

Figure 14C:
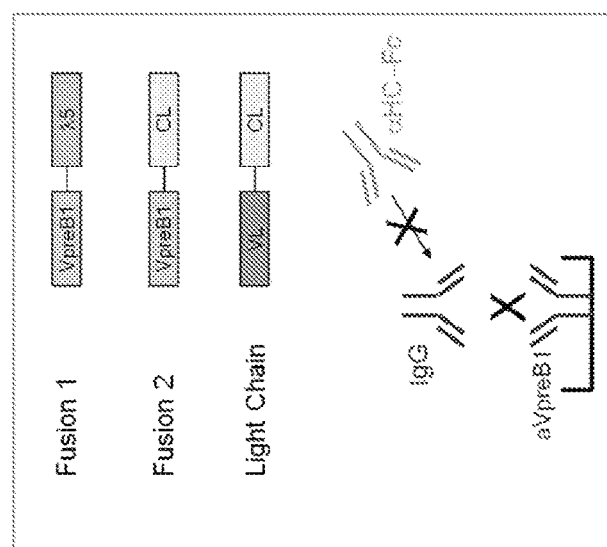
FIG. 14A-FIG. 14C demonstrates that anti-VpreB1 mAb is unable to capture $V_L$-containing IgG (448C12-HC).
Figure 14A:
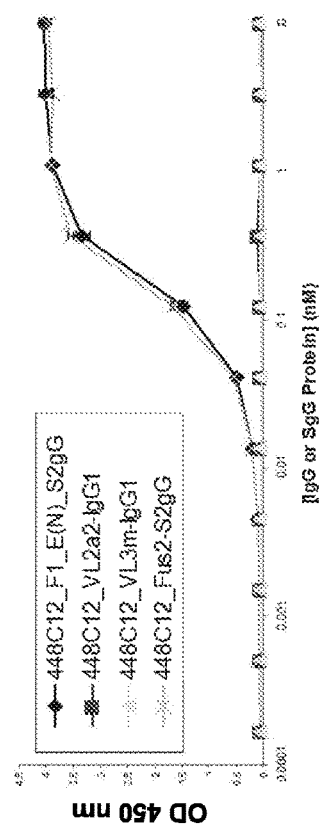
Figure 14B:
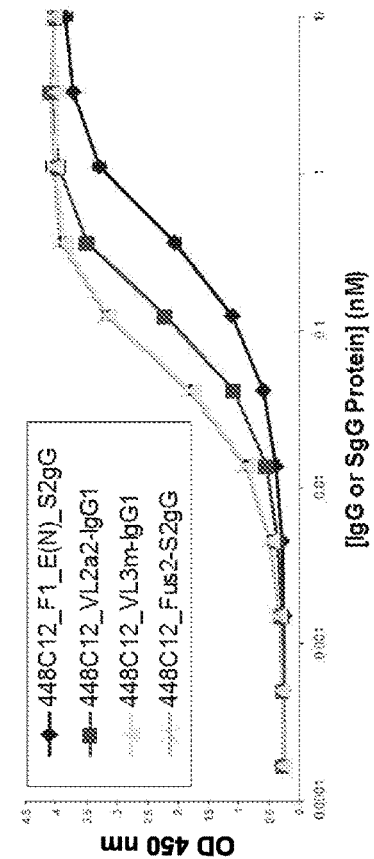
Figure 15C:
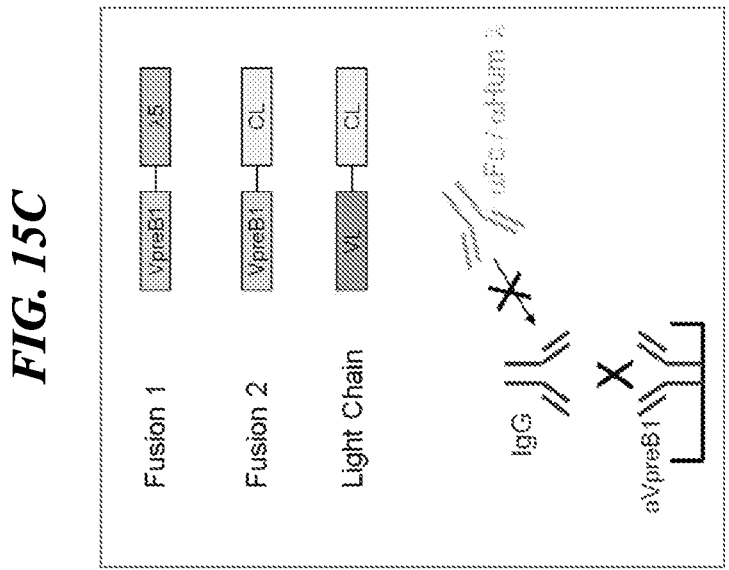
FIG. 15A-FIG. 15C demonstrates that anti-VpreB1 mAb is unable to capture $V_L$-containing IgG (2547C02 HC)
Figure 15A:
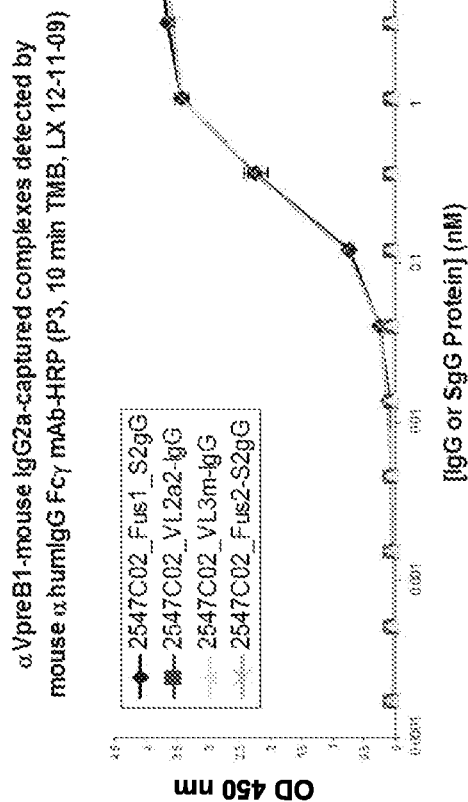
Figure 15B:
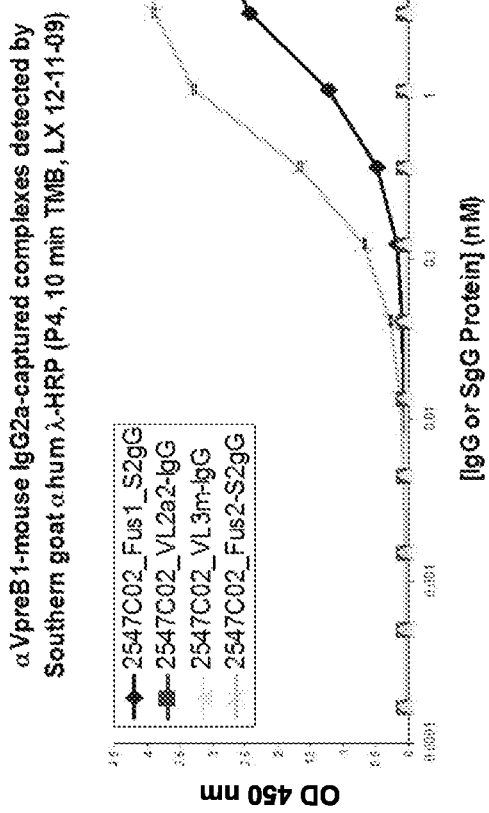
Figure 16C:
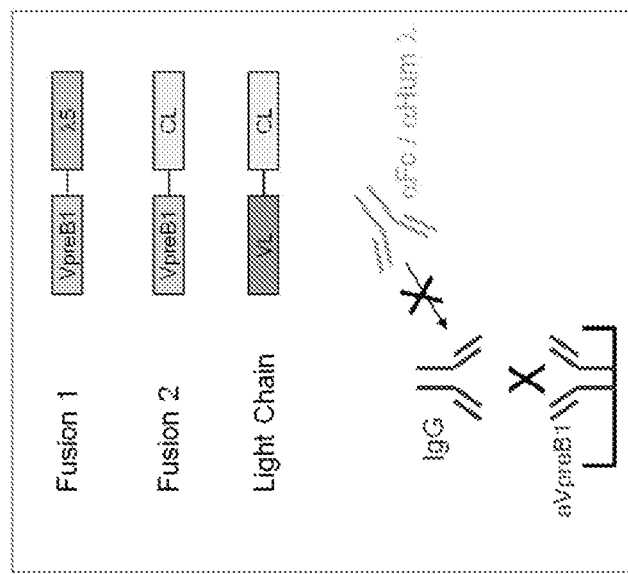
FIG. 16A-FIG. 16C demonstrates that anti-VpreB1 mAb is unable to capture $V_L$-containing IgG (2211A01_N56H-HC).
Figure 16A:
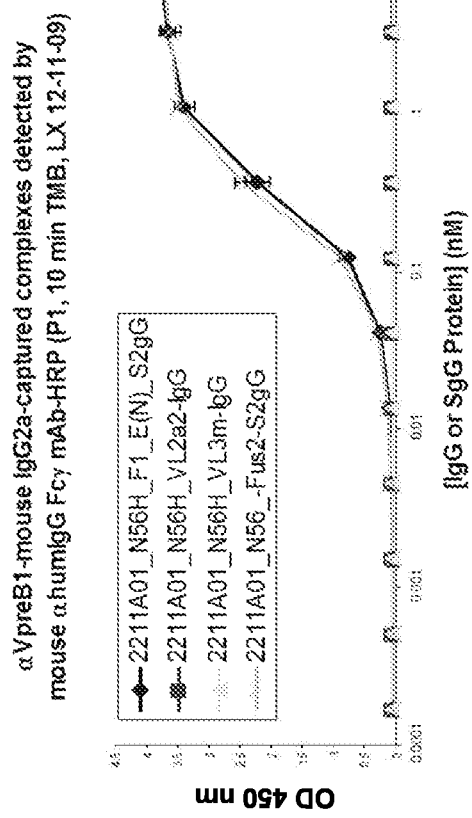
Figure 16B:
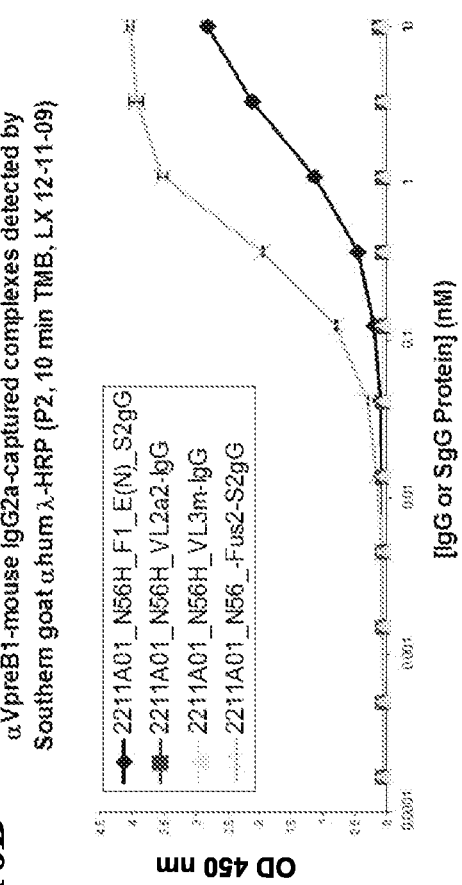

When used as a detection reagent, the anti-VpreB1 mAb does not bind to IgG-containing human $V_L$ ORF (FIG. 13A-FIG. 13D). Likewise, when used as a capture reagent, the anti-VpreB1 mAb is unable to capture VL-contained IgG (448C12-HC) (FIG. 14A-FIG. 14C). The anti-VpreB1 mAb is also unable to capture the $V_L$-contained IgGs represented by 2547C02 HC (FIG. 15A-FIG. 15C) or 2211A01_N56H-HC (FIG. 16A-FIG. 16C). Thus, there appears to be no cross reactivity to traditional light chain proteins.

Example 3—Pharmacokinetic Study of Surrobodies™ (e.g., SLCs) in *Cynomolgus* Monkey The utility of the anti-VpreB1 IgG mAbs was further demonstrated in pharmacokinetic (PK) studies of Surrobodies in the *Cynomolgus* monkey. The PK profile of Surrobodies™ (e.g., surrogate light chain constructs) in *Cynomolgus* monkeys was assessed by measurements of half-life (T½), maximum plasma/serum concentration (Cmax), elimination rate constant, AUC0-t (area under the plasma concentration-time curve to the last observed data point), and clearance. We also examined the anti-SgG response that resulted from a single-injection. The Surrobody™ (e.g., surrogate light chain construct) test articles used in the *Cynomolgus* monkey PK study are identified in FIG. 23.

Figure 17B:
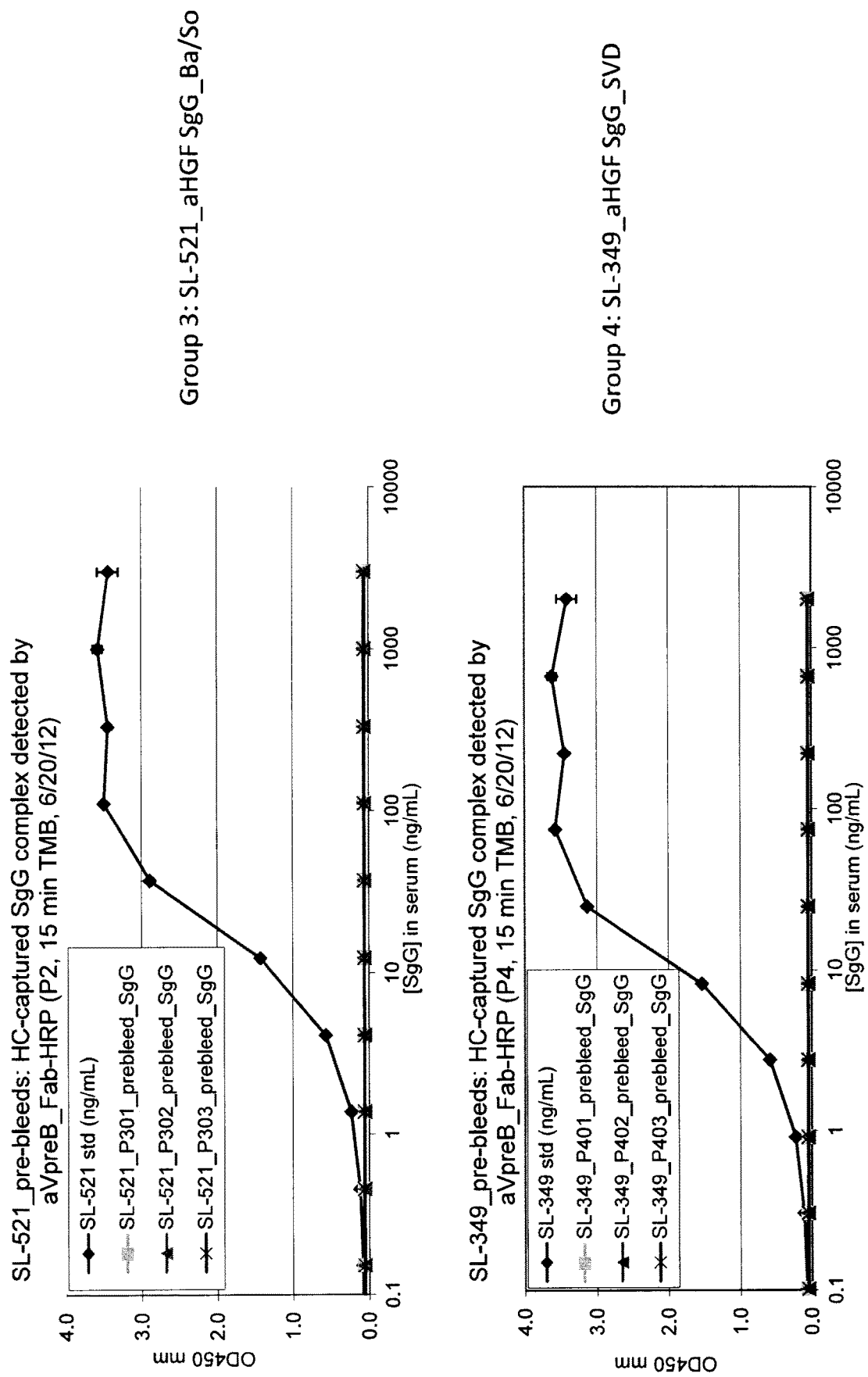
Figure 17C:
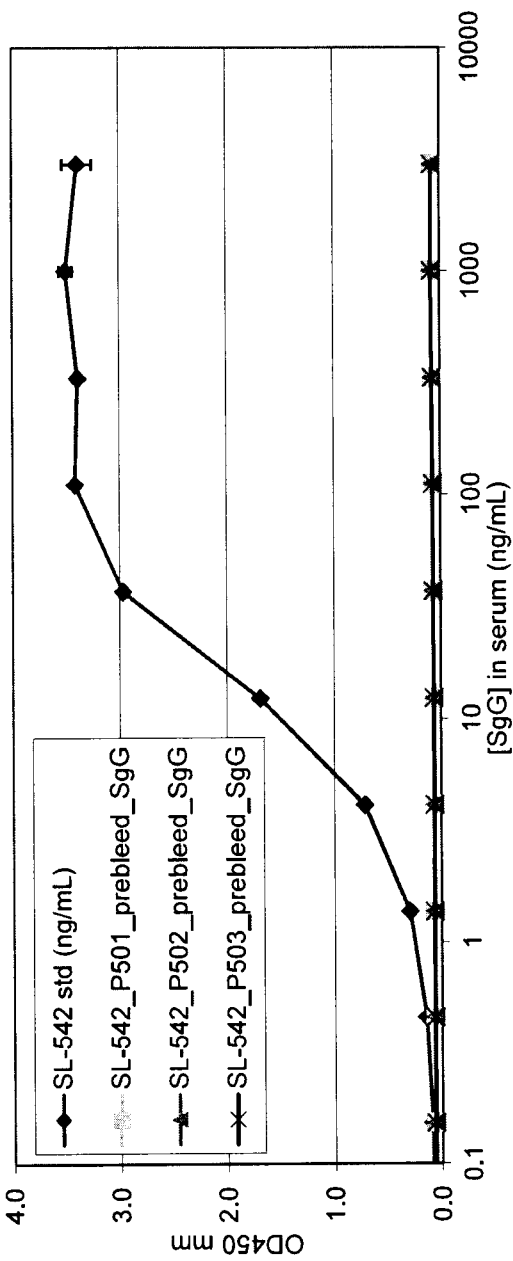

Detection of Target—Specific Surrobody™ (e.g., Target-Specific SLC) in PK *Cynomolgus* Monkey Serum Biologically naive *Cynomolgus* monkeys were used to evaluate five SgG test articles, as identified in FIG. 17A-FIG. 17C. Three monkeys were studied in each of the test article groups. Among the five groups there was a total of 15 monkeys, weighing 3.37-5.67 kg each and health reports were maintained for each monkey. The mean weight of each group was 4.34-4.87 kg. A single 10 mg/mL injection was given by i.v. Each monkey serum was collected and prepared at up to 28 days. The time points for serum collection included short intervals (0 and 5 min), intermediate intervals (1, 4, 8 and 24 hrs) and long intervals (48 hr (2 d), 72 hr (3 d), 96 hr (4 d), 168 hr (7 d), 240 hr (10 d), 336 hr (14 d), 408 hr (17 d), 504 hr (21 d), 576 hr (24 d), and 672 hr (28 d)).

TABLE 6

Human $V_L$ Protein Sequence Similarities

| | VpredT-λ5_J(F1) | VpreBdT-λ5_B11 JL (F2) | VL5e_JL | VL1b_JL | VL1c_JL | VL2a2_JL | VL3I_JL | VL3m_JL |
|---|---|---|---|---|---|---|---|---|
| VpredT-λ5_J(F1) | 100 | 98 | 60 | 41 | 44 | 44 | 42 | 42 |
| VpreBdT-λ5_B11 JL (F2) | | 100 | 62 | 43 | 46 | 46 | 44 | 44 |
| VL5e_JL | | | 100 | 52 | 56 | 55 | 50 | 55 |
| VL1b_JL | | | | 100 | 62 | 68 | 66 | 62 |
| VL1c_JL | | | | | 100 | 69 | 62 | 59 |
| VL2a2_JL | | | | | | 100 | 65 | 64 |
| VL3I_JL | | | | | | | 100 | 75 |
| VL3m_JL | | | | | | | | 100 |

ELISA assays were used for detecting SgG in the *Cynomolgus* monkey serum. One PK timepoint was assayed per plate and a serial dilution of standard/sample was performed in 2 mL deep-well blocks. The 1:3 serial dilution comprised 800 μL 1% BSA-PB ST+400 μL sample. One dilution was made for each of the HGF-binding, PlGF-binding and complex ELISAs.

Figure 18A:
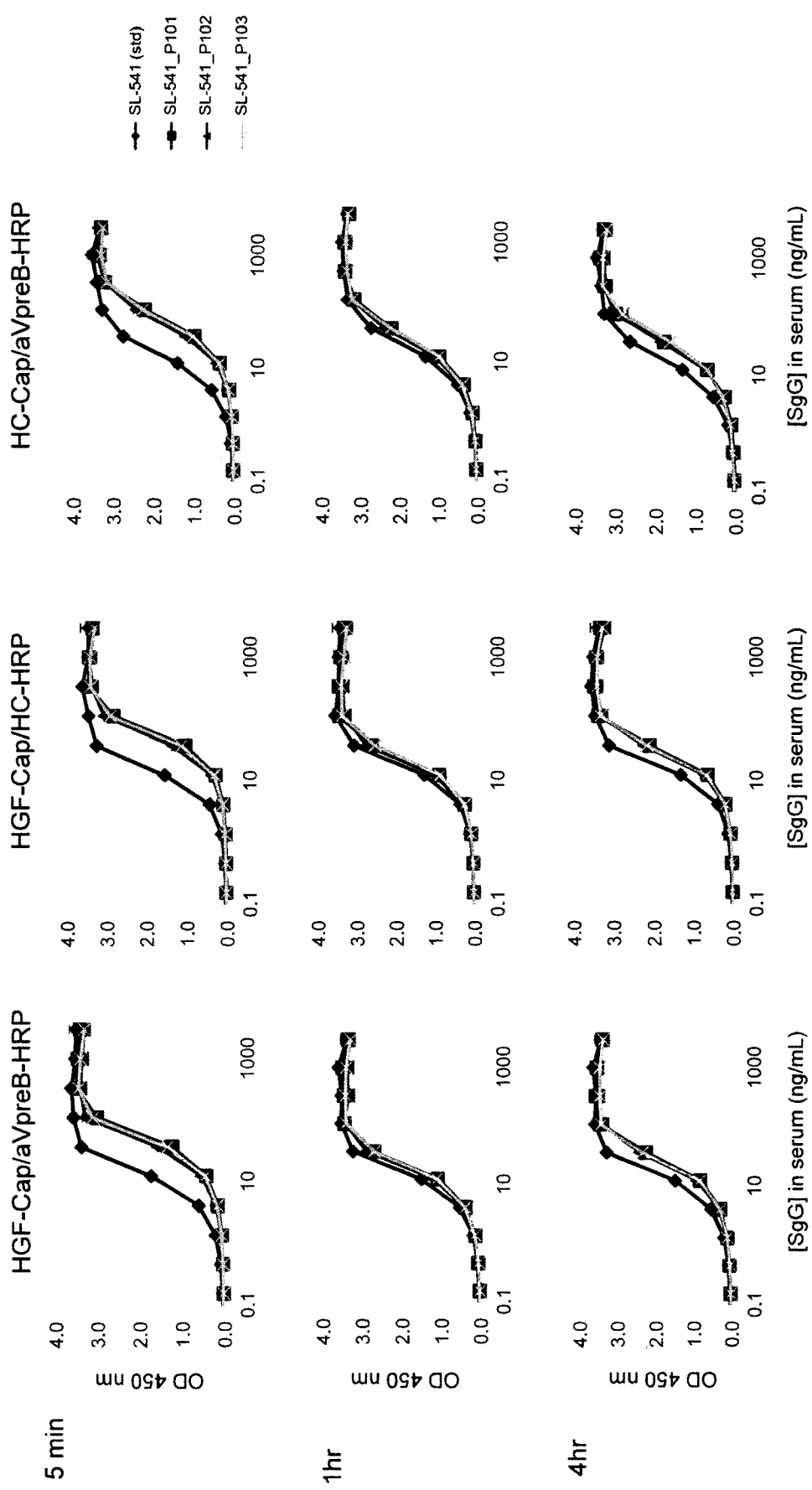
FIG. 18A-FIG. 18C show the PK serum ELISA results for SL-541_αHGF SgG over the 5 min to 96 hr time-points.
Figure 18B:
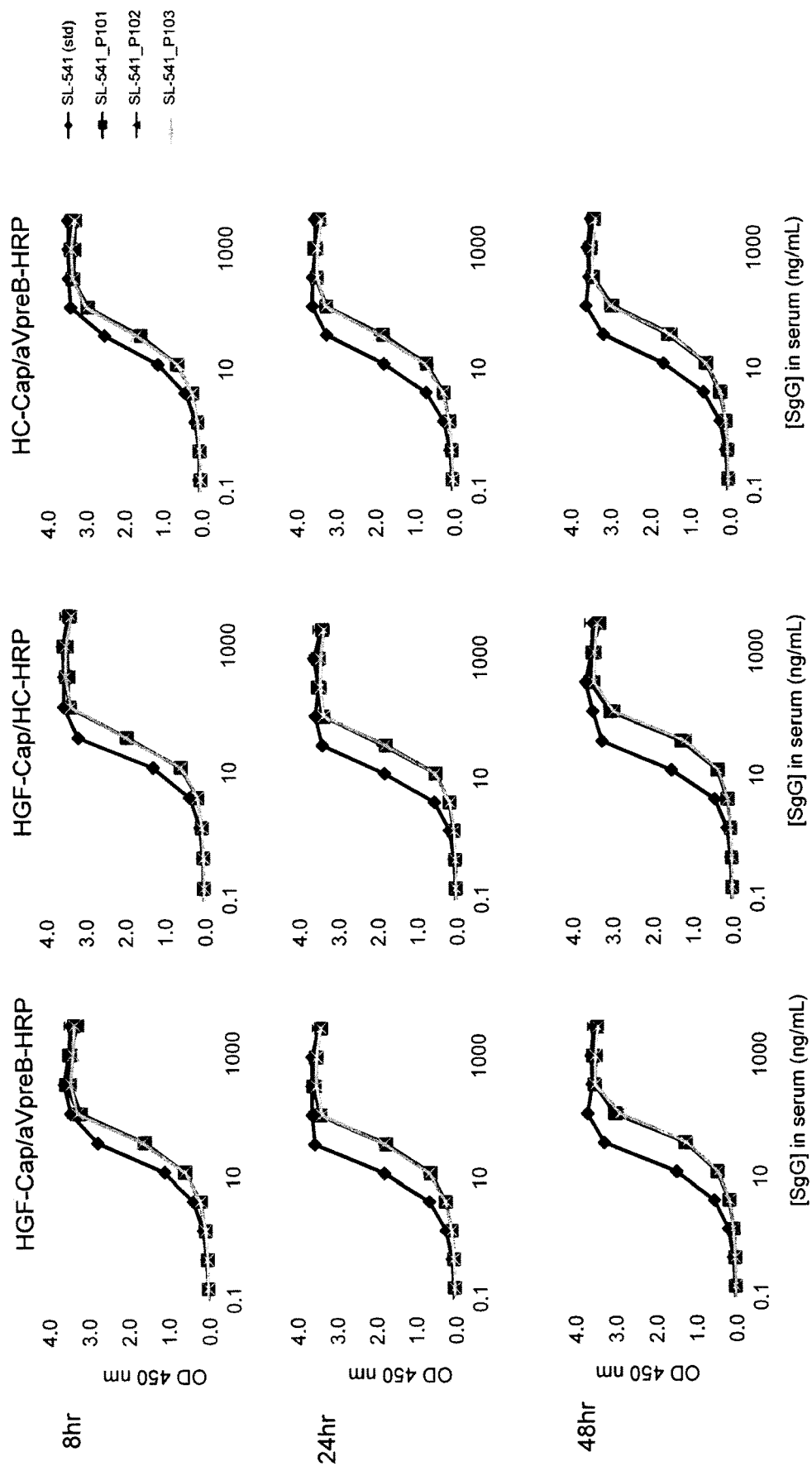
Figure 18C:
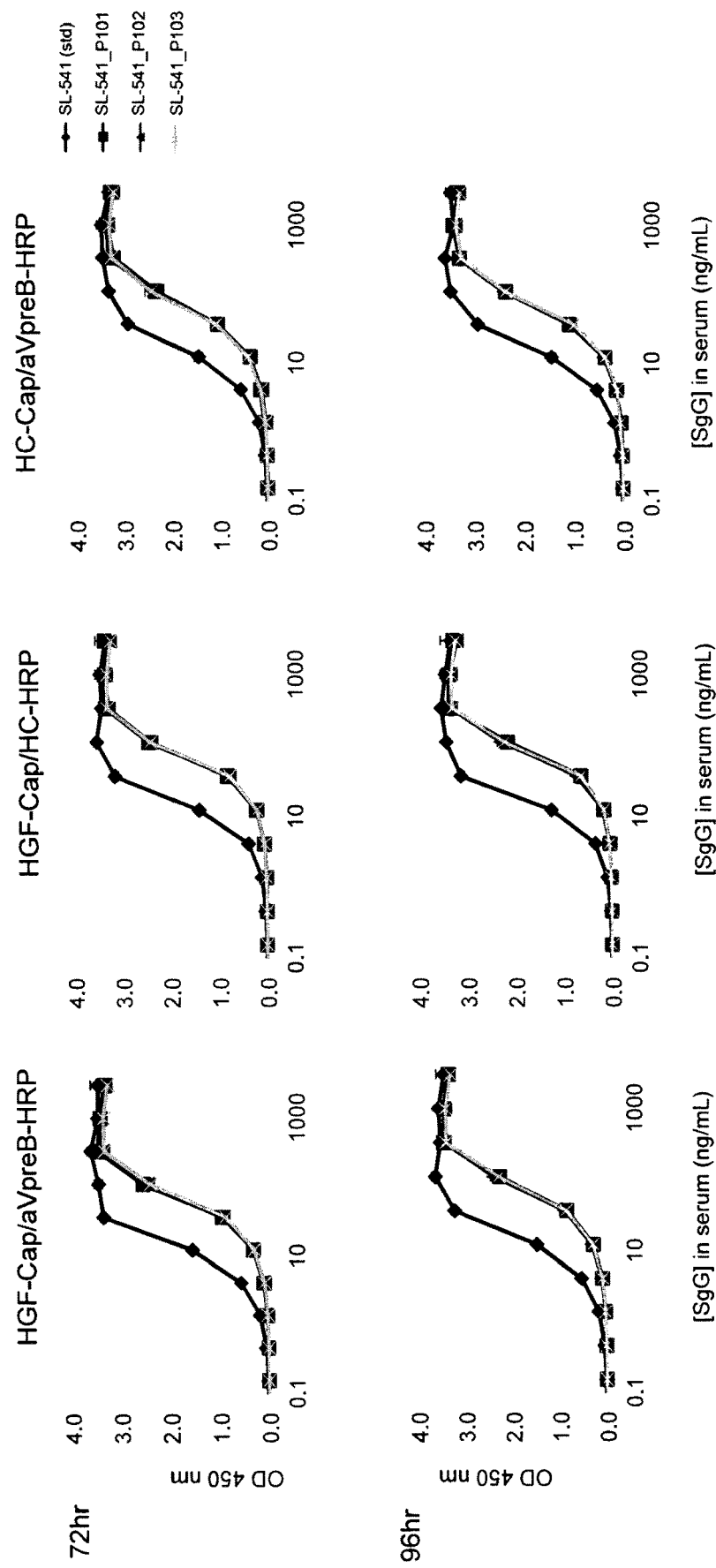
Figure 19A:
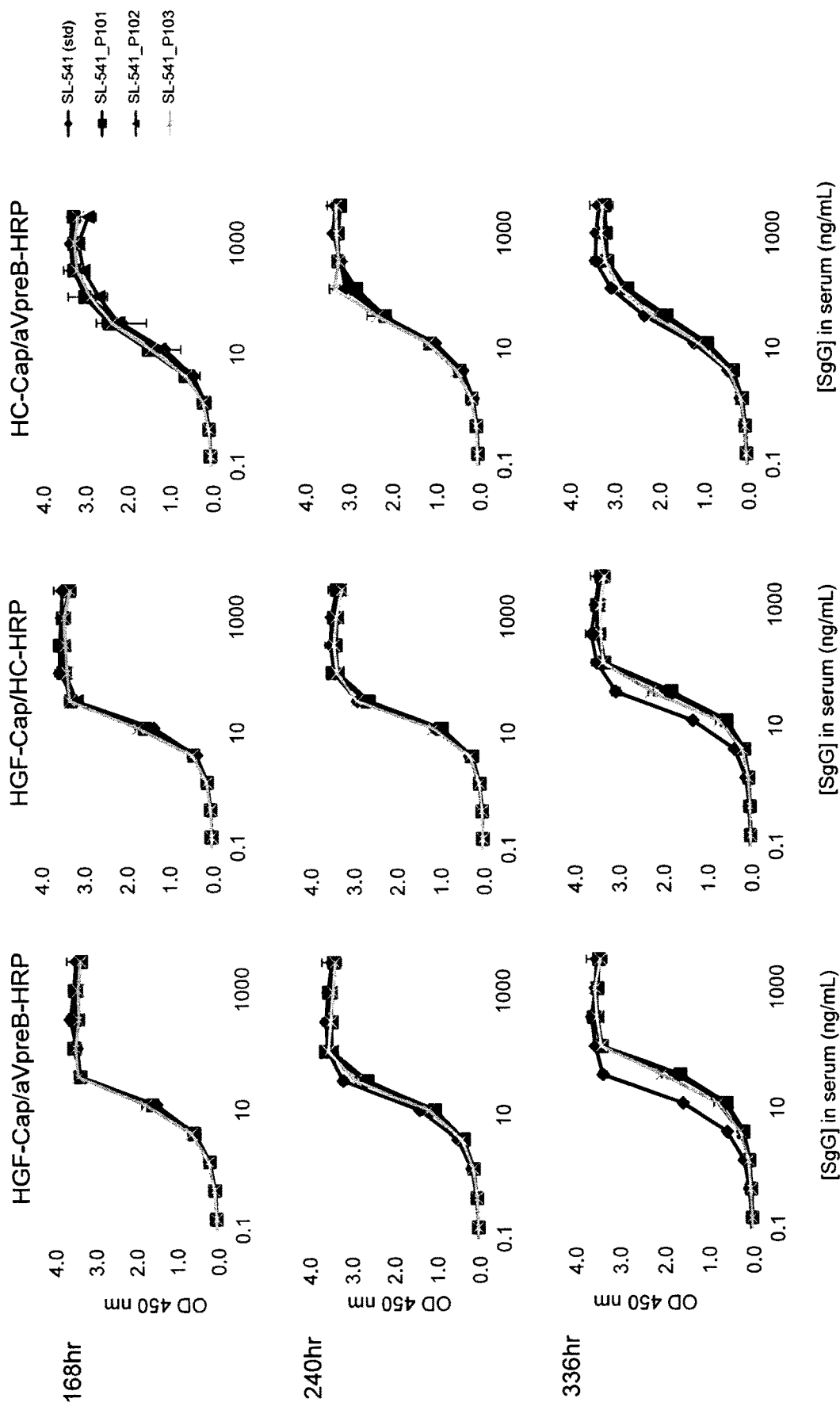
FIG. 19A-FIG. 19C show the PK serum ELISA results for SL-541_αHGF SgG over the 168 hr to 672 hr time-points.
Figure 19B:
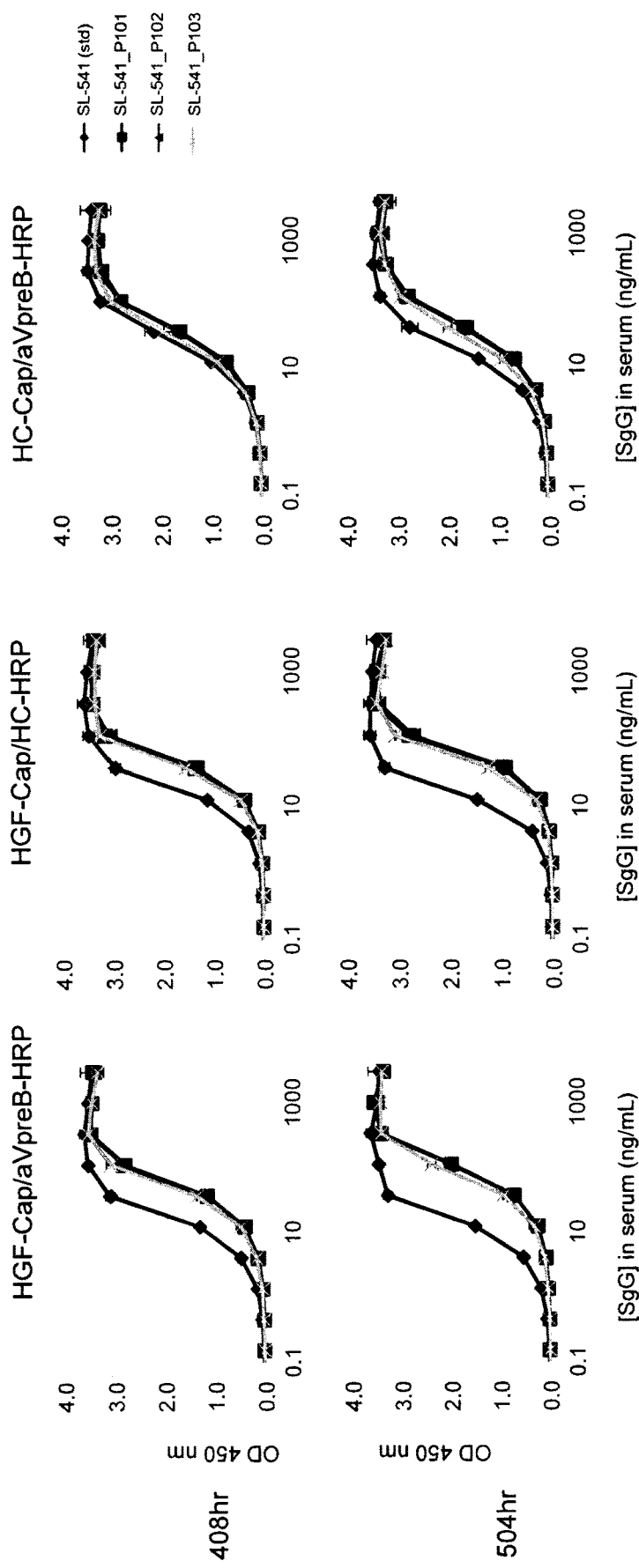
Figure 19C:
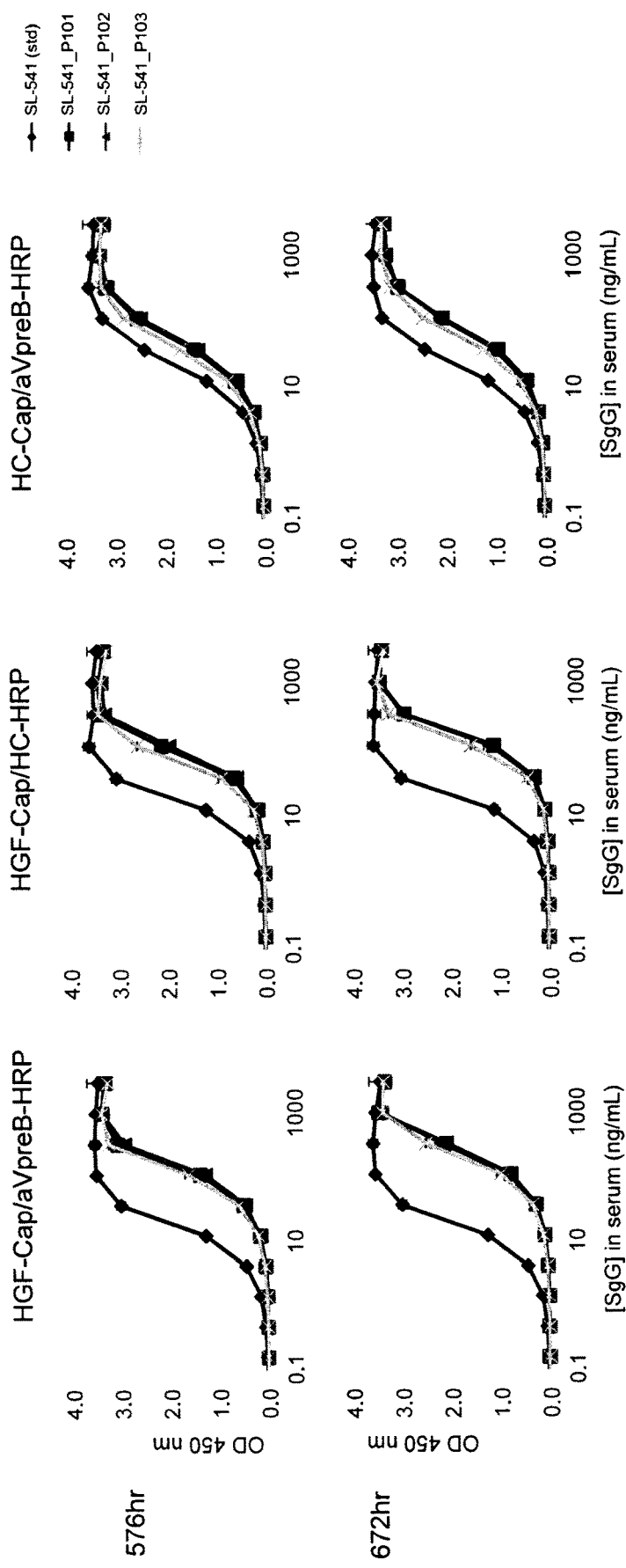
Figure 20A:
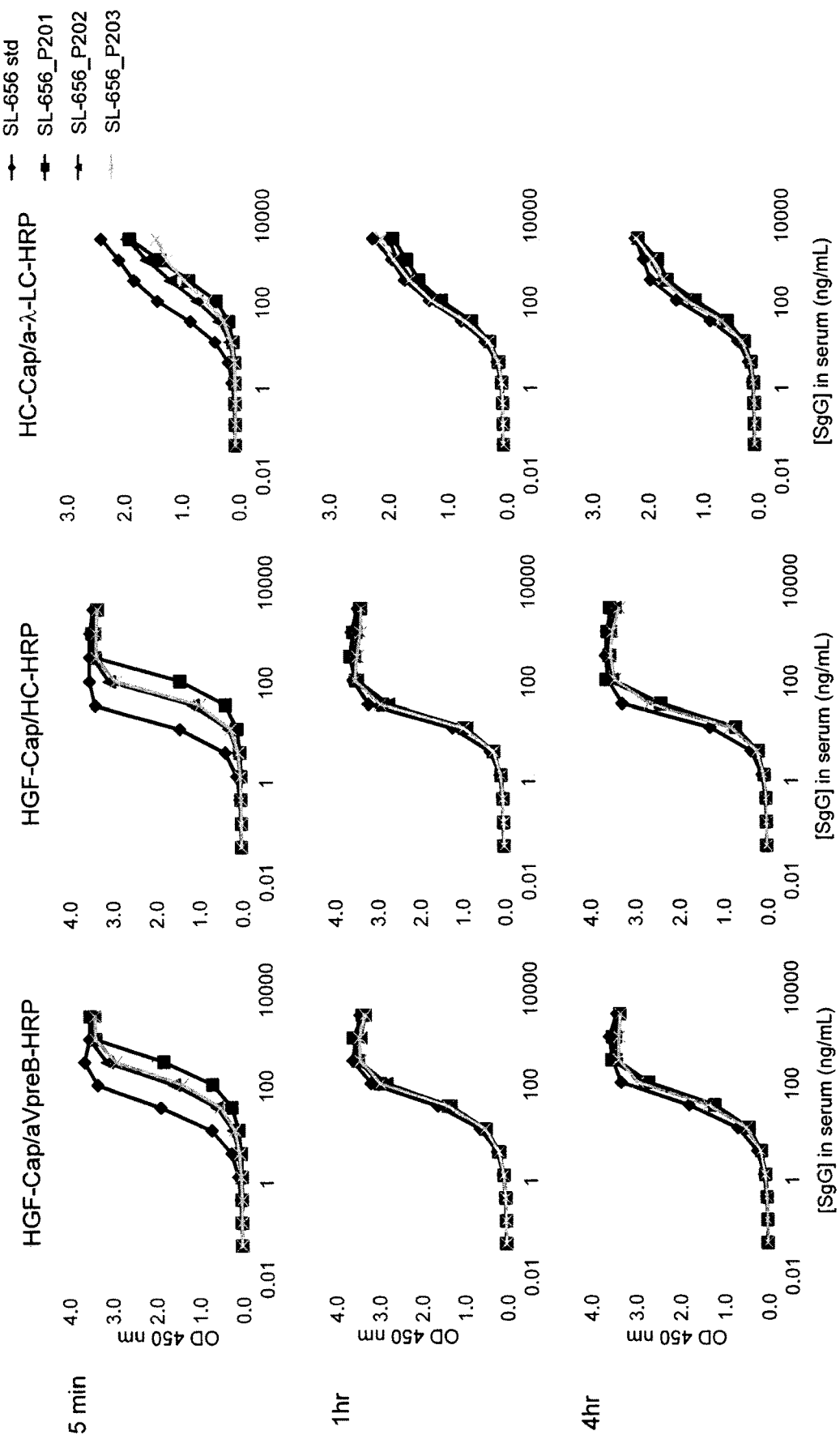
FIG. 20A-FIG. 20C show the PK serum ELISA results for SL-656_αHGF SgG over the 5 min to 96 hr timepoints.
Figure 20B:
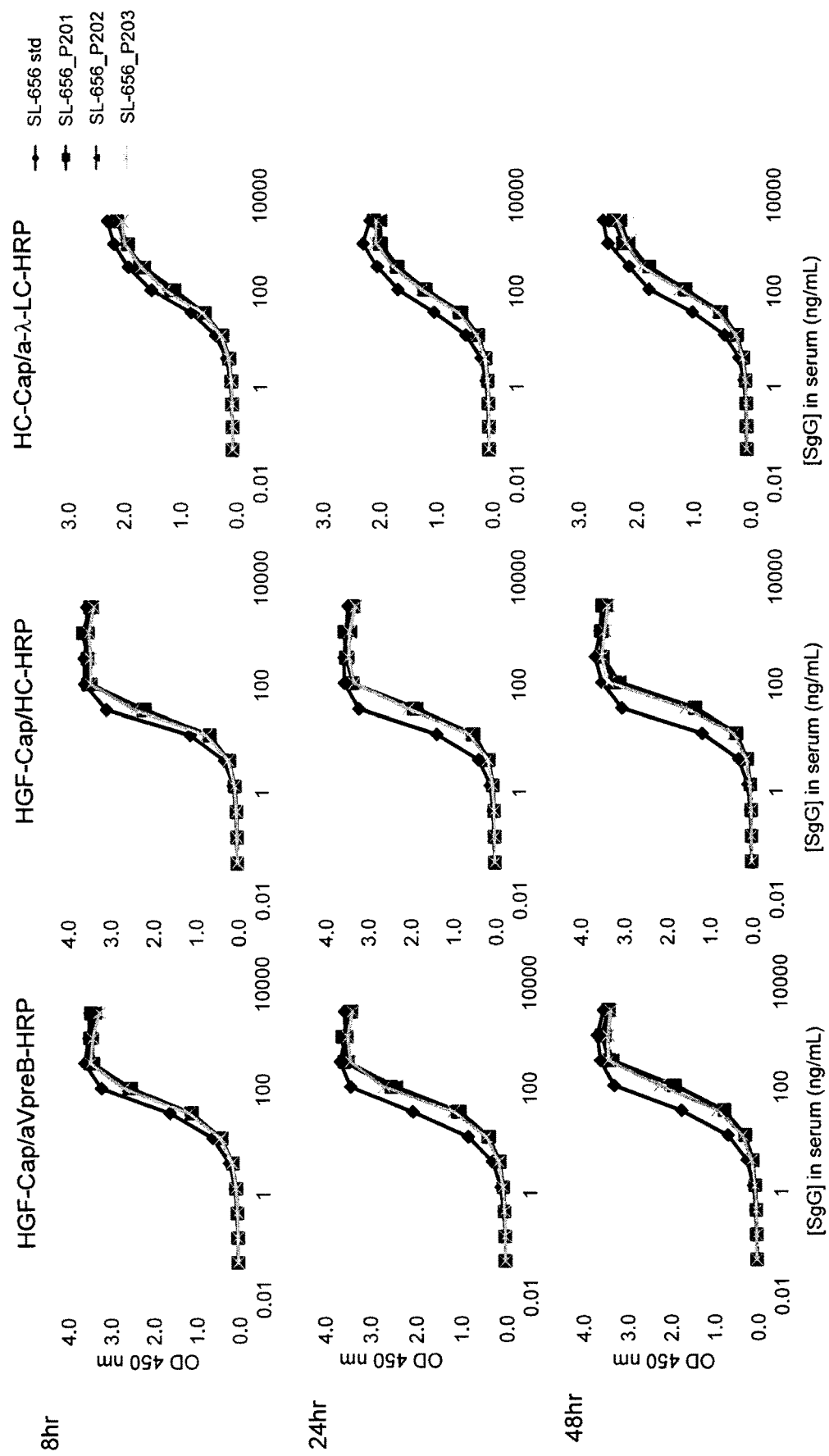
Figure 20C:
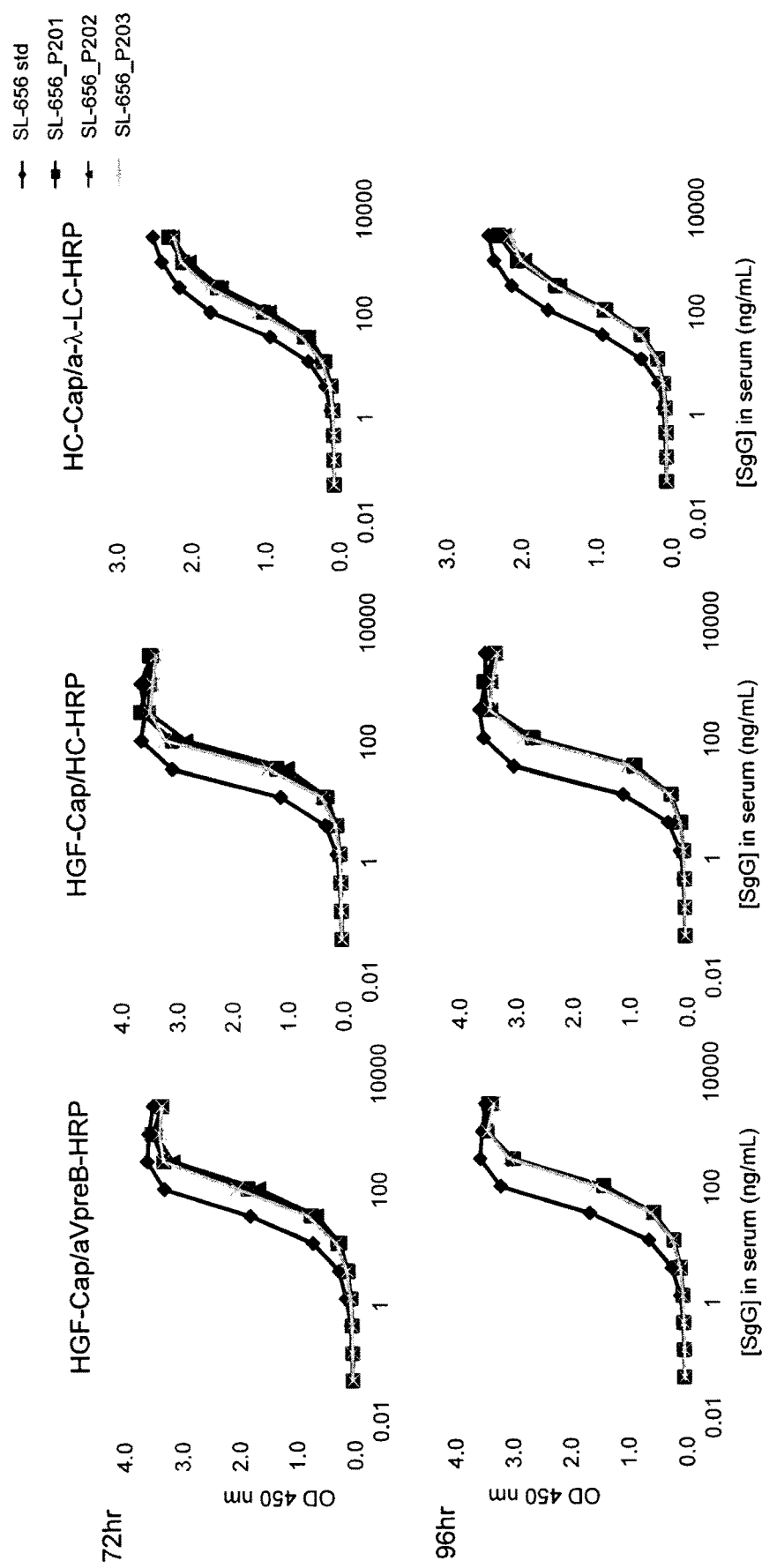
Figure 21A:
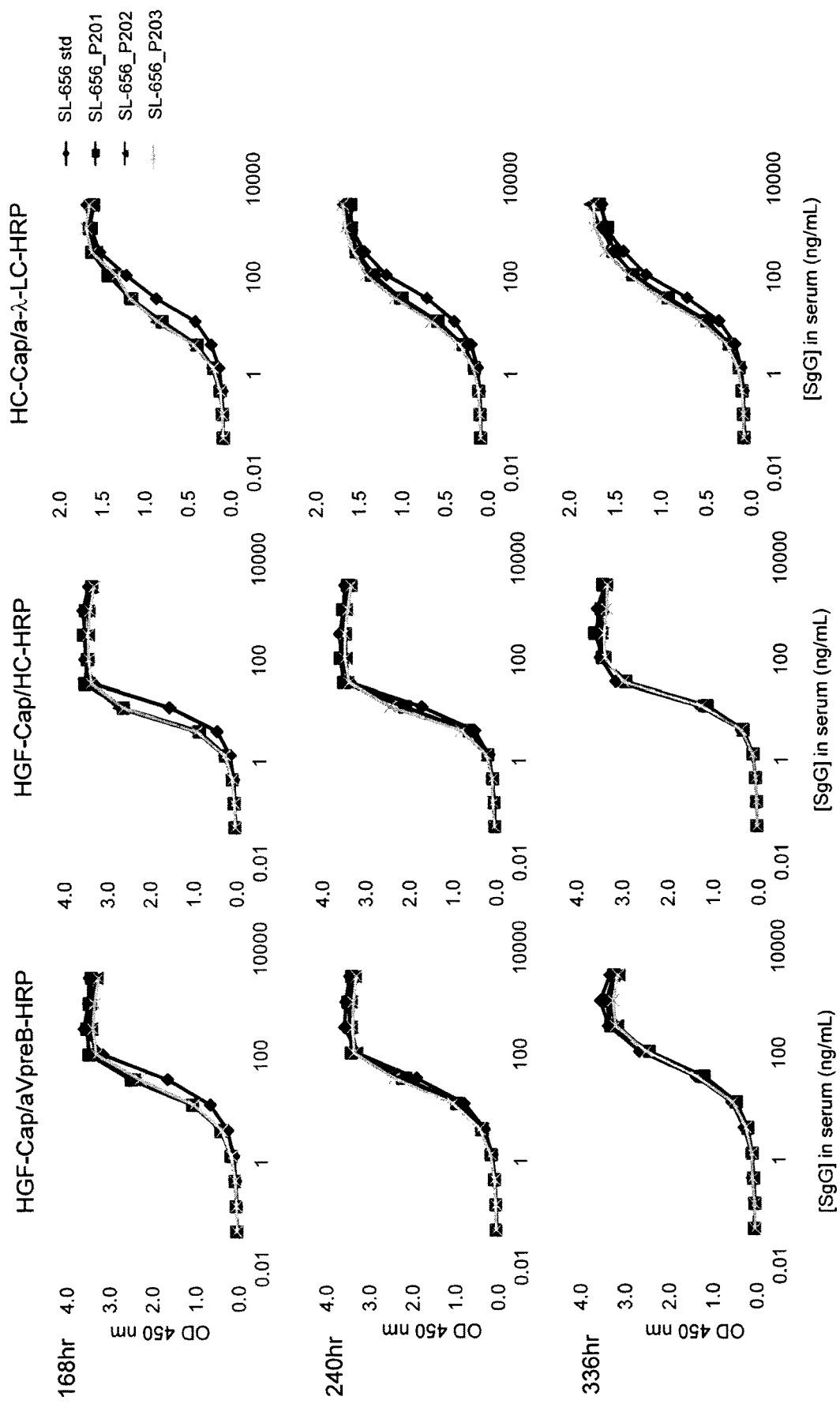
FIG. 21A-FIG. 21C show the PK serum ELISA results for SL-656_αHGF SgG over the 168 hr to 672 hr time-points.
Figure 21B:
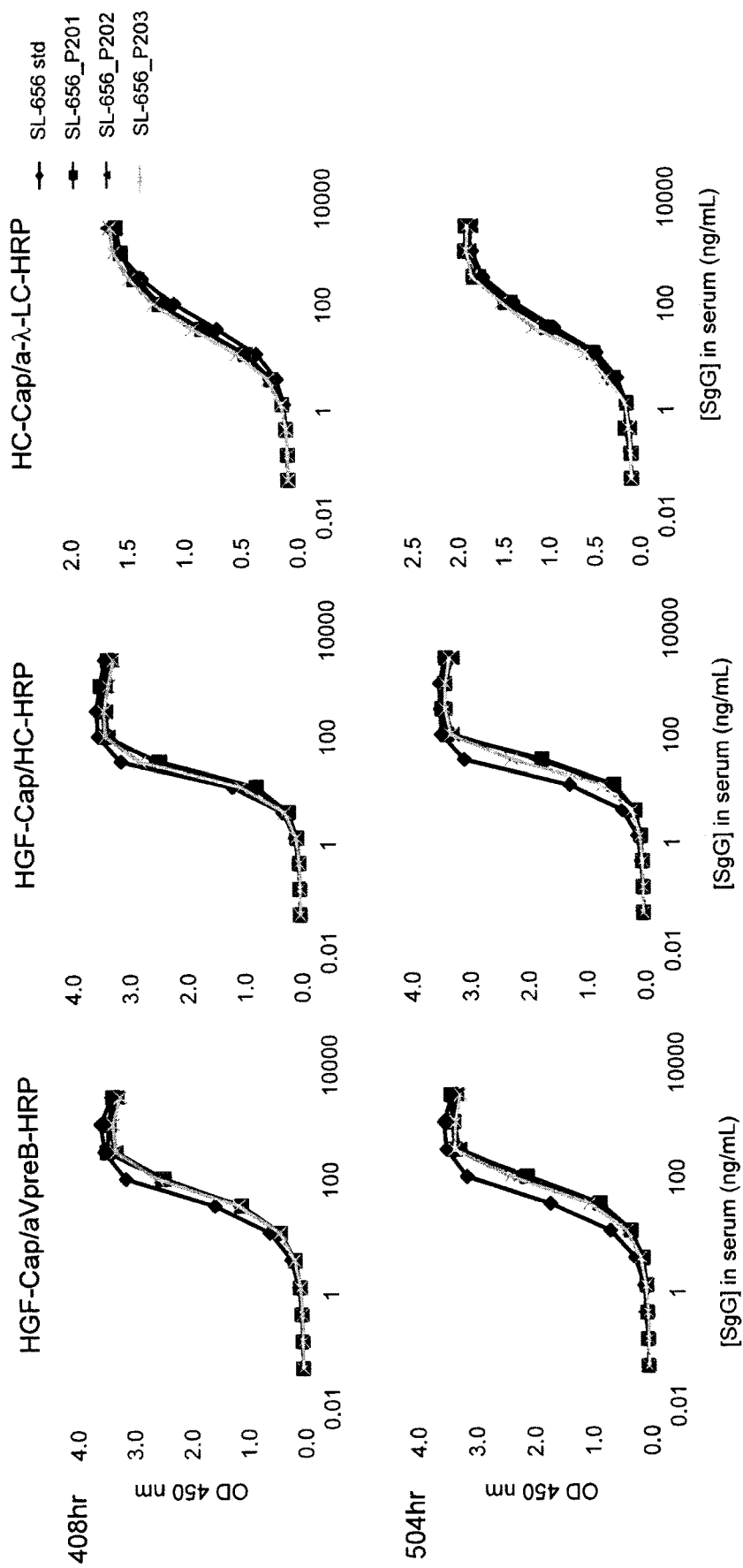
Figure 21C:
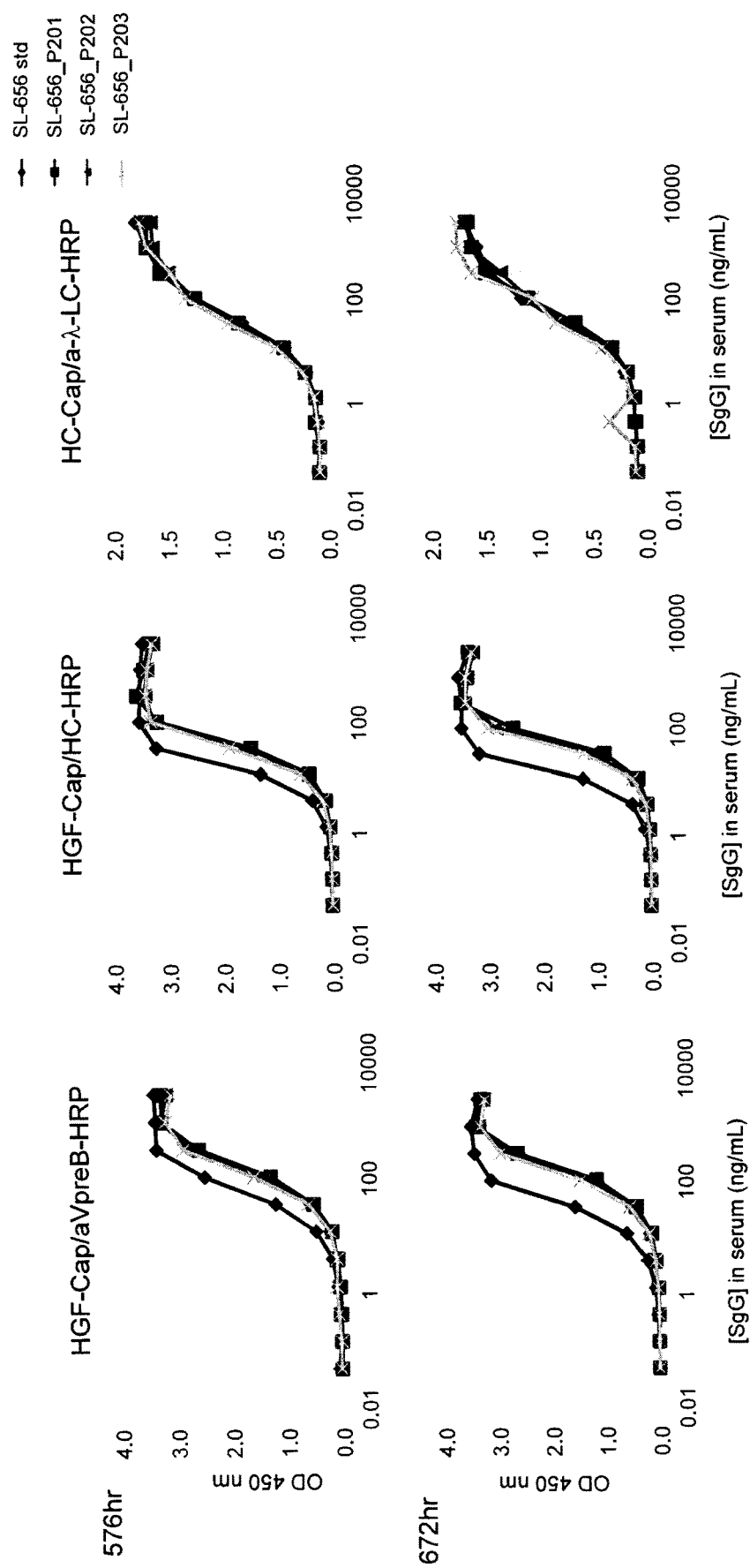

The pre-immune serum samples from all monkeys in each of the 5 test groups were clean for SgG proteins (FIG. 17A-FIG. 17C). An example of the ELISA data gathered for SL-541_αHGF SgG over the 5 min-96 hr time-points is provided in FIG. 18A-FIG. 18C and the data for this SgG structure over the 168 hr-672 hr timepoints is provided in FIG. 19A-FIG. 19C. An example of the ELISA data gathered for SL-656_αHGF IgG over the 5 min-96 hr timepoints is provided in FIG. 20A-FIG. 20C and the data for this SgG structure over the 168 hr-672 hr timepoints is provided in FIG. 21A-FIG. 21C. The results indicate that the half-life of the test subject ranged from 6-10 days. These results further demonstrate the utility of the VpreB1 IgG mAb (2460B04 IgG1) for determining the PK properties of therapeutic Surrobodies™ (e.g., surrogate light chain constructs). PK studies help determine the distribution, metabolism, and elimination of potential therapeutic drugs. These data will provide a basis for historical comparison between the investigational therapeutic product and a licensed therapeutic, as well as help determine the optimum dosing schedule and withdrawal period for the product. Thus, the VpreB1 IgG mAbs are useful for determining the proper dosing of Surrobodies™ (e.g., surrogate light chain constructs), by establishing both a clinically efficacious amount and the clearance time to achieve the clinically relevant dose.

Figure 22:
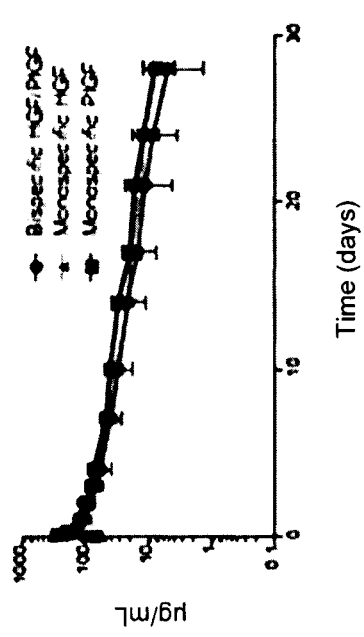
FIG. 22 shows the PK properties of bispecific Surrobodies™ (e.g., bi-specific surrogate light chain constructs).

We also looked at the PK properties of bispecific Surrobodies™ (e.g. surrogate light chain constructs) and found them to be comparable to parental constructs in *Cynomolgus*. (FIG. 22). Naïve groups (n=3) of *Cynomolgus* monkeys were administered single IV doses of Surrobodies™ (e.g., surrogate light chain constructs) (10 mg/kg) and their serum was tested over a 28 day period. The overall PK properties of the bispecific Surrobodies™ (e.g., surrogate light chain constructs) were found to be very similar to the monspecific HGF and PlGF Surrobodies™ (e.g., surrogate light chain constructs).

Although in the foregoing description the invention is illustrated with reference to certain embodiments, it is not so limited. Indeed, various modifications of the invention in addition to those shown and described herein will become apparent to those skilled in the art from the foregoing description and fall within the scope of the appended claims.

All publications, patents and patent applications cited herein are hereby incorporated by reference in their entirety for all purposes to the same extent as if each individual publication, patent or patent application were specifically and individually indicated to be so incorporated by reference.

---

The invention claimed is:

1. An isolated antibody, or antigen-binding fragment thereof, that specifically binds to a surrogate light chain (SLC) protein, wherein the SLC protein comprises a VpreB1 subunit, and wherein the VpreB1 subunit comprises an amino acid sequence of SEQ ID NO: 1, comprising:

(a) a light chain variable region sequence of SEQ ID NO: 36 and a heavy chain variable region sequence of SEQ ID NO: 52;

(b) a light chain variable region sequence of SEQ ID NO: 37 and a heavy chain variable region sequence of SEQ ID NO: 53;

(c) a light chain variable region sequence of SEQ ID NO: 38 and a heavy chain variable region sequence of SEQ ID NO: 54;

(d) a light chain variable region sequence of SEQ ID NO: 39 and a heavy chain variable region sequence of SEQ ID NO: 55;

(e) a light chain variable region sequence of SEQ ID NO: 40 and a heavy chain variable region sequence of SEQ ID NO: 56;

(f) a light chain variable region sequence of SEQ ID NO: 41 and a heavy chain variable region sequence of SEQ ID NO: 57;

(g) a light chain variable region sequence of SEQ ID NO: 42 and a heavy chain variable region sequence of SEQ ID NO: 58;

(h) a light chain variable region sequence of SEQ ID NO: 43 and a heavy chain variable region sequence of SEQ ID NO: 59;

(i) a light chain variable region sequence of SEQ ID NO: 44 and a heavy chain variable region sequence of SEQ ID NO: 60;

(j) a light chain variable region sequence of SEQ ID NO: 45 and a heavy chain variable region sequence of SEQ ID NO: 61;

(k) a light chain variable region sequence of SEQ ID NO: 46 and a heavy chain variable region sequence of SEQ ID NO: 62;

(l) a light chain variable region sequence of SEQ ID NO: 47 and a heavy chain variable region sequence of SEQ ID NO: 63;

(m) a light chain variable region sequence of SEQ ID NO: 48 and a heavy chain variable region sequence of SEQ ID NO: 64;

(n) a light chain variable region sequence of SEQ ID NO: 49 and a heavy chain variable region sequence of SEQ ID NO: 65;

(o) a light chain variable region sequence of SEQ ID NO: 50 and a heavy chain variable region sequence of SEQ ID NO: 66; or (p) a light chain variable region sequence of SEQ ID NO: 51 and a heavy chain variable region sequence of SEQ ID NO: 67.

2. The antibody of claim 1, wherein said antigen-binding fragment is selected from the group consisting of Fab, Fab', F(ab')$_2$, scFv, and (scFv)$_2$ fragments.

3. The antibody of claim 1, wherein the SLC protein further comprises a λ5 subunit.

4. The antibody of claim 3, wherein the λ5 subunit is a human λ5 protein comprising an amino acid sequence of SEQ ID NO: 7.

5. The antibody of claim 4, wherein the λ5 subunit is a human λ5 dTail protein comprising SEQ ID NO: 9.

6. A composition comprising an isolated antibody, or antigen-binding fragment thereof, that specifically binds to a surrogate light chain (SLC) protein, wherein the SLC protein comprises a VpreB1 subunit, and wherein the VpreB1 subunit comprises an amino acid sequence of SEQ ID NO: 1, and wherein the antibody, or antigen-binding fragment thereof comprises:

(a) a light chain variable region sequence of SEQ ID NO: 36 and a heavy chain variable region sequence of SEQ ID NO: 52;

(b) a light chain variable region sequence of SEQ ID NO: 37 and a heavy chain variable region sequence of SEQ ID NO: 53;

(c) a light chain variable region sequence of SEQ ID NO: 38 and a heavy chain variable region sequence of SEQ ID NO: 54;

(d) a light chain variable region sequence of SEQ ID NO: 39 and a heavy chain variable region sequence of SEQ ID NO: 55;

(e) a light chain variable region sequence of SEQ ID NO: 40 and a heavy chain variable region sequence of SEQ ID NO: 56;

(f) a light chain variable region sequence of SEQ ID NO: 41 and a heavy chain variable region sequence of SEQ ID NO: 57;

(g) a light chain variable region sequence of SEQ ID NO: 42 and a heavy chain variable region sequence of SEQ ID NO: 58;

(h) a light chain variable region sequence of SEQ ID NO: 43 and a heavy chain variable region sequence of SEQ ID NO: 59;

(i) a light chain variable region sequence of SEQ ID NO: 44 and a heavy chain variable region sequence of SEQ ID NO: 60;

(j) a light chain variable region sequence of SEQ ID NO: 45 and a heavy chain variable region sequence of SEQ ID NO: 61;

(k) a light chain variable region sequence of SEQ ID NO: 46 and a heavy chain variable region sequence of SEQ ID NO: 62;

(l) a light chain variable region sequence of SEQ ID NO: 47 and a heavy chain variable region sequence of SEQ ID NO: 63;

(m) a light chain variable region sequence of SEQ ID NO: 48 and a heavy chain variable region sequence of SEQ ID NO: 64;

(n) a light chain variable region sequence of SEQ ID NO: 49 and a heavy chain variable region sequence of SEQ ID NO: 65;

(o) a light chain variable region sequence of SEQ ID NO: 50 and a heavy chain variable region sequence of SEQ ID NO: 66; or (p) a light chain variable region sequence of SEQ ID NO: 51 and a heavy chain variable region sequence of SEQ ID NO: 67.

* * * * *